United States Patent
Sakai

(10) Patent No.: US 11,819,391 B2
(45) Date of Patent: Nov. 21, 2023

(54) ABSORBENT ARTICLE AND METHOD FOR MANUFACTURING SAME

(71) Applicant: Daio Paper Corporation, Ehime (JP)

(72) Inventor: Syunsuke Sakai, Tochigi (JP)

(73) Assignee: DAIO PAPER CORPORATION, Ehime (JP)

( * ) Notice: Subject to any disclaimer, the term of this patent is extended or adjusted under 35 U.S.C. 154(b) by 721 days.

(21) Appl. No.: 16/907,881

(22) Filed: Jun. 22, 2020

(65) Prior Publication Data

US 2020/0397625 A1 Dec. 24, 2020

Related U.S. Application Data

(62) Division of application No. 15/547,019, filed as application No. PCT/JP2016/052805 on Jan. 29, 2016, now Pat. No. 10,849,797.

(30) Foreign Application Priority Data

Jan. 30, 2015 (JP) .................................. 2015-017498
Mar. 27, 2015 (JP) .................................. 2015-067324
(Continued)

(51) Int. Cl.
  A61F 13/49 (2006.01)
  B29C 65/00 (2006.01)
  (Continued)

(52) U.S. Cl.
  CPC .. *A61F 13/49009* (2013.01); *A61F 13/15739* (2013.01); *A61F 13/49012* (2013.01);
  (Continued)

(58) Field of Classification Search
  CPC .......... A61F 13/49009; A61F 13/15739; A61F 13/49012; A61F 13/49015;
  (Continued)

(56) References Cited

U.S. PATENT DOCUMENTS 5,567,501 A   10/1996 Srinivasan et al.
5,851,935 A   12/1998 Srinivasan et al.
(Continued)

FOREIGN PATENT DOCUMENTS

CN   104203177 A   12/2014
EP    3202383 A1    8/2017
(Continued)

*Primary Examiner* — George R Koch
*Assistant Examiner* — Christopher C Caillouet
(74) *Attorney, Agent, or Firm* — Muncy, Geissler, Olds & Lowe

(57) ABSTRACT

In order to prevent degradation of appearance, prevent a decrease in flexibility, and improve non-elasticity in a non-stretchable region in an elastic film stretchable structure, the invention is characterized by having an elastic film stretchable structure (20X) formed by stacking an elastic film (30) between a first sheet layer (20A) and a second sheet layer (20B), wherein a region having the elastic film stretchable structure (20X) includes a non-stretchable region (70) and a stretchable region (80) provided at least at one side of the non-stretchable region (70) in a stretching and contracting direction, the stretchable region (80) being stretchable in the stretching and contracting direction, the first sheet layer (20A) and the second sheet layer (20B) are joined via through holes (31) penetrating the elastic film (30) at the large number of sheet bond portions (40) arranged at intervals, and the non-stretchable region (70) does not have a section in which the elastic film (30) linearly continues along the stretching and contracting direction, due to presence of the through holes (31), even though the elastic film (30) continues in the stretching and contracting direction.

4 Claims, 52 Drawing Sheets

(30) Foreign Application Priority Data

| | | |
|---|---|---|
| Mar. 31, 2015 | (JP) | 2015-071784 |
| Mar. 31, 2015 | (JP) | 2015-071786 |
| Sep. 30, 2015 | (JP) | 2015-195458 |

(51) Int. Cl.

| | |
|---|---|
| *A61F 13/15* | (2006.01) |
| *B29C 65/08* | (2006.01) |
| *A61F 13/496* | (2006.01) |
| *B32B 38/00* | (2006.01) |
| *A61F 13/515* | (2006.01) |
| *B29L 31/48* | (2006.01) |

(52) U.S. Cl.
CPC .. *A61F 13/49015* (2013.01); *A61F 13/49019* (2013.01); *B29C 65/08* (2013.01); *B29C 66/21* (2013.01); *B29C 66/344* (2013.01); *B29C 66/71* (2013.01); *A61F 13/496* (2013.01); *A61F 13/515* (2013.01); *A61F 2013/15869* (2013.01); *A61F 2013/15878* (2013.01); *A61F 2013/49022* (2013.01); *B29K 2995/0065* (2013.01); *B29K 2995/0069* (2013.01); *B29L 2031/4878* (2013.01); *B32B 38/0004* (2013.01)

(58) Field of Classification Search
CPC .............. A61F 13/49019; A61F 13/496; A61F 13/515; B29C 65/08; B29C 66/21; B29C 66/344; B29C 66/71; B29C 66/1122; B29C 66/7294; B29L 2031/4878; B32B 38/0004

See application file for complete search history.

(56) References Cited

U.S. PATENT DOCUMENTS

| | | | |
|---|---|---|---|
| 6,572,595 | B1 | 6/2003 | Klemp et al. |
| 9,622,922 | B2 | 4/2017 | Nelson |
| 10,226,388 | B2 | 3/2019 | Nelson |
| 2001/0008676 | A1 | 7/2001 | Pelkie et al. |
| 2002/0016122 | A1 | 2/2002 | Curro et al. |
| 2004/0209042 | A1 | 10/2004 | Peacock |
| 2006/0247591 | A1 | 11/2006 | Hughes et al. |
| 2010/0163161 | A1 | 7/2010 | Gilgenbach et al. |
| 2010/0168705 | A1 | 7/2010 | Stabelfeldt et al. |
| 2010/0215923 | A1 | 8/2010 | Frost |
| 2011/0319853 | A1 | 12/2011 | Yamashita et al. |
| 2014/0130956 | A1 | 5/2014 | Floberg et al. |

FOREIGN PATENT DOCUMENTS

| | | |
|---|---|---|
| EP | 3299161 | 3/2018 |
| JP | 10029259 A | 2/1998 |
| JP | 2004532758 | 10/2004 |
| JP | 2006198132 A | 8/2006 |
| JP | 2008260131 A | 10/2008 |
| JP | 2008296585 A | 12/2008 |
| JP | 2010057567 A | 3/2010 |
| JP | 450885 B2 | 7/2010 |
| JP | 2010195044 A | 9/2010 |
| JP | 2010200974 A | 9/2010 |
| JP | 2011115308 A | 6/2011 |
| JP | 4934835 B2 | 5/2012 |
| JP | 2014150917 A | 8/2014 |
| JP | 2014520589 A | 8/2014 |
| JP | 2012070868 A | 2/2015 |
| JP | 2015033462 A | 2/2015 |
| JP | 2016140477 | 8/2016 |
| JP | 2016140477 A | 8/2016 |
| JP | 2016185265 A | 10/2016 |
| JP | 6383712 B2 | 8/2018 |
| WO | WO-91/04724 | 4/1991 |
| WO | WO-03/000165 A1 | 1/2003 |
| WO | WO-0300165 A1 | 1/2003 |
| WO | WO-2008126708 A1 | 10/2008 |
| WO | WO-2011048512 | 4/2011 |
| WO | WO-2011/080921 A1 | 7/2011 |
| WO | WO-2013/002691 A1 | 1/2013 |
| WO | WO-2015168032 A | 5/2014 |
| WO | WO-2016/052416 A1 | 4/2016 |

FIG.4A
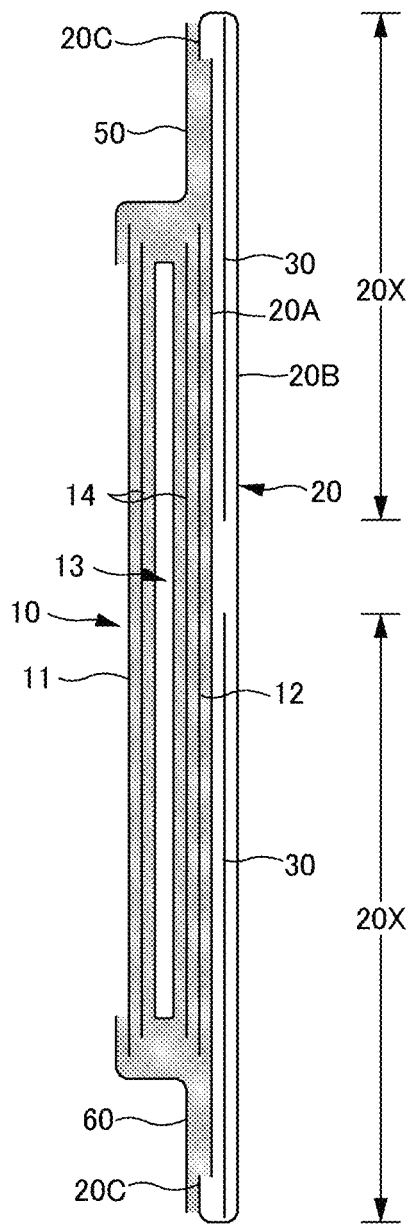
FIG.4B
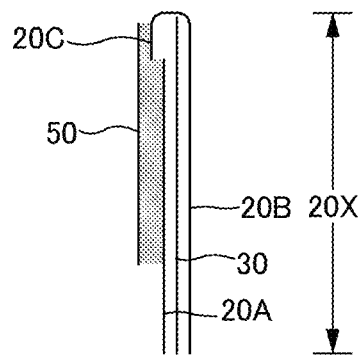
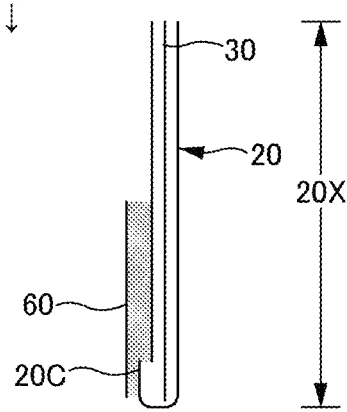

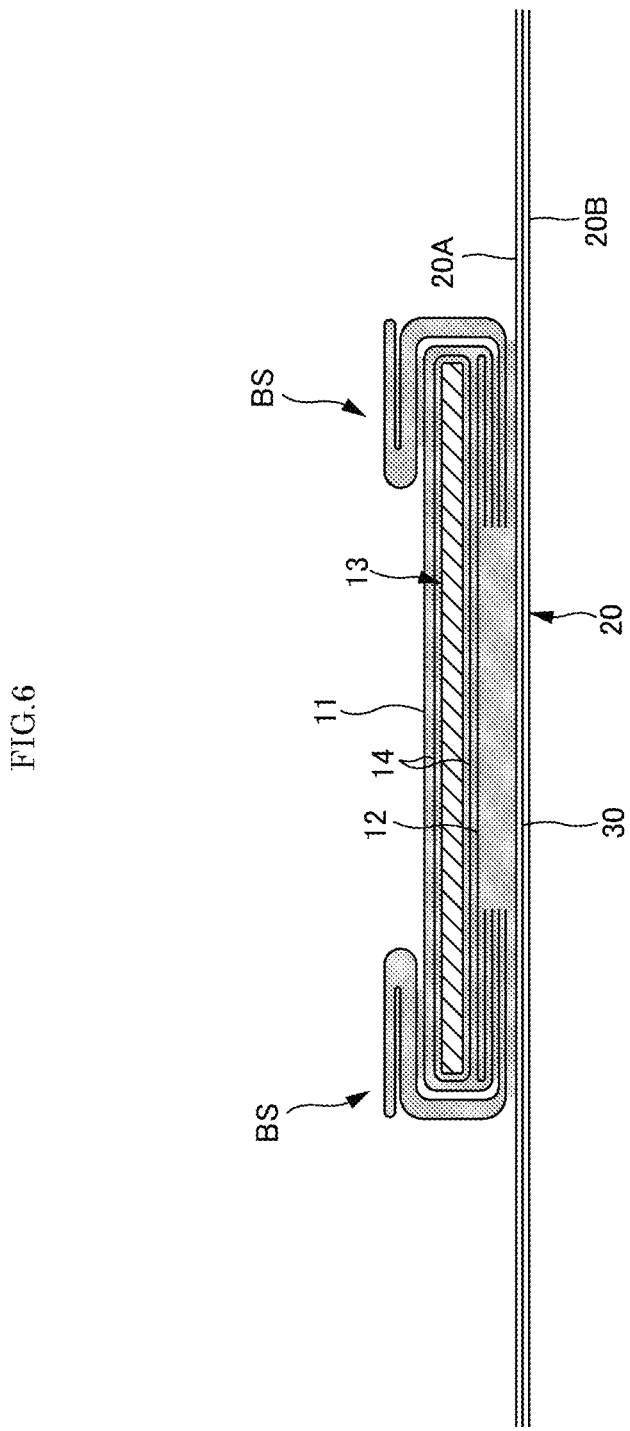

←Width direction(Stretching and Contracting direction)→

←Stretching and Contracting direction→

←Stretching and Contracting direction→

←Stretching and Contracting direction→

←Width direction(Stretching and Contracting direction)→

←Stretching and Contracting direction→

←Stretching and Contracting direction→

←Stretching and Contracting direction→

←Width direction(Stretching and Contracting direction)→

←Width direction(Stretching and Contracting direction)→

←Width direction(Stretching and Contracting direction)→

←Width direction(Stretching and Contracting direction)→

←Width direction(Stretching and Contracting direction)→

←Width direction(Stretching and Contracting direction)→

←Stretching and Contracting direction→

←Stretching and Contracting direction→

←Stretching and Contracting direction→

←Stretching and Contracting direction→

←Stretching and Contracting direction→

←Stretching and Contracting direction→

←Stretching and Contracting direction→

←Stretching and Contracting direction→

←Stretching and Contracting direction→

< Stretchable region 80 >

←Stretching and Contracting direction→

< Stretchable region 80 >

←Stretching and Contracting direction→

←Stretching and Contracting direction→

←Stretching and Contracting direction→

←Stretching and Contracting direction→

ABSORBENT ARTICLE AND METHOD FOR MANUFACTURING SAME

CROSS REFERENCE TO RELATED APPLICATIONS

This application is a Divisional of co-pending application Ser. No. 15/547,019, filed on Jul. 27, 2017, for which priority is claimed under 35 U.S.C. § 120; and this application claims priority of Application No. 2015-017498 filed in Japan on Jan. 30, 2015, Application No. 2015-067324 filed in Japan on Mar. 27, 2015, Application No. 2015-071784 filed in Japan on Mar. 31, 2015, Application No. 2015-071786 filed in Japan on Mar. 31, 2015, and Application No. 2015-195458 filed in Japan on Sep. 30, 2015 under 35 U.S.C. § 119, the entire contents of all of which are hereby incorporated by reference.

TECHNICAL FIELD

The present invention relates to an absorbent article having a stretchable structure in which an elastic film such as an elastic film is interposed between a first sheet layer and a second sheet layer, and a method of manufacturing the same.

BACKGROUND ART

In absorbent articles, elastic characteristics are typically imparted to leg portions, waist portions, and the like to improve fitness to the surfaces of bodies. A typical approach to impart elastic characteristics is fixing of elongated elastically stretchable members, such as rubber threads, in a state stretched in the longitudinal direction. In order to impart elasticity over a certain range of width, rubber threads are disposed and fixed in the width direction at intervals in some embodiments. In addition, an approach to impart excellent surface fitting is fixing of elastic film in a state stretched in a direction of imparting elasticity (for example, see Patent Literature 1).

According to a stretchable structure using the elastic film (hereinafter also referred to as an elastic film stretchable structure), a stretchable region is composed of a first sheet layer, a second sheet layer, and an elastic film interposed therebetween, and the first sheet layer and the second sheet layer are joined via through holes formed in the elastic film at a large number of dot-like sheet bond portions arranged at intervals in a stretching and contracting direction and a direction orthogonal thereto while the elastic film is stretched in the stretching and contracting direction along the surfaces of the first sheet layer and the second sheet layer. In such an elastic film stretchable structure, in a natural length state, as the elastic film contracts among the sheet bond portions, an interval between the two adjacent sheet bond portions is decreased, and a contraction wrinkle extending in the direction orthogonal to the stretching and contracting direction is formed between the sheet bond portions in the first sheet layer and the second sheet layer. On the contrary, in a stretched state, as the elastic film is stretched between the sheet bond portions, the interval between the two adjacent sheet bond portions is increased and the contraction wrinkle in the first sheet layer and the second sheet layer is stretched, and elastic stretching is allowed so that the first sheet layer and the second sheet layer can be fully spread. This elastic film stretchable structure has advantages as follows: surface fitness is excellent; the first sheet layer and the second sheet layer are not joined to the elastic film and joined each other but at an extremely low level, thus the elastic film stretchable structure has a satisfactory flexibility; and the through holes of the elastic film contribute to improvement in air permeability.

In order to simplify the manufacture of absorbent articles having a stretchable region only at a given position, an approach has been adopted which involves fixing elastically stretchable members in a large area including the stretchable region imparting elasticity, and performing a process to reduce or eliminate the contraction force of the elastically stretchable members to form a non-stretchable region requiring no elasticity (hereinafter also referred to as eliminating elasticity). For example, to impart elasticity in the width direction to the waist portion of an underpants-type disposable diaper, a typical approach has been widely adopted which involves fixing elongated elastically stretchable members over the entire width direction, and cutting some of elastically stretchable members overlapping with an absorber disposed at a middle of the width direction into small fractions to eliminate the elasticity of the elastically stretchable members, the non-stretchable region is thereby formed.

However, when such an approach to eliminate the elasticity of the stretchable structure including rubber threads by cutting the rubber threads is applied to the elastic film stretchable structure without change, the whole elastic film becomes to be cut in the direction orthogonal to the stretching and contracting direction at least in the non-stretchable region, and continuous cutting is required in a large area. Thus, there is a concern that the first sheet layer and the second sheet layer may be cut, or a concern that a cutting trace (a melting trace or pressing trace) may be continuously left in the first sheet layer and the second sheet layer even when the first sheet layer and the second sheet layer are not cut. In addition, it is difficult to manufacture.

CITATION LIST

Patent Literature

Patent Literature 1: JP 2004-532758 A

SUMMARY OF INVENTION

Technical Problem

In this regard, a main object of the invention is to provide a novel non-stretchable region in an elastic film stretchable structure and a method of forming the same.

Solution to Problem

The invention solving the above-mentioned problem is described below.

An absorbent article having an absorber that absorbs excrement, the absorbent article comprising an elastic film stretchable structure in which an elastic film is stacked between a first sheet layer and a second sheet layer, and the first sheet layer and the second sheet layer are joined via through holes penetrating the elastic film at a large number of sheet bond portions arranged at intervals, wherein a region having the elastic film stretchable structure includes a stretchable region stretchable in one direction and a non-stretchable region provided at least at one side of the stretchable region in a stretching and contracting direction, the stretchable region has a section in which the elastic film linearly continues along the stretching and contracting direction, the stretchable region is contracted in the stretching and contracting direction by a contraction force of the elastic film while it is possible that the stretchable region is stretched in the stretching and contracting direction, and the non-stretchable region, due to presence of the through holes, does not have a section in which the elastic film linearly continues along the stretching and contracting direction, even though the elastic film of the non-stretchable region continues in the stretching and contracting direction.

(Operational Advantage)

In the elastic film stretchable structure according to the invention, the section in which the elastic film linearly continues along the stretching and contracting direction has elasticity due to stretching and contracting of such a continued site. However, in a section in which the elastic film does not linearly continue along the stretching and contracting direction, the contraction force of the elastic film hardly acts on the first sheet layer and the second sheet layer, thus, elasticity is almost lost, and an elongation at an elastic limit approaches 100%. Therefore, it is possible to form the stretchable region and the non-stretchable region depending on the presence or absence of the section in which the elastic film does not linearly continue along the stretching and contracting direction.

Further, in such a non-stretchable region, the first sheet layer and the second sheet layer joined at the large number of sheet bond portions arranged at intervals, and the sheet bond portions are discontinuous. Thus, a decrease in the flexibility is prevented. In addition, in the non-stretchable region, continuity of the elastic film remains, an independent cut piece of the elastic film is not left, and a wrinkle is hardly formed. Thus, appearance is extremely excellent, and air permeability in the thickness direction by the through holes is ensured. Despite that, elasticity may be almost eliminated. In other words, according to the invention, it is possible to prevent degradation of appearance, prevent a decrease in flexibility, and improve non-elasticity in the non-stretchable region having the elastic film stretchable structure.

The absorbent article, wherein
across the whole non-stretchable region, the through holes penetrating the elastic film are disposed in a staggered shape,
a center-to-center interval of the adjacent two through holes in the stretching and contracting direction is shorter than a length of each of the through holes in the stretching and contracting direction, and
a center-to-center interval of the adjacent two through holes in a direction orthogonal to the stretching and contracting direction is shorter than a length of each of the through holes in the direction orthogonal to the stretching and contracting direction.

(Operational Advantage)

When the through holes are formed in the elastic film in an intermittent pattern, it is possible to substantially completely eliminate the linear continuity in the stretching and contracting direction while maintaining continuity of the elastic film, which is preferable. The term "center-to-center interval" refers to, when an object is not a point symmetry figure, an interval between a center of gravity to a center of gravity (the same applies hereinafter).

The absorbent article, wherein
a stretching stress of the elastic film is in a range of 4 to 12 N/35 mm when the elastic film is stretched four times in the stretching and contracting direction, and
in a state in which the non-stretchable region is stretched to an elastic limit in the stretching and contracting direction, the center-to-center interval of the adjacent two through holes in the stretching and contracting direction is in a range of 0.7 to 3.0 mm, the length of each of the through holes in the stretching and contracting direction is in a range of 1.0 to 4.5 mm, the center-to-center interval of the adjacent two through holes in the direction orthogonal to the stretching and contracting direction is in a range of 1.2 to 5.25 mm, and the length of each of the through holes in the direction orthogonal to the stretching and contracting direction is in a range of 0.7 to 3.0 mm.

(Operational Advantage)

When the elastic film within the range described is used, in the non-stretchable region, dimensions of each through hole and an arrangement interval of the through holes are preferably within the ranges as described. In a state in which the non-stretchable region is stretched to an elastic limit in the stretching and contracting direction (in other words, in a state in which the first sheet layer and the second sheet layer are fully spread), the center-to-center interval of the adjacent two through holes in the stretching and contracting direction is equal to a center-to-center interval of the adjacent two sheet joint portions in the stretching and contracting direction, the center-to-center interval of the adjacent two through holes in the direction orthogonal to the stretching and contracting direction is equal to the center-to-center interval of the adjacent two sheet bond portions in the direction orthogonal to the stretching and contracting direction, and the length of the through holes in the direction orthogonal to the stretching and contracting direction is equal to the length of the sheet bond portions in the direction orthogonal to the stretching and contracting direction.

The absorbent article, wherein
in the non-stretchable region, the first sheet layer is not and the second sheet layer is not joined to the elastic film in a portion other than between the first sheet layer and the second sheet layer in the sheet bond portions, and in a natural length state, a gap is provided, which is generated so as to contain both side portions of each of the sheet bond portions in the stretching and contracting direction by a peripheral edge of each of the through holes of the elastic film and each of the sheet bond portions separated from each other.

(Operational Advantage)

When such a gap is formed in the non-stretchable region, air permeability is imparted due to the gap even when a material of the elastic film is a non-porous film or a sheet, which is preferable.

The absorbent article, wherein
in the stretchable region, an elongation at an elastic limit in the stretching and contracting direction is set to 200% or more, and
in the non-stretchable region, an elongation at an elastic limit in the stretching and contracting direction is set to 120% or less.

(Operational Advantage)

The elongations at the elastic limits in the stretchable region and the non-stretchable region may be appropriately determined. However, the elongations at the elastic limits are preferably within the ranges as described.

The absorbent article, wherein
the absorbent article is an underpants-type disposable diaper having
an outer body included in a front body and a back body,
an inner body that is fixed to the outer body and includes an absorber, wherein
both side portions of the front body of the outer body are respectively joined to both side portions of the back body of the outer body to define side seal portions, and an annular torso region, a waist opening, and a pair of right and left leg openings are thereby formed,
the torso region of the outer body in at least one of the front body and the back body includes an absorber region defined as a front-back direction range overlapping the absorber, the elastic film stretchable structure is disposed across a width direction range at least of the absorber region corresponding to a range between both the side seal portions such that the stretching and contracting direction of the elastic film stretchable structure corresponds to a width direction thereof, and in the absorber region, the non-stretchable region is defined as an intermediate portion of the absorber region in the width direction, and the stretchable region is defined as a width direction range corresponding to a range between the non-stretchable region and the side seal portion.

(Operational Advantage)

It is unnecessary to impart elasticity to a portion of the outer body of the underpants-type disposable diaper which is overlapping the absorber even though the elastic film is desirably disposed on the portion due to a manufacturing reason. Therefore, it is preferable to form the non-stretchable region having a display portion, including the portion overlapping the absorber.

The absorbent article, wherein the elastic film stretchable structure is not extended to the waist end portion region, and a whole width direction range corresponding to a range between both the side seal portions of the waist end portion region contracts in the width direction by a contraction force of an elongated waist end portion elastic member attached to the whole width direction range along the width direction while it is possible that the whole width direction range corresponding to the range between the side seal portions of the waist end portion region is stretched in the width direction.

(Operational Advantage)

It is possible to provide a stretchable structure according to a conventional elongated elastically stretchable member as necessary without providing the elastic film stretchable structure in the waist end portion region in a case in which tightening of the waist end portion region is insufficient even with the elastic film stretchable structure used in the waist end portion region, etc.

An absorbent article comprising an elastic film stretchable structure formed by stacking an elastic film between a first sheet layer and a second sheet layer, wherein a region having the elastic film stretchable structure includes a stretchable region stretchable at least in one direction and a non-stretchable region being provided at least at one side of the stretchable region in a stretching and contracting direction and having an elongation at an elastic limit in the stretching and contracting direction of 130% or less, in the stretchable region, in a state in which the elastic film is stretched in the stretching and contracting direction, the first sheet layer and the second sheet layer are directly or indirectly joined at a large number of sheet bond portions arranged at intervals in each of the stretching and contracting direction and a direction orthogonal thereto, in the non-stretchable region, the first sheet layer and the second sheet layer are joined by welding at sheet bond portions provided in a row extending in a dotted line in a direction intersecting the stretching and contracting direction or in a plurality of rows, each of which is extending in a dotted line in a direction intersecting the stretching and contracting direction, and which are extending in dotted lines disposed at intervals in the stretching and contracting direction, the elastic film is cut along the row of the sheet bond portions, and both side portions of a cut position of the elastic film are left at both sides of the row of the sheet bond portions in the stretching and contracting direction in a natural length state, and a cut portion of the elastic film is formed by fracture of perforation formed by melting on the elastic film.

(Operational Advantage)

As an approach to eliminate the elasticity of the elastic film stretchable structure, it has been found that elasticity may be substantially eliminated by increasing the area rate of the sheet bond portions (per unit area) to some extent or more. However, to this end, the area rate of the sheet bond portions needs to be significantly increased, and hardening of touch may not be avoided.

In the non-stretchable region of the invention, the first sheet layer and the second sheet layer are joined by welding at sheet bond portions provided in a row extending in a dotted line in a direction intersecting the stretching and contracting direction or in a plurality of rows extending in dotted lines in a direction intersecting the stretching and contracting direction and disposed at intervals in the stretching and contracting direction. Therefore, even though the first sheet layer and the second sheet layer are integrated by welding at the sheet bond portions, since the sheet bond portions are discontinuous, a decrease in flexibility is prevented. Meanwhile, the elastic film is cut along the rows of the sheet joint portions, and both side portions of a cut position of the elastic film are left at both sides of the rows of the sheet joint portions in the stretching and contracting direction in a natural length state. Therefore, in the non-stretchable region, the elasticity of the elastic film is reliably eliminated and the elastic film is discontinuous, resulting in high air permeability. Further, the cut portion of the elastic film is formed by fracture of perforation formed by melting on the elastic film. That is to say, since the cut portion resulting from melting is discontinuous, a trace of cutting resulting from melting is discontinuous. Therefore, appearance is excellent, and a decrease in flexibility may be prevented.

The absorbent article, wherein in the non-stretchable region, the plurality of rows of the sheet bond portions is provided at intervals in the stretching and contracting direction, the both side portions of the cut positions of the elastic film are left as cut pieces in the natural length state so as to cross every other row in the rows of the sheet bond portions in the stretching and contracting direction, and the first sheet layer and the second sheet layer are joined via through holes provided in the cut pieces of the elastic film at sites of the rows of the sheet bond portions.

(Operational Advantage)

According to such a structure, since the cut pieces of the elastic film are fixed by joining the first sheet layer and the second sheet layer, the cut piece may be prevented from moving to degrade appearance or wearing feeling.

The absorbent article, wherein the absorbent article is an underpants-type disposable diaper having an outer body included in a front body and a back body, an inner body that is fixed to an internal surface of the outer body and includes an absorber, wherein both side portions of the front body of the outer body are respectively joined to both side portions of the back body of the outer body to define side seal portions, and an annular torso region, a waist opening, and a pair of right and left leg openings are thereby formed, the outer body in at least one of the front body and the back body includes the elastic film stretchable structure disposed across a width direction range corresponding to a range between both the side seal portions at least in a part of a front-back direction range of the side seal portion such that the stretching and contracting direction of the elastic film stretchable structure corresponds to a width direction, and a region including the elastic film stretchable structure has the non-stretchable region in a region overlapping the absorber, and the stretchable regions at both sides of the non-stretchable region in the width direction.

(Operational Advantage)

The underpants-type disposable diaper has the stretchable region and the non-stretchable region in a large area, and thus is particularly suitable for the invention.

A method of manufacturing an absorbent article comprising an elastic film stretchable structure formed by stacking an elastic film between a first sheet layer and a second sheet layer, wherein a region including the elastic film stretchable structure has a stretchable region stretchable at least in one direction and a non-stretchable region being provided at least at one side of the stretchable region in a stretching and contracting direction and having an elongation at an elastic limit in the stretching and contracting direction of 130% or less, the method comprising in forming the elastic film stretchable structure, in a state the elastic film is stacked between the first sheet layer and the second sheet layer while the elastic film is stretched in an MD (Machine Direction), in the stretchable region, forming sheet bond portions by joining the first sheet layer and the second sheet layer at a large number of positions arranged at intervals in each of the MD and a CD (Cross Direction) orthogonal to the MD, and in the non-stretchable region, performing a welding process in a welding pattern of one row extending in a dotted line in the CD or a plurality of rows, each of which is extending in a dotted line in the CD, and which are disposed at intervals in the MD, to melt the elastic film in the welding pattern of the dotted line, thereby forming perforation, joining the first sheet layer and the second sheet layer via through holes of the perforation to form sheet bond portions, and then fracturing the perforation by a tensile force applied by stretching of the elastic film.

(Operational Advantage)

As stated above, in the non-stretchable region, the perforation resulting from melting is formed in the elastic film by performing the welding process in the welding pattern of the one row or the plurality of rows, each of which is extending in a dotted line in the CD, and which are disposed at intervals in the MD, in the state in which the elastic film is stacked between the first sheet layer and the second sheet layer while the elastic film is stretched at least in the MD, and at the same time, the first sheet layer and the second sheet layer are joined via the through holes of the perforation, and further, the perforation is fractured by the tensile force applied by stretching the elastic film. Therefore, it is possible to significantly simply and efficiently form the non-stretchable region described in claim 1.

The method of manufacturing an absorbent article, wherein in the non-stretchable region, the welding process is set to perform in the welding pattern of the plurality of rows disposed at intervals in the MD, the perforation is formed in a welding pattern of the rows, each of which is extending in the dotted line, and which are located every other row in the MD, and is fractured by the tensile force applied by stretching of the elastic film, and cut pieces of the elastic film are left in a natural length state so as to cross the remained rows in a welding pattern of the rows, each of which is extending in the dotted line, and the remained rows locating every other row of the sheet bond portions.

(Operational Advantage)

It is possible to significantly simply and efficiently form the non-stretchable region described in claim 2.

The method of manufacturing an absorbent article, wherein the elastic film is an elastic film having a tensile strength in the MD of 8 to 25 N/35 mm, a tensile strength in the CD of 5 to 20 N/35 mm, a tensile elongation in the MD of 450 to 1,050%, and a tensile elongation in the CD of 450 to 1,400%, and in performing the welding process, the welding pattern of the row extending in the dotted line is set to a pattern having an interval in the CD between the two adjacent welding points of 1 mm or less, and the elastic film is put in a state in which the same is stretched 2 to 5 times in the MD.

(Operational Advantage)

The elastic film is not particularly restricted. However, an elastic film having the above-described characteristic is preferable. In this case, in performing the welding process, the welding pattern and to the number of times in the length the elastic film is stretched are preferably in the above-described ranges for reliable fracture of the perforation of the elastic film.

The method of manufacturing an absorbent article, wherein the welding process is performed by a welding process device on a production line while the first sheet layer, the second sheet layer, and the elastic film are continuously conveyed on the production line, and the welding pattern of the dotted line is set to have a section in which the interval in the CD between the two adjacent welding points is a first interval, and a section in which the interval in the CD between the two adjacent welding points is a second interval being larger than the first interval.

(Operational Advantage)

When the welding pattern of the dotted line described above is adopted, ties of perforation (tying portions each of which is provided between the two adjacent through holes) formed in the elastic film become ties each having the same length as that of the first interval and ties each having the same length as that of the second interval. When the perforation is fractured by the tensile force applied by stretching the elastic film, the ties each having the same length as that of the first interval are first fractured, and then the ties each having the same length as that of the second interval are fractured. Accordingly, it is possible to increase time taken from the welding process to fracturing the whole of the perforation of the elastic film. Therefore, a situation can be prevented in which the perforation of the elastic film is fractured almost at the same time that the welding process is performed and thus the elastic film cannot be continuously conveyed.

An absorbent article comprising an elastic film stretchable structure in which an elastic film is stacked between a first sheet layer and a second sheet layer, in a state in which the elastic film is stretched in the stretching and contracting direction along surfaces of the first sheet layer and the second sheet layer, the first sheet layer and the second sheet layer are joined via through holes formed in the elastic film at a large number of sheet bond portions arranged at intervals in each of a stretching and contracting direction and a direction orthogonal thereto, wherein a region including the elastic film stretchable structure has a non-stretchable region and a stretchable region being provided at least at one side of the non-stretchable region in the stretching and contracting direction and being stretchable in the stretching and contracting direction, and in the non-stretchable region, an area rate of the sheet bond portions in the non-stretchable region is higher than that in the stretchable region and elasticity of the elastic film at a part or total of a portion formed among the through holes is decreased due to thermal deterioration, thereby an elongation at an elastic limit is set to 130% or less in the stretching and contracting direction.

(Operational Advantage)

Through examination of approaches to eliminate the elasticity of the elastic film stretchable structure, in a method of performing welding at a large number of positions arranged at intervals in each of the stretching and contracting direction and the direction orthogonal thereto in a state in which the elastic film is interposed between the first sheet layer and the second sheet layer while the elastic film is stretched in the stretching and contracting direction of the stretchable region to melt the elastic film at the plurality of positions, thereby forming the through holes, as well as joining the first sheet layer and the second sheet layer at positions of the through holes for forming the elastic film stretchable structure, it has been found that the elasticity can be substantially eliminated by making the area rate (per unit area) of the sheet joint portions to be higher than a certain level. That is to say, in such an elastic film stretchable structure, basically, the larger the area rate of the sheet joint portions is, the smaller area of a portion formed among the through holes is, since in each of the portions, the first sheet layer and the second sheet layer contract by the elastic film. Thus, the elongation at the elastic limit tends to decrease. Further, when the area rate of the sheet joint portions is higher than or equal to a certain level, elasticity is substantially lost, and non-elasticity is obtained since the elongation at the elastic limit decreases, as well as the most of the portion formed among the through holes of the elastic film deteriorates due to heat generated in the welding. Therefore, according to the invention, while the elasticity is substantially eliminated, continuity of the elastic film in the stretchable region and the non-stretchable region can be maintained and can produce an absorbent article having a good appearance.

The absorbent article, wherein the absorbent article is an underpants-type disposable diaper having an outer body included in a front body and a back body, an inner body that is fixed to an internal surface of the outer body and includes an absorber, wherein both side portions of the front body of the outer body are respectively joined to both side portions of the back body of the outer body to define side seal portions, and an annular torso region, a waist opening, and a pair of right and left leg openings are thereby formed, the outer body in at least one of the front body and the back body includes the elastic film stretchable structure disposed across a width direction range corresponding to a range between both the side seal portions at least in a part of a front-back direction range of the side seal portion such that the stretching and contracting direction of the elastic film stretchable structure corresponds to a width direction, and a region including the elastic film stretchable structure has the non-stretchable region in a region overlapping the absorber, and the stretchable regions at both sides of the non-stretchable region in the width direction.

(Operational Advantage)

The invention is particularly suitable for the underpants-type disposable diaper.

A method of manufacturing an absorbent article comprising an elastic film stretchable structure in which an elastic film is stacked between a first sheet layer and a second sheet layer, and in a state in which the elastic film is stretched in the stretching and contracting direction along surfaces of the first sheet layer and the second sheet layer, the first sheet layer and the second sheet layer are joined via through holes formed in the elastic film at a large number of sheet bond portions arranged at intervals in each of a stretching and contracting direction and a direction orthogonal thereto, wherein a region including the elastic film stretchable structure has a non-stretchable region and a stretchable region being provided at least at one side of the non-stretchable region in a stretching and contracting direction and being stretchable in the stretching and contracting direction, and the method comprising:

in forming the elastic film stretchable structure, in a state in which the elastic film is stacked between the first sheet layer and the second sheet layer while the elastic film is stretched in an MD (Machine Direction), welding the first sheet layer and the second sheet layer at a large number of positions arranged at intervals in each of the MD and a CD (Cross Direction) orthogonal to the MD, and melting the elastic film at the large number of positions so as to form through holes, joining the first sheet layer and the second sheet layer at least by solidification of a melted material of the elastic film at positions of the through holes; and in the non-stretchable region, in the welding, making an area rate of the sheet bond portions in the non-stretchable region to be higher than in the stretchable region, and transferring heat generated in the welding to a part or total of a portion formed among the through holes in the elastic film to degrade the part or total of the portion formed among the through holes using the heat generated in the welding to decrease elasticity.

(Operational Advantage)

When welding is performed by heat sealing, ultrasonic sealing, etc. in an arrangement pattern of the sheet joint portions in a state in which the elastic film is interposed between the first sheet layer and the second sheet layer as described above, the through holes of the elastic film can be formed in any one of the stretchable region and the non-stretchable region, as well as the first sheet layer and the second sheet layer can be joined by solidification of the melted material of the elastic film via the through holes. Furthermore, since the area rate of the sheet joint portions in the non-stretchable region is higher than that in the stretchable region, simultaneously with formation of the through holes and the sheet joint portions, heat generated in the welding can be transferred to the part or whole of the portion formed among the through holes in the elastic film to degrade the part or whole of the portion formed among the through holes by the heat generated in the welding, thereby decreasing elasticity. Therefore, it is possible to significantly simply and efficiently manufacture the elastic film stretchable structure having the stretchable region and the non-stretchable region. In addition, the manufactured stretchable region achieves both high air permeability and high peeling strength.

The method of manufacturing an absorbent article, wherein the welding corresponds to ultrasonic welding, an area of each of the sheet joint portions in the non-stretchable region is in a range of 0.14 to 0.75 mm$^2$, and an area rate of the sheet bond portions in the non-stretchable region is in a range of 8 to 17%.

(Operational Advantage)

As described above, in a case in which, the ultrasonic welding is used in order to form the through holes and the sheet joint portions, and the heat generated in the welding is used in order to decrease elasticity of the non-stretchable region, under a condition that a speed of a production line is low (about 30 m/min), ultrasonic vibration is easily transferred, and a sufficient thermal deterioration area of the elastic film may be ensured by increasing the area of each of the sheet joint portions in the non-stretchable region to some extent. However, under a condition that the speed of the production line is high (about 120 m/min), there is a concern that welding of the sheet joint portions may be insufficient as long as the area of each of the sheet joint portions is not decreased to some extent. Nevertheless, if the area of each of the sheet joint portions is decreased just for sufficient welding of the sheet joint portions, there is a concern that the thermal deterioration area of the elastic film may be insufficient for obtaining non-stretching. On the other hand, when the ultrasonic welding is performed by densely disposing small sheet joint portions at narrow intervals as described above, there is little concern about insufficient welding. Further, even though the thermal deterioration area of the elastic film is small, an interval of the adjacent two through holes narrows, and thus non-stretching is sufficiently obtained.

The method of manufacturing an absorbent article, wherein a shape of each of the sheet bond portions is a shape which is elongated in the MD.

(Operational Advantage)

when the shape of each of the sheet joint portions, that is, a shape of each of the welding portion in a welding pattern in the ultrasonic welding is the shape that is elongated in the MD as described above, it is possible to widen the thermal deterioration area of the elastic film when compared with an isotropic shape having the same area, as well as an area in which the ultrasonic vibration is applied does not increase. Thus, there is an advantage that welding of the sheet bond portions is less likely to be insufficient.

An absorbent article having an absorber that absorbs excrement, the absorbent article comprising an elastic film stretchable structure in which an elastic film is stacked between a first sheet layer and a second sheet layer, wherein a region having the elastic film stretchable structure includes a non-stretchable region and a stretchable region provided at least at one side of the stretchable region in a stretching and contracting direction and being stretchable in the stretching and contracting direction, in the stretchable region, in a state in which the elastic film is stretched in the stretching and contracting direction along surfaces of the first sheet layer and the second sheet layer, an elongation at an elastic limit in the stretching and contracting direction is set to 200% or more by directly or indirectly joining the first sheet layer and the second sheet layer at a large number of sheet bond portions arranged at intervals in each of the stretching and contracting direction and a direction orthogonal thereto, and in the non-stretchable region, in a state in which the elastic film is stretched in the stretching and contracting direction along the surfaces of the first sheet layer and the second sheet layer, an elongation at an elastic limit is set to 130% or less by directly or indirectly joining the first sheet layer and the second sheet layer at a large number of sheet bond portions arranged at intervals in each of the stretching and contracting direction and the direction orthogonal thereto and at least one of by an area rate of the sheet bond portions in the non-stretchable region being higher than that in the stretchable region; the elastic film being melted; and the elastic film being finely divided at least in the stretching and contracting direction.

(Operational Advantage)

In the elastic film stretchable structure in the invention, when the first sheet layer and the second sheet layer are joined directly or indirectly at a large number of sheet bond portions arranged at intervals in each of the stretching and contracting direction and the direction orthogonal thereto in a state in which the elastic film is stretched in the stretching and contracting direction along surfaces of the first sheet layer and the second sheet layer, basically, as the area rate of the sheet bond portions increases, portions in which the first sheet layer and the second sheet layer contract by the elastic film decrease Thus, the elongation at the elastic limit tends to decrease. Therefore, the non-stretchable region and the stretchable region may be formed only by changing the area rate of the sheet bond portions.

In addition, the non-stretchable region may be formed by heating and melting the elastic film or by the elastic film being finely divided at least in the stretching and contracting direction.

The absorbent article, wherein a display portion composed of the sheet bond portions formed by directly or indirectly joining the first sheet layer and the second sheet layer is included in middle in the direction orthogonal to the stretching and contracting direction, and the stretchable region is not included at both sides of the non-stretchable region in the direction orthogonal to the stretching and contracting direction.

(Operational Advantage)

The inventor has found that displays known in the field of absorbent articles, for example, decorative patterns, such as small illustrations and characters, functional indicators indicating usage instructions, usage guides, and sizes, and marks indicating manufacturers, product names, and distinctive functions, etc. may be applied to the region having the stretchable structure by arranging dot-shaped sheet bond portions in a display manner or by forming the sheet bond portion in a shape of the display manner in a research process of such an elastic film stretchable structure. An approach to apply the display is allowed since the elastic film is continuously present in the elastic film stretchable structure unlike a conventional stretchable structure using rubber thread, so that arrangement and a shape of the sheet bond portions have some extent of freedom.

However, when such a display is provided in the stretchable region, the display (sheet bond portions) may be hidden in a contraction wrinkle, or a relative position changes due to stretching or contracting of the stretchable region, and thus problems are caused with the appearance depending on the content of the display and the purpose of display. To solve these problems, it has been considered that elasticity of a display formation region is eliminated to use the region as the non-stretchable region, and a display is provided in this non-stretchable region. However, when the stretchable region is provided adjacent to the non-stretchable region in the direction orthogonal to the stretching and contracting direction, a wrinkle or a pleat is formed in the non-stretchable region due to an influence of contraction of the stretchable region, and appearance of the display deteriorates.

In this regard, the invention as described proposes improvement in appearance when a display including the sheet bond portions is applied to the elastic film stretchable structure. In more detail, in a case in which the non-stretchable region is formed in the elastic film stretchable structure, and the display composed of the sheet bond portions is applied thereto, when a configuration in which the stretchable region according to the elastic film stretchable structure is not present at both sides of the non-stretchable region in the direction orthogonal to the stretching and contracting direction is adopted, and a display portion composed of the sheet bond portions is disposed in the middle part in the direction orthogonal to the stretching and contracting direction as described above, the display portion is hardly affected by contraction of the stretchable region, and deterioration of appearance of the display is prevented.

The absorbent article, wherein the sheet bond portions are formed by welding materials of the first sheet layer and the second sheet layer.

(Operational Advantage)

A method of forming the sheet bond portions is not particularly restricted. However, when the sheet bond portions are formed by the welding process, appearance of the sheet bond portions is different from a surrounding appearance. Thus, the display portion is highlighted.

The absorbent article, wherein the first sheet layer and the second sheet layer are joined via through portions formed in an elastic sheet layer at the sheet bond portions, and the first sheet layer is not and the second sheet layer is not joined to the elastic film in a portion other than between the first sheet layer and the second sheet layer in the sheet bond portions.

(Operational Advantage)

When such a structure is adopted, it is preferable that since a gap is formed by each through portion of the elastic sheet layer and each sheet bond portion, even if the elastic film layer is composed of a nonporous material, the gap contributes to air permeability.

The absorbent article, wherein in the non-stretchable region, the area rate of the sheet bond portions is higher than that in the stretchable region so that an elongation at an elastic limit in the stretching and contracting direction is set to 130% or less, an area of each of the sheet bond portions is in a range of 0.14 to 3.5 mm$^2$, in the non-stretchable region, the area rate of the sheet bond portions is in a range of 16 to 45%, and in the stretchable region, the area rate of the sheet bond portions is in a range of 1.8 to 22.5%.

(Operational Advantage)

The area of each of the sheet bond portions and the area rate of sheet bond portions may be appropriately determined. However, in general, the above ranges are desirable.

The absorbent article, wherein the absorbent article is an underpants-type disposable diaper having an outer body included in front body and a back body, an inner body that is fixed to an internal surface of the outer body and includes an absorber, wherein both side portions of the front body of the outer body are respectively joined to both side portions of the back body of the outer body to define side seal portions, and an annular torso region, a waist opening, and a pair of right and left leg openings are thereby formed, the outer body in at least one of the front body and the back body includes the elastic film stretchable structure disposed across a width direction range corresponding to a range between both the side seal portions at least in a part of a front-back direction range of the side seal portion such that the stretching and contracting direction of the elastic film stretchable structure corresponds to a width direction, and a region including the elastic film stretchable structure has the non-stretchable region and the stretchable region.

(Operational Advantage)

Particularly in each of the underpants-type disposable diapers among the absorbent articles, the stretchable region is large, and there are a lot of modes used in place of underwear. Thus, a display such as a pattern is applied in many cases, and appearance is important. To provide such a display, conventionally, it has been common to interpose a sheet on which an indication is printed between an inner body and an outer body or inside the outer body. However, according to the invention, it is possible to apply a display having an excellent appearance while omitting such a printed sheet.

The absorbent article, wherein the outer body in at least one of the front body and the back body includes a torso intermediate region defined as a front-back direction range between a waist end portion region and the absorber, and the elastic film stretchable structure is provided across a width direction range corresponding to the range between both the side seal portions at least in the torso intermediate region such that the stretching and contracting direction thereof corresponds to the width direction, and the torso intermediate region is set to include in an intermediate portion in the width direction, the non-stretchable region having the display portion, and the stretchable region in a width direction range corresponding to a range between the non-stretchable region and the side seal portion.

(Operational Advantage)

The torso intermediate region is a region not having the absorber, and is soft unlike a region having elasticity such as a region having the absorber. Thus, the display portion is easily affected by contraction of the stretchable region. Therefore, the invention particularly has a technical meaning when the display portion is provided in the torso intermediate region.

The absorbent article, wherein the torso region of the outer body included at least in one of the front body and the back body includes an absorber region overlapping the absorber, and the elastic film stretchable structure disposed across a whole of the width direction at least of a region from the torso intermediate region to the absorber region such that the stretching and contracting direction of the elastic film stretchable structure corresponds to a width direction, and the region from the torso intermediate region to the absorber region is set to have the non-stretchable region having the display portion in an intermediate portion in the width direction thereof, and the stretchable region at a width direction range corresponding to a range between the non-stretchable region and the side seal portion.

(Operational Advantage)

It is unnecessary to impart elasticity to a portion of the outer body of the underpants-type disposable diaper which is overlapping the absorber even though the elastic film is desirably disposed on the portion due to a manufacturing reason. Therefore, it is preferable to form the non-stretchable region having the display portion, including the portion overlapping the absorber.

The absorbent article, wherein the elastic film stretchable structure is extended to the waist end portion region, and another stretchable structure stretchable in a width direction is not provided at the front and back of the non-stretchable region.

(Operational Advantage)

When the elastic film stretchable structure is extended to the waist end portion region, and another stretchable structure stretchable in a width direction is not included as described above, it is possible to omit the conventional elongated waist end portion elastic member which has been conventionally provided in the waist end portion region, etc., and an influence of contraction of the stretchable region on the non-stretchable region is completely prevented, which is preferable.

The absorbent article, wherein a whole width direction range corresponding to a range between the both side seal portions in the waist end portion region is set to the stretchable region in which an elongated waist end portion elastic member is fixed in a stretched state along the width direction.

(Operational Advantage)

It is possible to provide a stretchable structure according to a conventional elongated elastically stretchable member without providing the elastic film stretchable structure in the waist end portion region as necessary in a case in which tightening of the waist end portion region is insufficient even with the elastic film stretchable structure used in the waist end portion region, etc.

The absorbent article, wherein in the waist end portion region, a width direction range corresponding to the stretchable region in a region having the elastic film stretchable structure is set to a stretchable region in which an elongated waist end portion elastic member is fixed in a stretched state along the width direction, and in the waist end portion region, a width direction range corresponding at least to the display portion is set to a non-stretchable region or a weak stretchable region in which an elongation at an elastic limit is smaller than that of the stretchable region in the waist end portion region.

(Operational Advantage)

It is possible to provide a stretchable structure according to a conventional elongated elastically stretchable member without providing the elastic film stretchable structure in the waist end portion region as necessary in a case in which tightening of the waist end portion region is insufficient even with the elastic film stretchable structure used in the waist end portion region, etc. However, in this case, when the display portion is provided near the waist end portion region, even though the display portion is located in the middle part in the direction orthogonal to the stretching and contracting direction of the non-stretchable region, the display portion is likely to be affected by stretching and contraction of the waist end portion region. Therefore, when the stretchable structure according to the elongated elastically stretchable member is provided, it is also preferable that at least the width direction range corresponding to the display portion is set to the non-stretchable region or the weak stretchable region as described above.

The absorbent article, wherein the non-stretchable region is set to have any one of (a) a shape in which a width becomes smaller continuously or stepwise as progressing toward a waist opening side from a crotch side, (b) a shape in which the width becomes larger continuously or stepwise as progressing toward the waist opening side from the crotch side, and (c) a shape in which the width becomes once larger and after that becomes smaller continuously or stepwise as progressing toward the waist opening side from the crotch side.

(Operational Advantage)

When the shape of the non-stretchable region is set to the above-described shape, the outer body can have a shape with high fitting property with respect to a body surface, which is preferable.

The absorbent article, wherein the non-stretchable region has a shape branched into a plurality of parts as progressing toward a waist opening side from a crotch side, and the stretchable region is provided between the two adjacent branched parts of the non-stretchable region.

(Operational Advantage)

When the shape of the non-stretchable region is set to such a branched shape, it is possible to provide the display portion based on the non-stretchable region while preventing the outer body from hardening.

Advantageous Effects of Invention

As described above, according to the invention, there is an advantage in that an excellent non-stretchable region may be formed in an elastic film stretchable structure, etc.

BRIEF DESCRIPTION OF DRAWINGS

FIG. 4A is a C-C cross-sectional view of FIG. 1 and FIG. 42, and FIG. 4B is an E-E cross-sectional view of FIG. 1 and FIG. 42.

FIG. 6 is a B-B cross-sectional view of FIG. 1.

DESCRIPTION OF EMBODIMENTS

Figure 1:
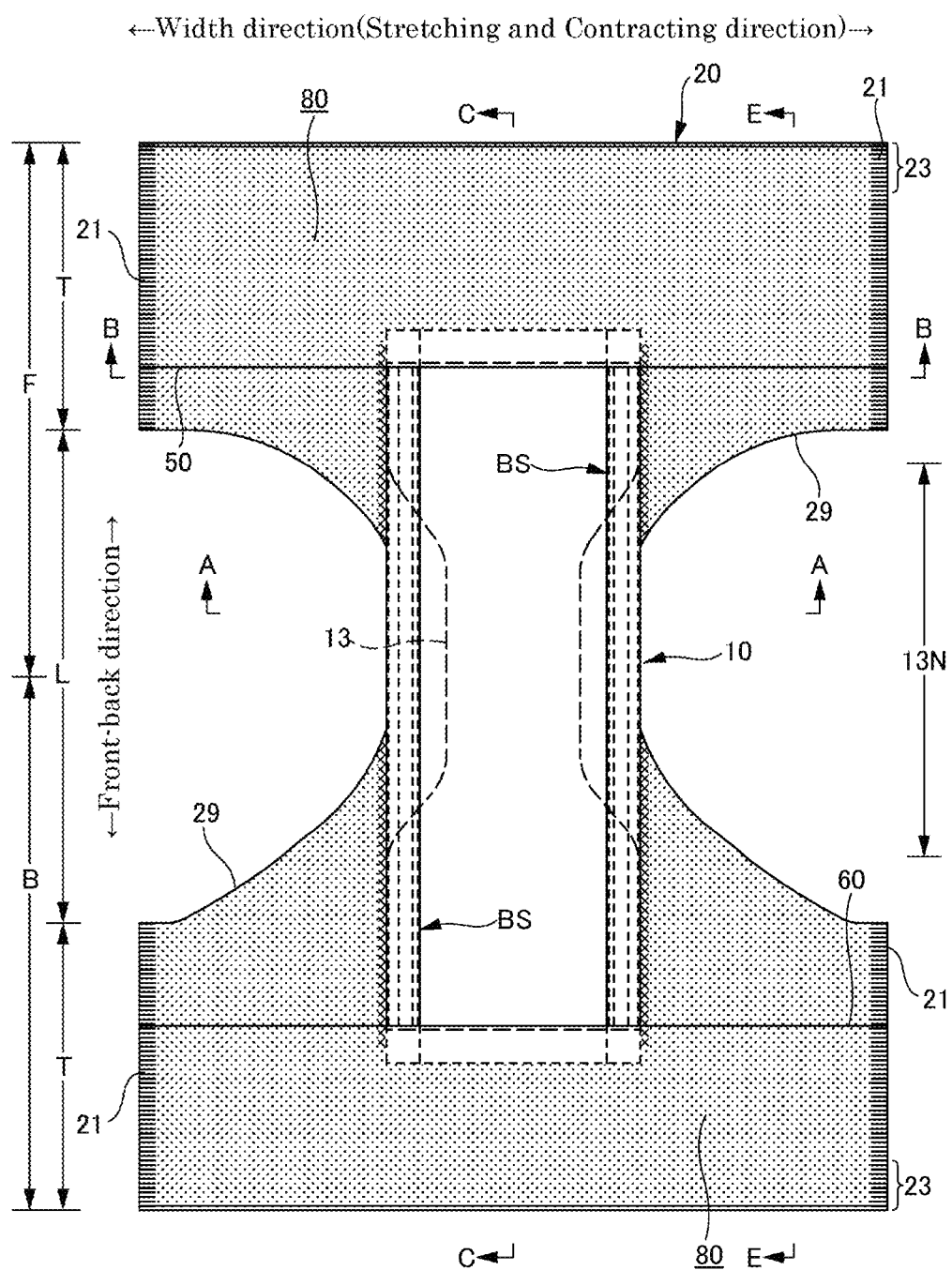
FIG. 1 is a plan view (internal surface side) of an underpants-type disposable diaper in the spread state.

Hereinafter, an embodiment of the invention will be described with reference to accompanying drawings. A dotted portion in a cross-sectional view indicates joining means such as a hot-melt adhesive.

<With Regard to Common Matters>

FIG. 1 to FIG. 6 illustrate an underpants-type disposable diaper. This underpants-type disposable diaper (hereinafter also simply referred to as a diaper) has an outer body 20 included in a front body F and a back body B as one unit, an inner body 10 that is fixed to the internal surface of the outer body 20 as one unit. Further, in the inner body 10, an absorber 13 is interposed between a liquid pervious top sheet 11 and a liquid impervious sheet 12. In manufacturing, after a back surface of the inner body 10 is joined to the internal surface side (upper surface) of the outer body 20 using joining means such as a hot-melt adhesive, the inner body 10 and the outer body 20 are folded at a center in a front-back direction (vertical direction) corresponding to a boundary between the front body F and the back body B, and both side portions thereof are joined to each other by heat sealing, a hot-melt adhesive, etc. to form side seal portions 21, thereby obtaining an underpants-type disposable diaper in which a waist opening and a pair of right and left leg openings are formed.

(Exemplary Structure of Inner Body)

Figure 5:
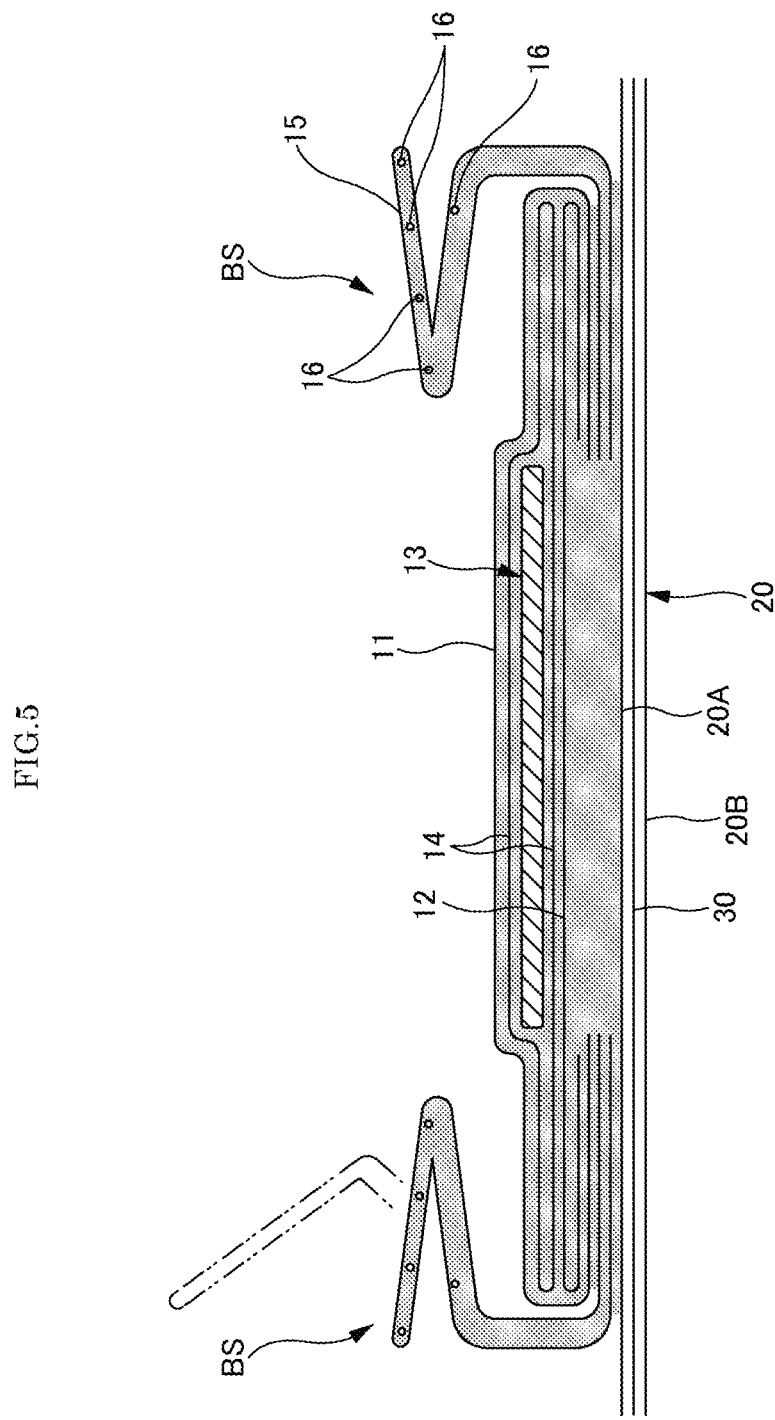
FIG. 5 is an A-A cross-sectional view of FIG. 1.

With reference to FIGS. 4 to 6, the inner body 10 includes a top sheet 11 composed of, for example, non-woven fabric, a liquid-impermeable sheet 12 composed of, for example, polyethylene, and an absorber 13 between the top sheet 11 and the liquid-impermeable sheet 12. The inner body 10 is configured to absorb and retain excretory fluid passing through the top sheet 11. The inner body 10 may have any planar shape and typically has a substantially rectangular shape as shown in the drawing.

The top sheet 11 that covers a front surface side (to come into contact with the skin) of the absorber 13 is preferably composed of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and cupra; and natural fibers, such as cotton. The nonwoven fabric can be produced by any process, for example, spun lacing, spun bonding, thermal bonding, melt blowing, or needle punching. Among these processes, preferred are spun lacing in view of flexibility and drape characteristics and thermal bonding in view of bulky soft products. A large number of through holes formed in the top sheet 11 facilitates absorption of urine and achieves dry touch characteristics. The top sheet 11 extends around the side edges of the absorber 13 and extends to the back surface side of the absorber 13.

The liquid-impermeable sheet 12, covering the back surface side (not in contact with skin) of the absorber 13 is composed of a liquid-impervious plastic sheet, for example, polyethylene sheet or polypropylene sheet. Recently, permeable films have been preferably used in view of preventing stuffiness. This water-block permeable sheet is a microporous sheet prepared through melt-kneading an olefin resin, for example, polyethylene resin or polypropylene resin, and inorganic filler, forming a sheet with the kneaded materials, and then uniaxially or biaxially elongating the sheet.

The absorber 13 may be composed of a well-known basic component, such as an accumulated body of pulp fibers, an assembly of filaments, composed of, for example, cellulose acetate, or non-woven fabric, and the absorber 13 may include as necessary high-absorbent polymer mixed or fixed to the basic component. The absorber 13 may be wrapped with a liquid-permeable and liquid-retainable package sheet 14, such as a crepe sheet, to retain the shape and polymers, as required.

The absorber 13 has a substantially hourglass shape having a narrow portion 13N with a width narrower than those of the front and back end portions of the absorber 13, at a crotch portion. Alternatively, the absorber 13 may have any other shape, for example, a rectangular shape, as appropriate. The size of the narrow portion 13N may be appropriately determined. The narrow portion 13N may have a length of approximately 20 to 50% of the entire length of the diaper along the front-back direction, and a width, at the narrowest region, of approximately 40 to 60% of the entire width of the absorber 13. If the inner body 10 has a substantially rectangular planar shape in the case of the absorber with such a narrower part 13N, the inner body 10 has portions free of the absorber 13 according to the narrower part 13N of the absorber 13.

Three-dimensional gathers BS, which are configured to fit around the legs, are formed on both side portions of the inner body 10. With reference to FIGS. 5 and 6, the three-dimensional gathers BS are each composed of a gather non-woven fabric 15 folded into a duplicate sheet consisting of a fixed section fixed to the side portion of the back surface of the inner body, a main section extending from the fixed section around a side portion of the inner body to the side portion of the front surface of the inner body, lying down sections formed by fixing the front end portion and back end portion of the main section in a lying down state to the side portion of the front surface of the inner body, and a free section formed in an un-fixed state between both the lying down sections.

Elongated gather elastic members 16 are disposed in the tip portion of the free sections of the duplicate sheet. As illustrated by the chain double-dashed line in FIG. 5, part of the non-woven fabric protruding from a side edge of the absorber is erected by elastic stretching force of the gather elastic members 16 to form a three-dimensional gather BS in a completed product.

The liquid impervious sheet 12 is folded back to the back surface side together with the top sheet 11 at both sides of the absorber 13 in the width direction. The liquid-impervious back surface sheet 12 is preferably opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 16 may be composed of commodity materials, for example, styrene rubber, olefin rubber, urethane rubber, ester rubber, polyurethanes, polyethylene, polystyrene, styrene-butadiene, silicones, and polyester. The gather elastic members 16 preferably have a fineness of 925 dtex or less and are disposed under a tension of 150% to 350% at an interval of 7.0 mm or less to be hidden from outside view. The gather elastic member 16 may have a string shape shown in the drawing or a tape shape with an appropriate width.

Like the top sheet 11, the gather nonwoven fabric 15 may be composed of raw fibers including synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. The gather nonwoven fabric 15 is preferably a water-repellent nonwoven fabric coated with a water repellent agent, for example, a silicone-based agent, a paraffin-metallic agent, or an alkyl chromic chloride agent to prevent penetration of urine and the like, to prevent diaper rash, and to enhance feeling to skin (dryness).

Figure 3:
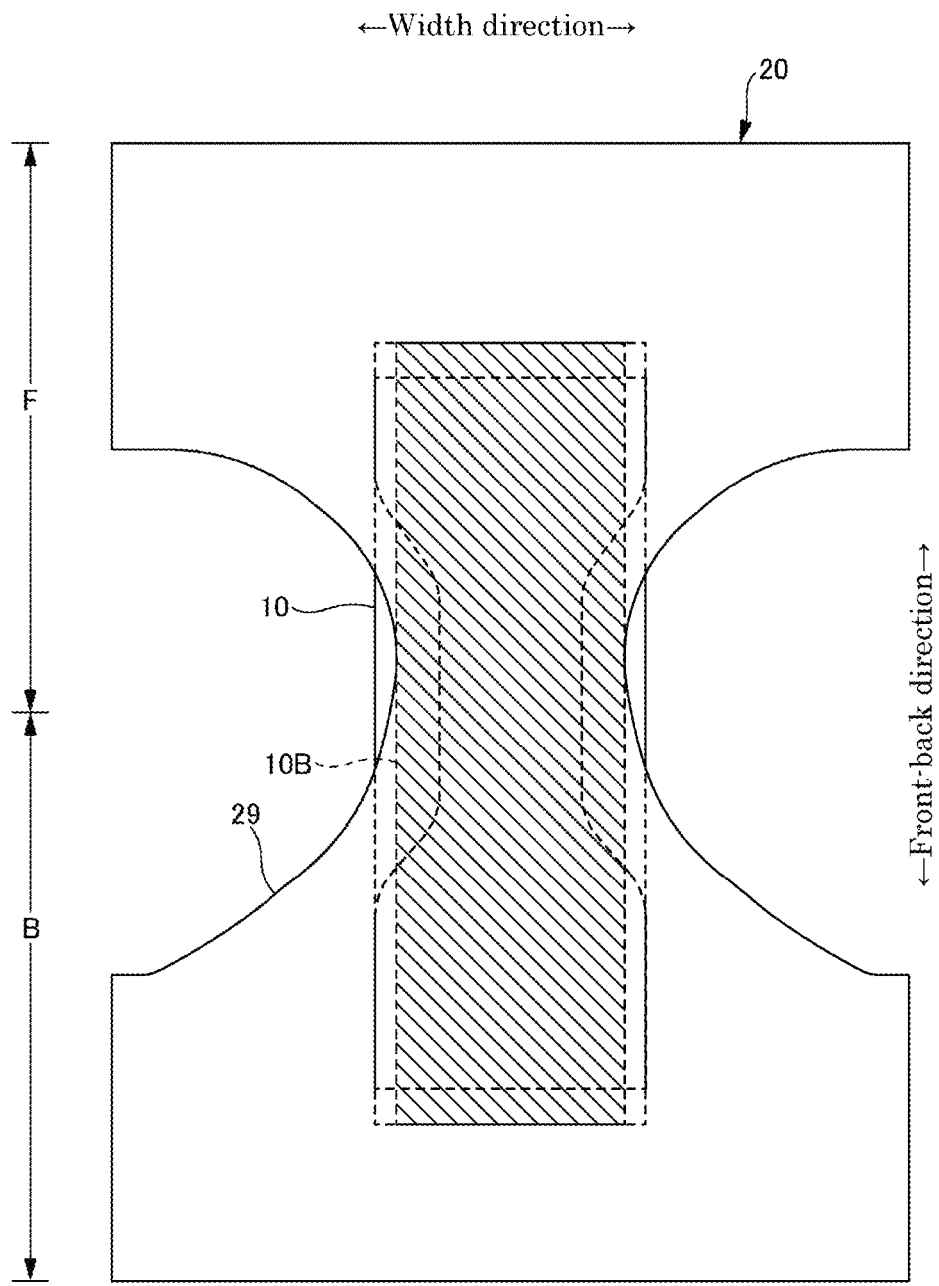
FIG. 3 is a plan view illustrating only a main part of the underpants-type disposable diaper in the spread state.

As illustrated in FIG. 3, the back surface of the inner body 10 is fixed to the internal surface of the outer body 20 by, for example, a hot-melt adhesive in an internal and external fixed region 10B (shaded area). The internal and external fixed region 10B extends over with a width from a side portion 17 free of the absorber at one side to another side portion 17 free of the absorber at the other side at the both front and back sides of the side portions 17. Side edges of the internal and external fixed region 10B are preferably positioned at lateral sides of middle of the side portions 17 free of the absorber in the width direction. In particular, the internal and external fixed region 10B is preferably fixed to the substantially whole inner body 10 in the width direction and fixed to the substantially whole outer body 20 in the front-back direction.

(Front and Back Cover Sheets)

With reference to FIG. 1 and FIG. 4, front and back cover sheets 50, 60 may be provided to cover the front and back end portions of the inner body 10 attached to the internal surface of the outer body 20 to prevent leakage from the front and rear edges of the inner body 10. In more detail, the front cover sheet 50 extends over the entire width of the front body F on the internal surface of the front body F from the internal surface of the folded part 20C at the waist side end of the front body F to a position overlapping with the front end portion of the inner body 10. The back cover sheet 60 extends on the internal surface of the back body Ba over the entire width, and extends over the entire width of the back body B from the internal surface of the folded part 20C at the waist side end of the back body B to a position overlapping with the back end portion of the inner body 10, in the embodiment illustrated in the drawings. Minor non-bonded regions are provided over the entire width (or only at the central portion) at side edge portions of the front and back cover sheets 50 and 60 at the crotch portion-side. The front and back cover sheets 50 and 60 having such non-bonded regions can prevent leakage of the adhesive and function as barriers against leakage when slightly suspended from the top sheet.

As shown in the embodiment illustrated in the drawings, the front and back cover sheets 50, 60 as separate components advantageously enlarge the range of choice of material, but disadvantageously needs additional materials and manufacturing processes. Thus, the folded part 20C formed by folding back the outer body 20 toward the inner surface side of the diaper are respectively extended to portions overlapping with the inner body 10, so as to have the same function as that of the cover sheets 50, 60.

<First Mode>

First, a first mode will be described based on FIG. 1 to FIG. 21. The outer body 20 is extended to a lateral side of the side edge of the absorber 13. To this extent, referring to the outer body 20, as in the illustrated mode, a side edge of the outer body 20 may be positioned at a central side of a side edge of the inner body 10 in the width direction or at an outer side thereof in the width direction in the crotch portion. In addition, the outer body 20 has a torso region T corresponding to a front-back direction range of each side seal portion 21, and an intermediate region L corresponding to a front-back direction range between the torso region T of the front body F and the torso region T of the back body B. Further, in the outer body 20 of the illustrated mode, except for the middle of the intermediate region L in the front-back direction, an elastic film 30 is stacked between a first sheet layer 20A and a second sheet layer 20B as illustrated in FIG. 2 and FIG. 4 to FIG. 6, and the first sheet layer 20A and the second sheet layer 20B have an elastic film stretchable structure 20X, a stretching and contracting direction of which corresponds to the width direction, joined via through holes 31 penetrating the elastic film 30 at a large number of sheet bond portions 40 arranged at intervals as illustrated in FIG. 7. A planar shape of the outer body 20 is formed including concave leg lines 29 such that both side edges of the intermediate region L in the width direction form the leg openings, and corresponds to a pseudo-hourglass shape as a whole. The outer body 20 may be divided into two front and back parts, and the both parts may be separated from each other in the front-back direction in the crotch portion.

Figure 2:
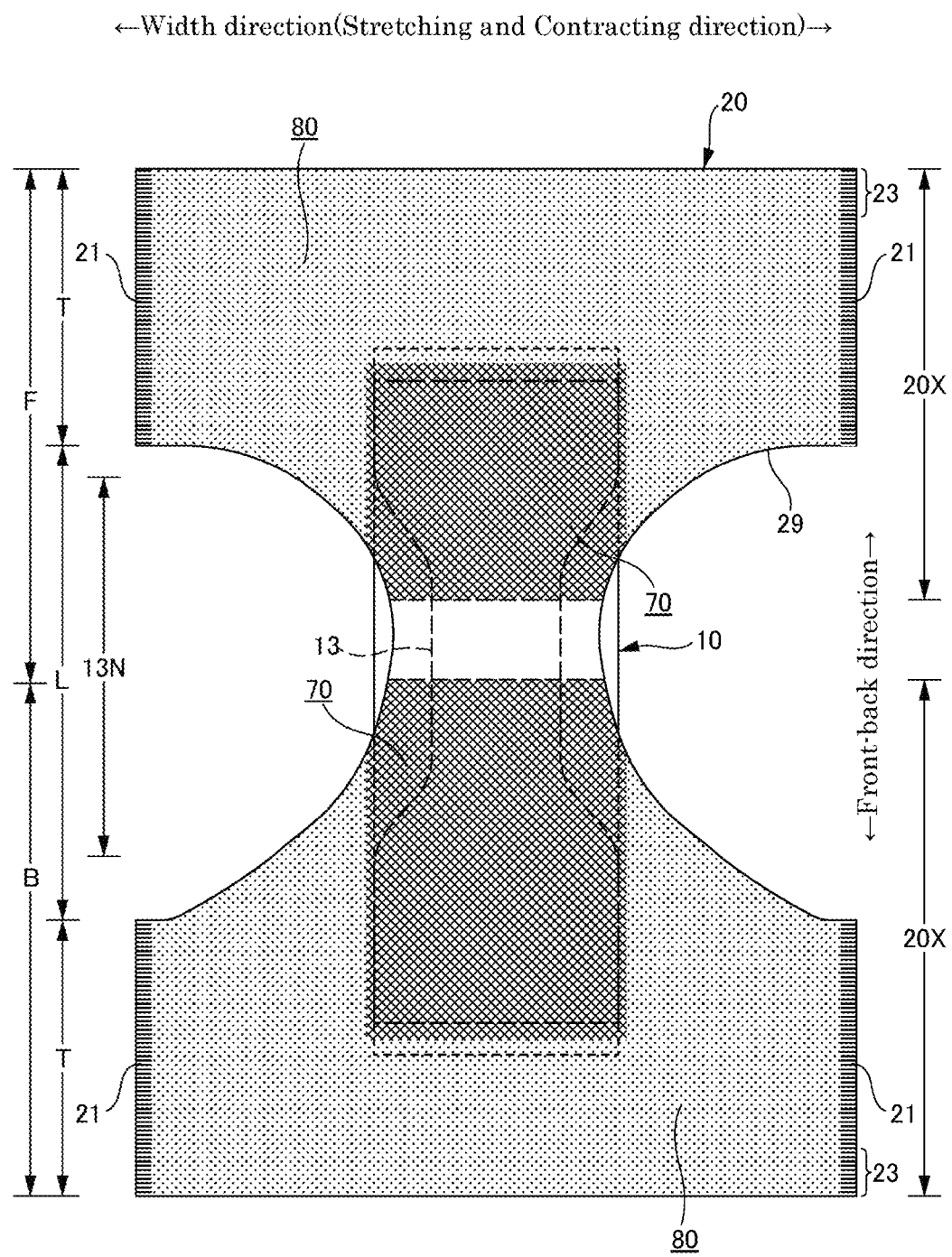
FIG. 2 is a plan view (external surface side) of the underpants-type disposable diaper in the spread state.
Figure 15:
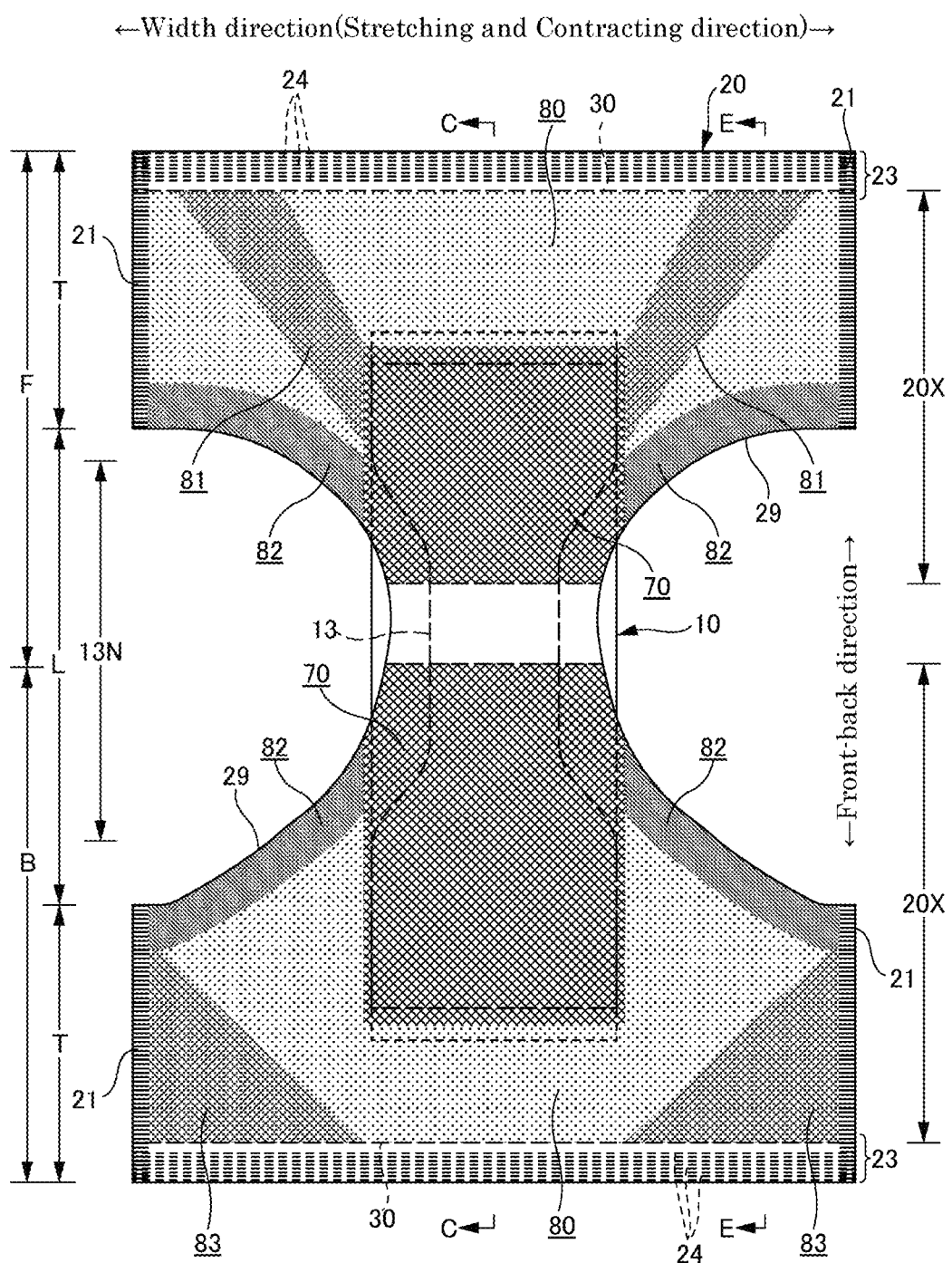
FIG. 15 is a plan view (external surface side) of the underpants-type disposable diaper in the spread state.
Figure 16A:
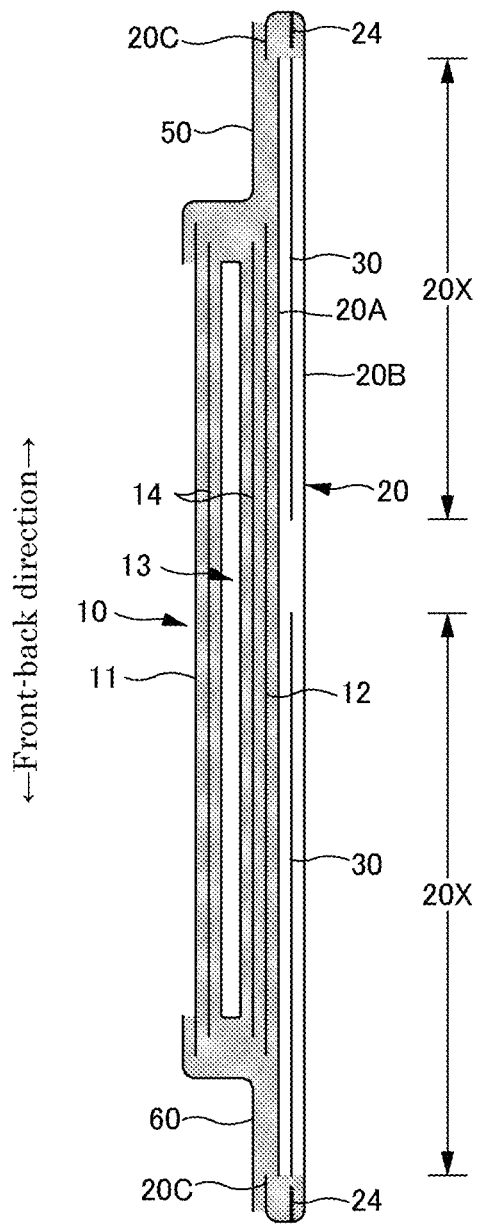
FIG. 16A is a C-C cross-sectional view of FIG. 15 and FIG. 22.
Figure 16B:
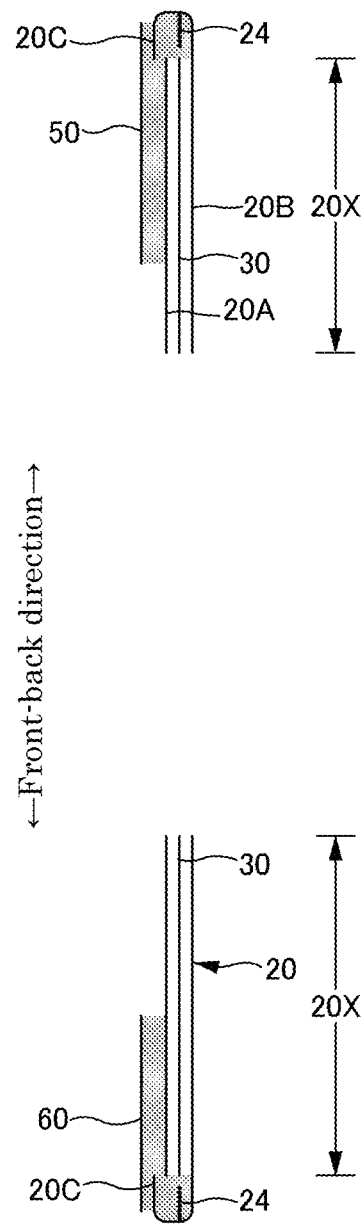
FIG. 16B is an E-E cross-sectional view of FIG. 15 and FIG. 22.

The modes illustrated in FIG. 1 and FIG. 2 correspond to a mode in which the elastic film stretchable structure 20X extends to the waist end portion region 23. However, when the elastic film stretchable structure 20X is used in the waist end portion region 23, tightening of the waist end portion region 23 is insufficient. It is possible to provide a stretchable structure according to a conventional elongated waist end portion elastic member 24 as necessary without providing the elastic film stretchable structure 20X in the waist end portion region 23 as illustrated in FIG. 15 and FIG. 16. The waist end portion elastic members 24 correspond to elongated elastic members such as a plurality of rubber threads disposed at intervals in the front-back direction, and apply a stretching force to tighten around the waist of the body. The waist end portion elastic members 24 are not disposed substantially in a bundle with a close spacing, and three or more, preferably five or more members are disposed at intervals of about 3 to 8 mm to form a predetermined stretchable zone. A stretch rate of the waist end portion elastic member 24 in fixing may be appropriately determined. However, the stretch rate may be set to about 230 to 320% in the case of normal adult use. Rubber threads are used as the waist end portion elastic members 24 in an illustrated example. However, for example, another elongated elastic member such as flat rubber may be used.

As another mode, although not illustrated, the elastic film stretchable structure 20X may not be provided in the intermediate region L between the torso region T of the front body F and the torso region T of the back body B, the stretchable structure 20X may be continuously provided in the front-back direction from the inside of the torso region T of the front body F to the inside of the torso region T of the back body B through the intermediate region L, or the elastic film stretchable structure 20X may be provided only in any one of the front body F and the back body B.

A shape of each of the sheet bond portions 40 and the through holes 31 in a natural length state may be appropriately determined. However, it is possible to adopt an arbitrary shape such as a perfect circle (see FIG. 7 and FIG. 8), an ellipse, a polygon such as a triangle, a rectangle (see FIG. 9 to FIG. 12), a rhombus (see FIG. 13B), etc., a convex lens shape (see FIG. 13A), a concave lens shape (see FIG. 14A), a star shape, a cloud shape, etc. The dimensions of each of the sheet bond portions are not particularly restricted. However, a maximum length 40$x$ is preferably set to 0.5 to 3.0 mm, particularly 0.7 to 1.1 mm, and a maximum width is preferably set to 0.1 to 3.0 mm, particularly 0.1 to 1.1 mm in a case of a shape which is long in a direction orthogonal to the stretching and contracting direction.

A size of each of the sheet bond portions 40 may be appropriately determined. However, when the size is excessively large, an influence of hardness of the sheet bond portions 40 on a sense of touch increases. When the size is excessively small, a joining area is small, and materials may not be sufficiently attached to each other. Thus, in general, an area of each of the sheet bond portions 40 is preferably set to about 0.14 to 3.5 mm$^2$. An area of an opening of each of the through holes 31 may be greater than or equal to that of each of the sheet bond portions since the sheet bond portions are formed via the through holes 31. However, the area is preferably set to about 1 to 1.5 times the area of each of the sheet bond portions. The area of the opening of each through hole 31 refers to a value in a natural length state in a state that the elastic film 30, the first sheet layer 20A, and the second sheet layer 20B are provided in one unit, rather than a state of the elastic film 30 alone, and refers to a minimum value in a case in which the area of the opening of each through hole 31 is not uniform in a thickness direction such as a case in which the area is different between a front side and a back side of the elastic film 30.

A planar array of the sheet bond portions 40 and the through holes 31 may be appropriately determined. However, it is preferable to adopt a planar array in which the sheet bond portions 40 and the through holes 31 are regularly repeated. In addition to the planar array in which the sheet bond portions 40 and the through holes 31 are regularly repeated such as an oblique lattice shape illustrated in FIG. 21A, a hexagonal lattice shape illustrated in FIG. 21B (these shapes are also referred to as a staggered shape), a square lattice shape illustrated in FIG. 21C, a rectangular lattice shape illustrated in FIG. 21D, a parallel body lattice shape illustrated in FIG. 21E (a mode in which two groups are provided such that a large number of parallel oblique row groups intersect each other as illustrated in the figure), etc. (including a mode in which these shapes are inclined at an angle less than 90 degrees with respect to the stretching and contracting direction), it is possible to adopt a planar array in which a group of the sheet bond portions 40 (arrangement of a group unit may be regular or irregular, and a pattern, a letter shape, etc. may be used) is regularly repeated.

In the sheet bond portions 40, the first sheet layer 20A and the second sheet layer 20B are joined via the through holes 31 formed in the elastic film 30. In this case, it is preferable that the first sheet layer 20A is not and the second sheet layer 20B is not joined to the elastic film 30 in a portion other than at least between the first sheet layer 20A and the second sheet layer 20B in the sheet bond portions 40.

Joining means for the first sheet layer 20A and the second sheet layer 20B in the sheet bond portions 40 is not particularly restricted. For example, the first sheet layer 20A and the second sheet layer 20B in the sheet bond portions 40 may be joined using a hot-melt adhesive or joining means based on material welding such as heat sealing, ultrasonic sealing, etc.

As a mode in which the sheet bond portions 40 are formed by material welding, it is possible to adopt any one of a first welding mode (see FIG. 17A) in which the first sheet layer 20A and the second sheet layer 20B are joined only by a melted and solidified material 20m corresponding to a most part or a part of at least one of the first sheet layer 20A and the second sheet layer 20B in the sheet bond portions 40, a second welding mode (see FIG. 17B) in which the first sheet layer 20A and the second sheet layer 20B are joined only by a melted and solidified material 30m corresponding to a whole, a most part, or a part of the elastic film 30 in the sheet bond portions 40, and a third welding mode (see FIG. 17C) obtained by combining these welding modes, and it is preferable to adopt the second and third welding modes. A particularly preferable mode is a mode in which the first sheet layer 20A and the second sheet layer 20B are joined by the melted and solidified material 20m corresponding to a part the first sheet layer 20A and the second sheet layer 20B and the melted and solidified material 30m corresponding to a whole or a most part of the elastic film 30 in the sheet bond portions 40. While the melted and solidified material 30m of the elastic film 30 appearing in white is seen in the melted material 20m with fibers of the first sheet layer 20A or the second sheet layer 20B appearing in black in the third welding mode illustrated in FIG. 19B, the melted and solidified material of the elastic film is not seen in the melted and solidified material 20m of the first sheet layer 20A or the second sheet layer 20B in the first welding mode illustrated in FIG. 19A (a while part corresponds to a boundary of the melted and solidified material 20m with fibers and scattered reflection of the melted and solidified material 20m) with fibers.

When the first sheet layer 20A and the second sheet layer 20B are bonded using the melted and solidified material 20m corresponding to a most part or a part of at least one of the first sheet layer 20A and the second sheet layer 20B as an adhesive as in a first adhesive mode or a third adhesive mode, it is preferable that a part of the first sheet layer 20A and the second sheet layer 20B does not melt since the sheet bond portions 40 are not hardened. When the first sheet layer 20A and the second sheet layer 20B correspond to a nonwoven fabric, a case in which a part of the first sheet layer 20A and the second sheet layer 20B does not melt includes a mode in which a core (including a central portion of a single component fiber in addition to a core in a conjugate fiber) remains for all fibers of the sheet bond portions 40 and a surrounding portion (including a portion on a surface layer side of a single component fiber in addition to a sheath in a conjugate fiber) melts, or a mode in which some fibers do not melt while all remaining fibers melt or a core remains while a surrounding portion melts.

Peeling strength becomes high when the first sheet layer 20A and the second sheet layer 20B are bonded using the melted and solidified material 30m of the elastic film 30 as an adhesive as in the second welding mode and the third welding mode. In the second welding mode, under the condition that a melting point of at least one of the first sheet layer 20A and the second sheet layer 20B is higher than a melting point of the elastic film 30 and a heating temperature at the time of forming the sheet bond portions 40, the elastic film 30 may be interposed between the first sheet layer 20A and the second sheet layer 20B, a part corresponding to the sheet bond portions 40 may be pressed and heated, and only the elastic film 30 may be melted, thereby performing manufacture. Meanwhile, in the third welding mode, under the condition that a melting point of at least one of the first sheet layer 20A and the second sheet layer 20B is higher than the melting point of the elastic film 30, the elastic film 30 may be interposed between the first sheet layer 20A and the second sheet layer 20B, the part corresponding to the sheet bond portions 40 may be pressed and heated, and at least one of the first sheet layer 20A and the second sheet layer 20B and the elastic film 30 may be melted, thereby performing manufacture. From this point of view, the melting point of the elastic film 30 is preferably about 80 to 145° C., melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 90° C. In addition, the heating temperature is preferably set to 100 to 150° C.

Figure 17A:
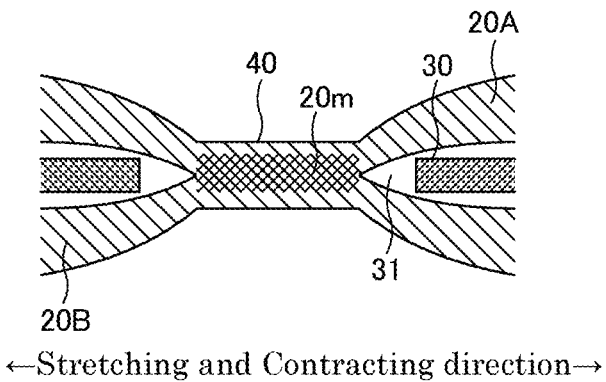
FIG. 17A, FIG. 17B and FIG. 17C are cross-sectional views, each schematically illustrating a cross section of a main part of an outer body stretched to some extent.
Figure 17B:
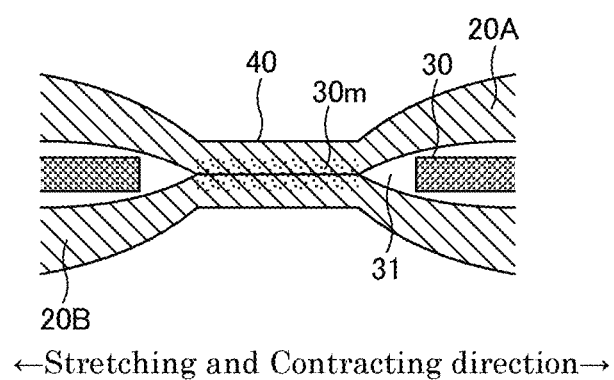
Figure 17C:
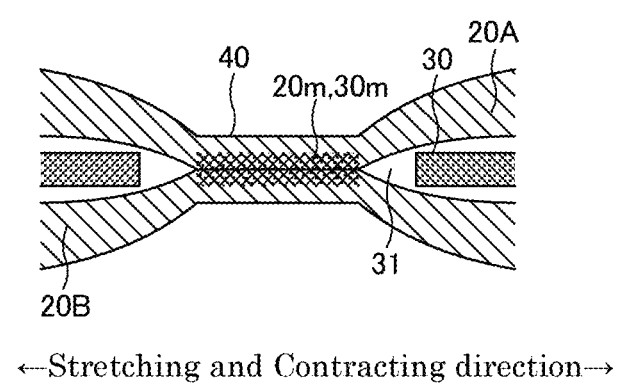
Figure 18A:
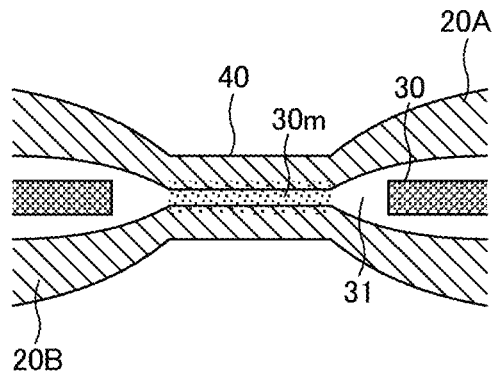
FIG. 18A, FIG. 18B and FIG. 18C are cross-sectional views, each schematically illustrating a cross section of a main part of an outer body stretched to some extent.
Figure 18B:
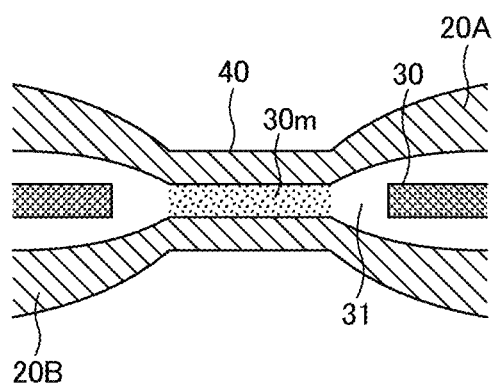
Figure 18C:
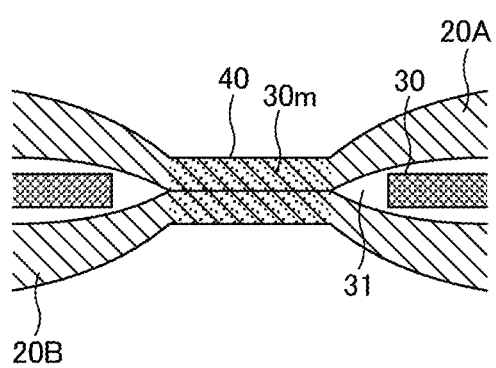
Figure 19A:
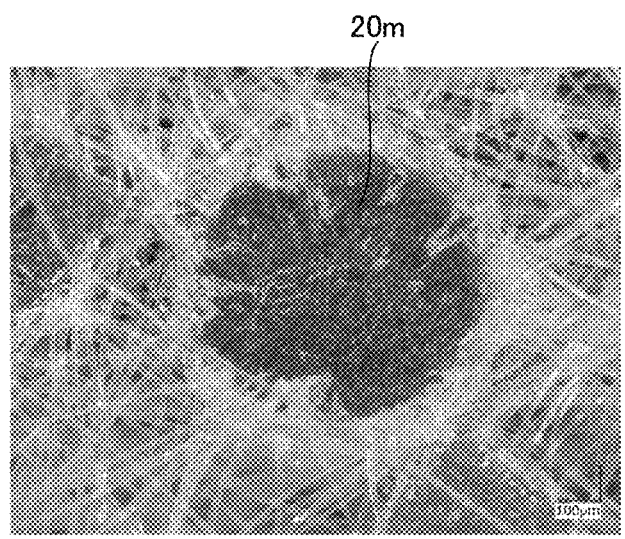
FIG. 19A is a plan photograph of a sheet bond portion formed in a first welding mode.
Figure 19B:
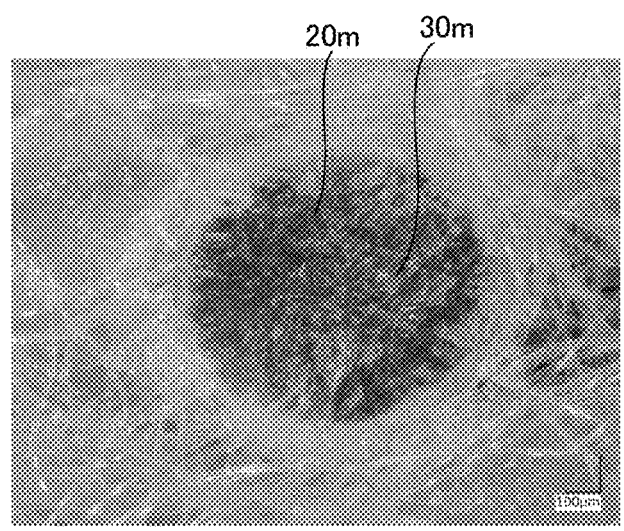
FIG. 19B is a plan photograph of the sheet bond portion formed in a third welding mode.

In the second welding mode and the third welding mode, when the first sheet layer 20A and the second sheet layer 20B are nonwoven fabric, the melted and solidified material 30m of the elastic film 30 may infiltrate among fibers over the whole thickness direction of the first sheet layer 20A and the second sheet layer 20B of the sheet bond portions 40 as illustrated in FIG. 18C. However, flexibility of the sheet bond portions 40 becomes high in a mode in which the melted and solidified material 30m infiltrates among fibers in the thickness direction halfway as illustrated in FIGS. 17B, 17C, and FIG. 18A, or a mode in which the melted and solidified material 30m hardly infiltrates among the fibers of the first sheet layer 20A and the second sheet layer 20B as illustrated in FIG. 18B.

Figure 20:
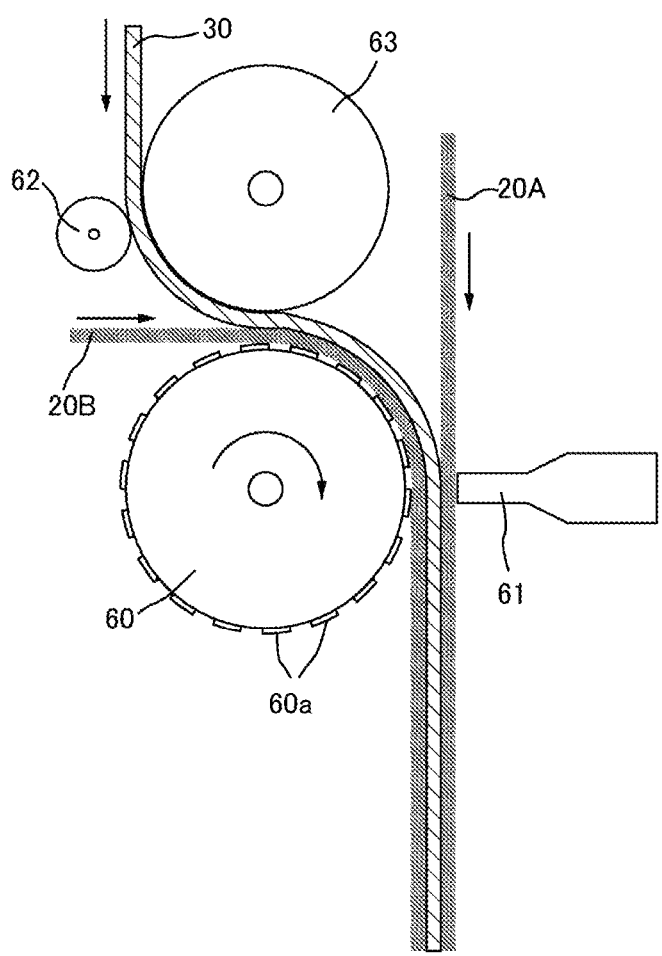
FIG. 20 is a schematic view of an ultrasonic sealing device.
Figure 21A:
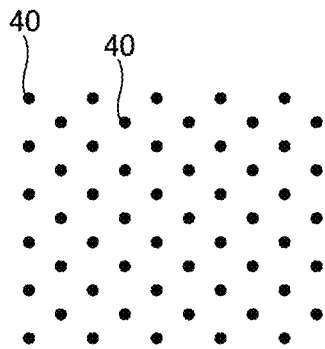
FIG. 21A, FIG. 21B, FIG. 21C, FIG. 21D, FIG. 21E are plan views, each illustrating various arrangement examples of the sheet bond portion.
Figure 21B:
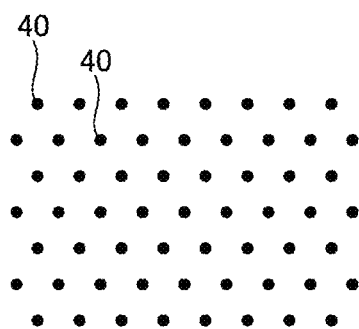
Figure 21C:
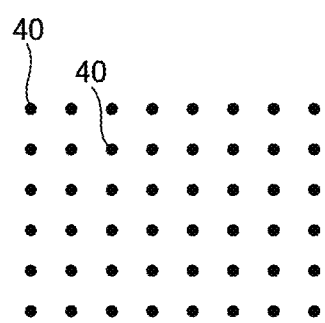
Figure 21D:
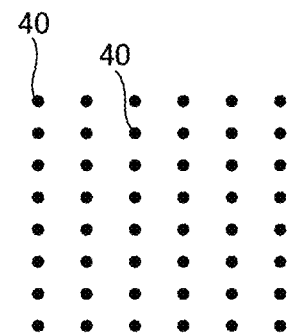
Figure 21E:
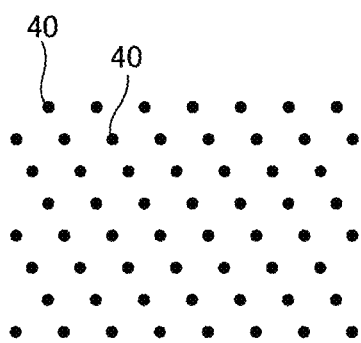

FIG. 20 illustrates an example of an ultrasonic sealing device suitable for forming the second welding mode and the third welding mode. In this ultrasonic sealing device, in forming the sheet bond portions 40, the first sheet layer 20A, the elastic film 30, and the second sheet layer 20B are fed to between an ultrasonic horn 61 and an anvil roll 60 having protrusions 60a formed in a pattern of the sheet bond portions 40 on an external surface. In this instance, for example, when a feed speed of conveyance of the elastic film 30 at an upstream side by a feed drive roll 63 and a nip roll 62 is set to be lower than a speed of conveyance after the anvil roll 60 and the ultrasonic horn 61, the elastic film 30 is stretched to a predetermined stretch rate in an MD (machine direction, flow direction) on a path from a nip position by the feed drive roll 63 and the nip roll 62 to a sealing position by the anvil roll 60 and the ultrasonic horn 61. A stretch rate of the elastic film 30 may be set by selecting a speed difference between the anvil roll 60 and the feed drive roll 63, and may be set to, for example, about 300% to 500%. Reference symbol 62 denotes the nip roll. The first sheet layer 20A, the elastic film 30, and the second sheet layer 20B fed to between the anvil roll 60 and the ultrasonic horn 61 are heated by ultrasonic vibration energy of the ultrasonic horn 61 while being pressed between the protrusions 60a and the ultrasonic horn 61 in a stacked state in this order. Further, the through holes 31 are formed in the elastic film 30 by melting only the elastic film 30 or melting at least one of the first sheet layer 20A and the second sheet layer 20B and the elastic film 30. At the same time, the first sheet layer 20A and the second sheet layer 20B are joined via the through holes 31. Therefore, in this case, an area rate of the sheet bond portions 40 may be selected by selecting a size, a shape, a separation interval, an arrangement pattern in a roll length direction and a roll circumferential direction, etc. of the protrusions 60a of the anvil roll 60.

Figure 7A:
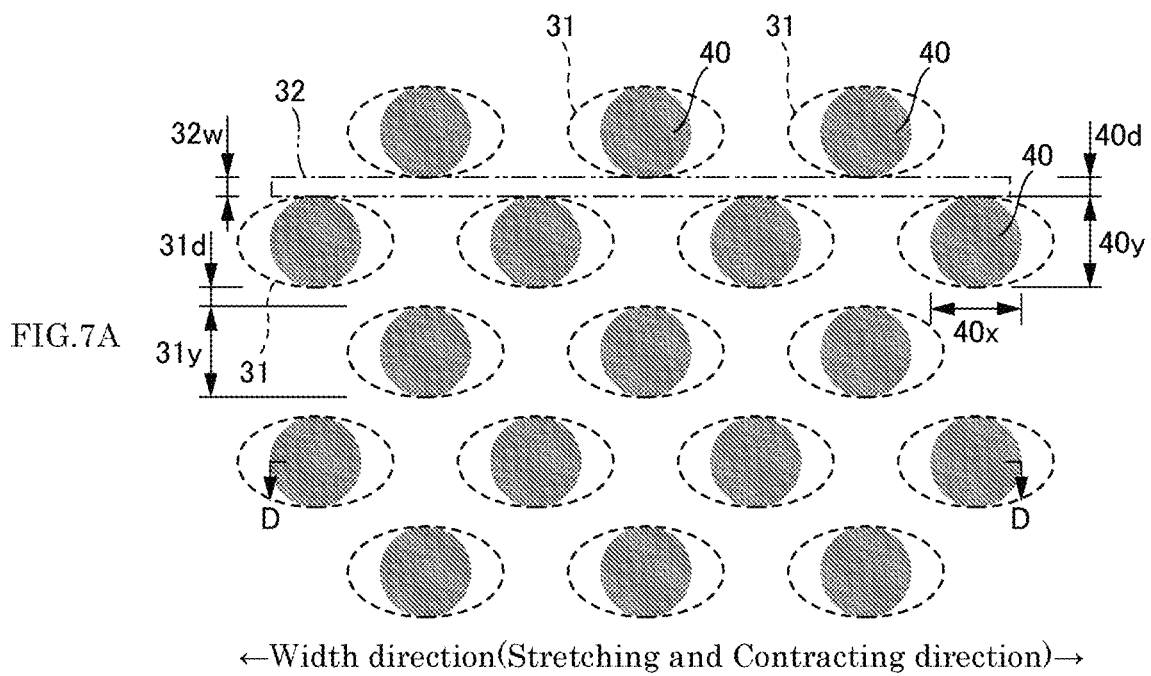
FIG. 7A is a plan view of a main part of a stretchable region.
Figure 7B:
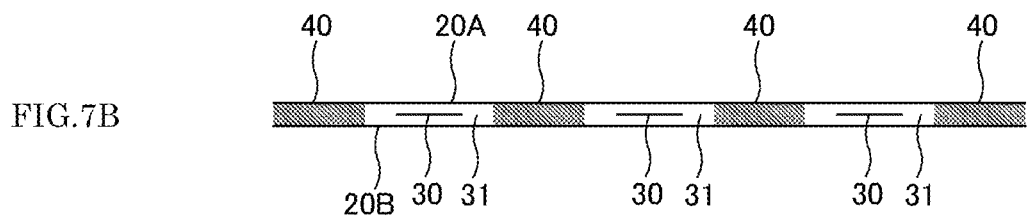
FIG. 7B is a D-D cross-sectional view of FIG. 7A.
Figure 9A:
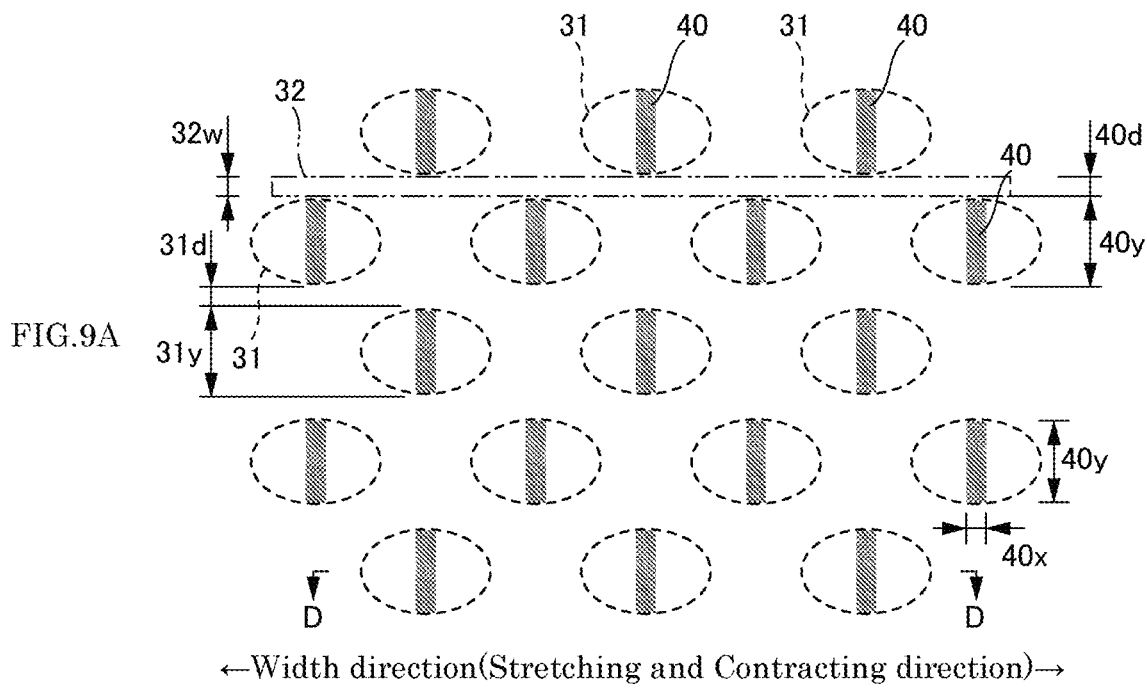
FIG. 9A is a plan view of a main part of the stretchable region.
Figure 9B:
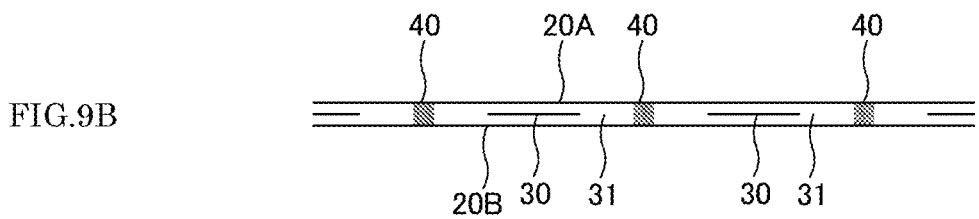
FIG. 9B is a D-D cross-sectional view of FIG. 9A.
Figure 11A:
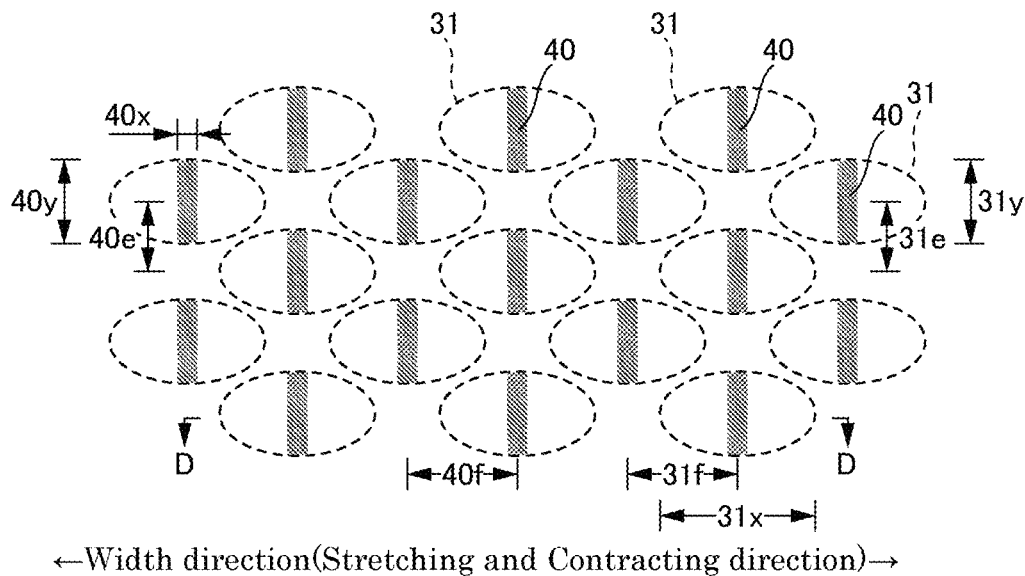
FIG. 11A is a plan view of a main part of a non-stretchable region.
Figure 11B:
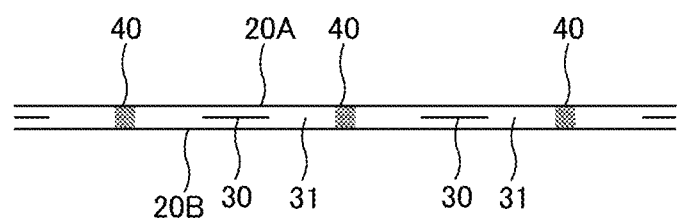
FIG. 11B is a D-D cross-sectional view of FIG. 11A.
Figure 11C:
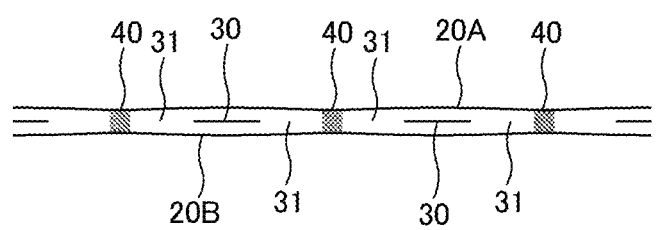
FIG. 11C is a cross-sectional view in the worn state.
Figure 11D:
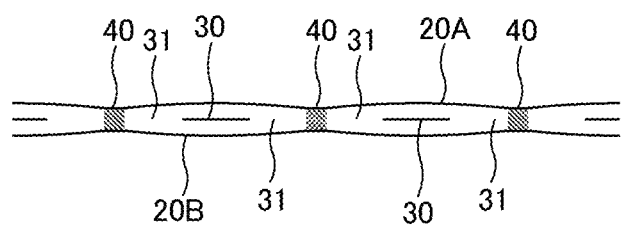
FIG. 11D is a cross-sectional view in the natural length state.
Figure 12:
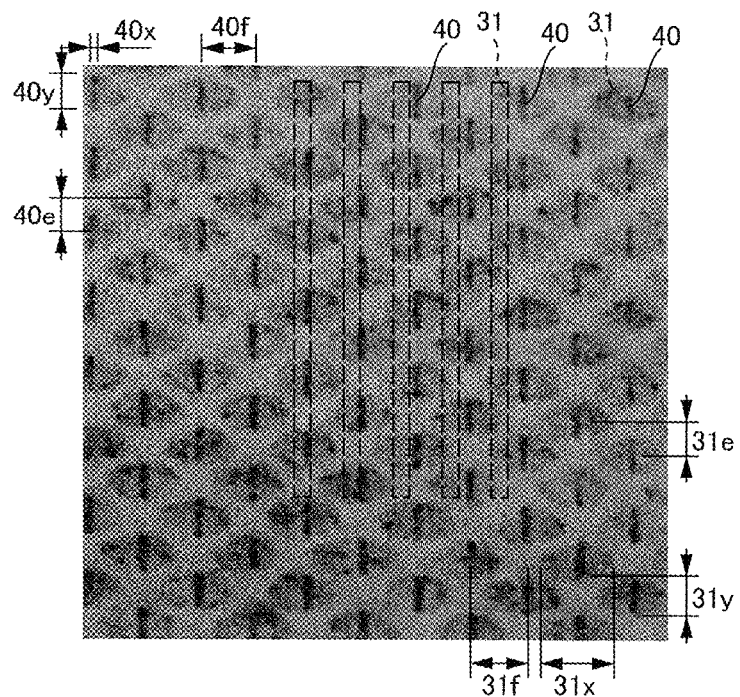
FIG. 12 is a photograph of the non-stretchable region of the sample.
Figure 13A:
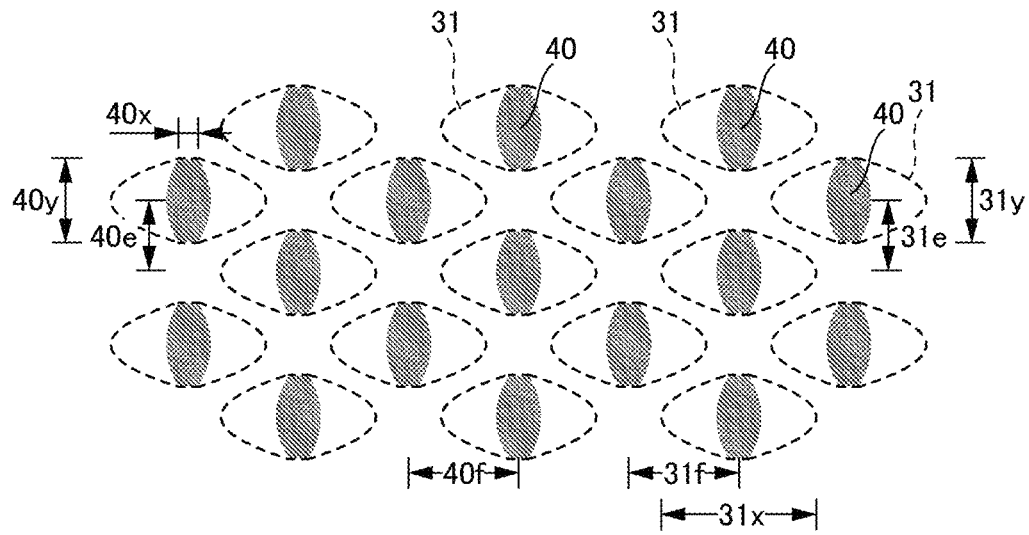
FIG. 13A and FIG. 13B are plan views of a main part of the non-stretchable region.
Figure 13B:
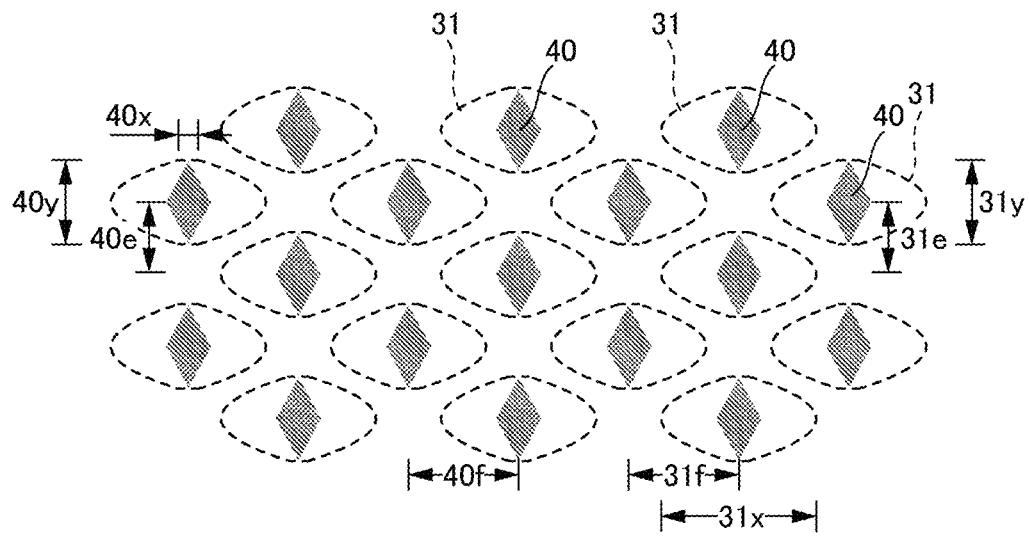
Figure 14A:
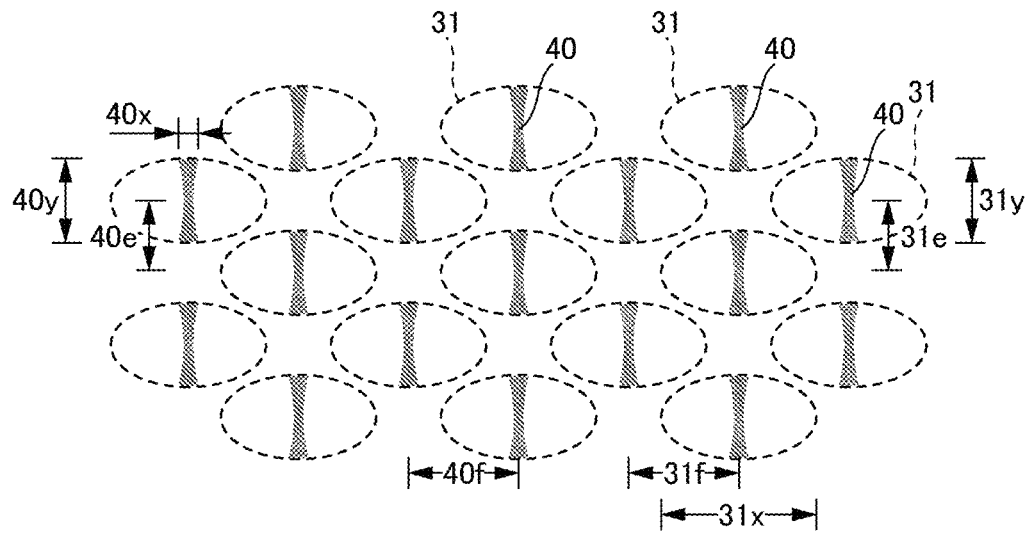
FIG. 14A and FIG. 14B are plan views of a main part of the non-stretchable region.
Figure 14B:
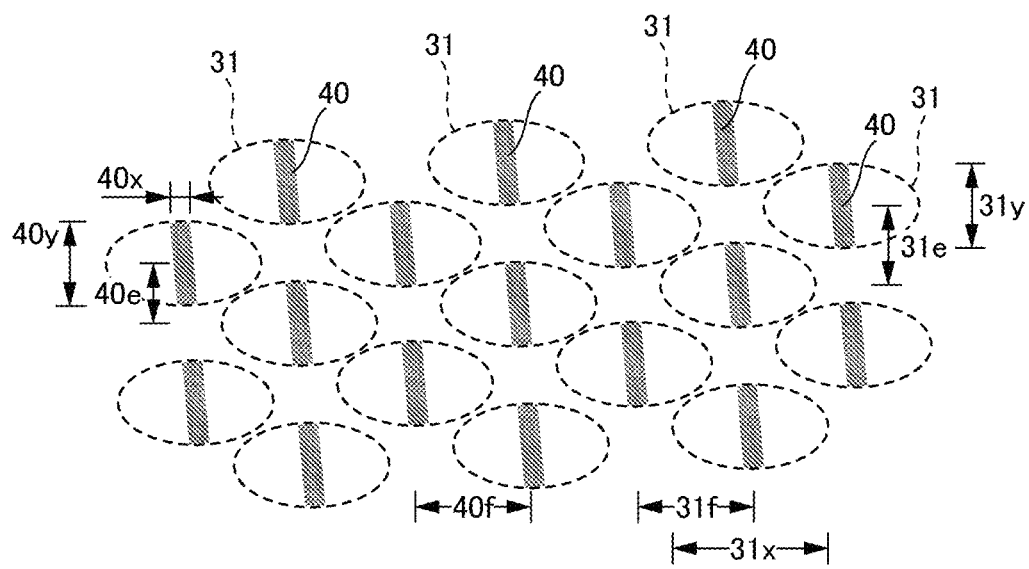

Although the reason for formation of the through holes 31 is not necessarily clear, it is considered that openings are formed by melting the elastic film 30 at corresponding sites to the protrusions 60a of the anvil roll 60 so as to be removed from the surroundings. In this instance, a portion between the two adjacent through holes 31 arranged in the stretching and contracting direction in the elastic film 30 is cut at both sides thereof in the stretching and contracting direction by the through holes 31 as illustrated in FIG. 7A, FIG. 9A, and FIG. 11A, and support at both the side portions in a contraction direction is lost. Thus, within an extent that continuity in a direction orthogonal to the contraction direction can be maintained, the closer to the central side of a direction orthogonal to the stretching and contracting direction, the more elastic film 30 contracts to match with the central side in the stretching and contracting direction so that the through holes 31 are enlarged in the stretching and contracting direction. When the sheet bond portions 40 are formed in a pattern with a section being left in which the elastic film 30 linearly continues along the stretching and contracting direction, as in the stretchable region 80 explained after, the elastic film 30 contracts to the natural length state for example by cutting for obtaining individual products, an enlarged portion of each through hole 31 contracts in the stretching and contracting direction so that a gap cannot be formed between each through hole 31 and each sheet bond portion 40 as illustrated in FIG. 7A and FIG. 9A. On the other hand, when the sheet bond portions 40 are formed in a pattern without such a section in which the elastic film 30 linearly continues along the stretching and contracting direction, as in the non-stretchable region 70 explained after, even if the elastic film 30 is cut for obtaining the individual products, contraction is not substantially performed, as illustrated in FIG. 11A. Thus, a large gap is left between each through hole 31 and each sheet bond portion 40.

(Stretchable Region and Non-Stretchable Region)

A region having the elastic film stretchable structure 20X in the outer body 20 includes the non-stretchable region 70 and the stretchable region 80 stretchable in the width direction provided at least at one side of the non-stretchable region 70 in the width direction. Arrangement of the stretchable region 80 and the non-stretchable region 70 may be appropriately determined. In the case of the outer body 20 of the underpants-type disposable diaper as in the present embodiment, a portion overlapping the absorber 13 is a region that may not be stretched or contracted. Thus, a part or total of the portion overlapping the absorber 13 (desirably including substantially the whole internal and external fixed region 10B) is preferably set to the non-stretchable region 70 as in the illustrated mode. The non-stretchable region 70 may be provided from a region overlapping the absorber 13 to a region not overlapping the absorber 13 positioned in the width direction or the front-back direction thereof, and the non-stretchable region 70 may be provided only in the region not overlapping the absorber 13.

(Stretchable Region)

The stretchable region 80 has the section 32 in which the elastic film 30 linearly continues along the width direction, contracts in the width direction by a contraction force of the elastic film 30 while it is possible that the stretchable region 80 is stretched in the width direction. More specifically, the whole elastic film stretchable structure 20X including both the stretchable region 80 and the non-stretchable region 70 is formed by joining the first sheet layer 20A and the second sheet layer 20B via the through holes 31 of the elastic film 30 to form a large number of sheet bond portions 40 arranged at intervals in the width direction and the front-back direction orthogonal thereto (the direction orthogonal to the stretching and contracting direction) while the elastic film 30 is stretched in the width direction. Further, in the stretchable region 80, the through holes 31 may be disposed to have the section in which the elastic film 30 linearly continues along the width direction, thereby imparting elasticity.

Figure 7C:
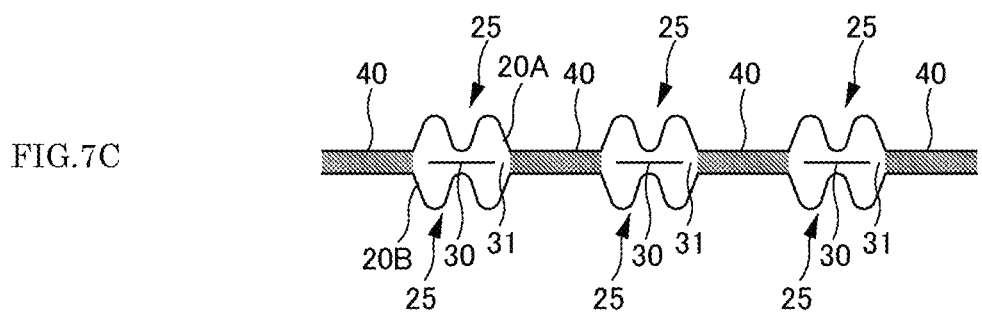
FIG. 7C is a cross-sectional view in a worn state.
Figure 7D:
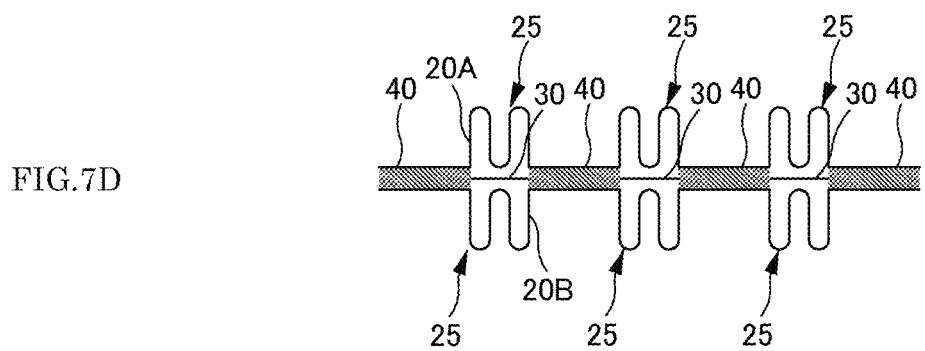
FIG. 7D is a cross-sectional view in a natural length state.
Figure 8A:
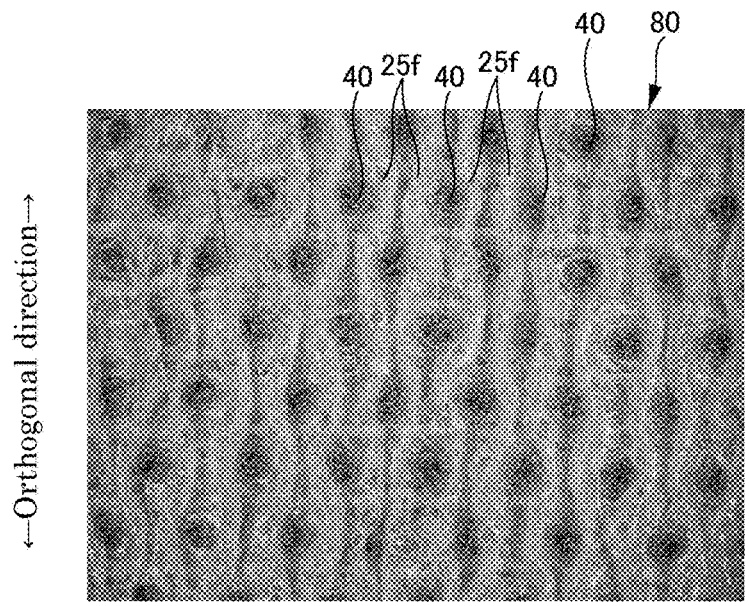
FIG. 8A is a microscope photograph from a plane direction.
Figure 8B:
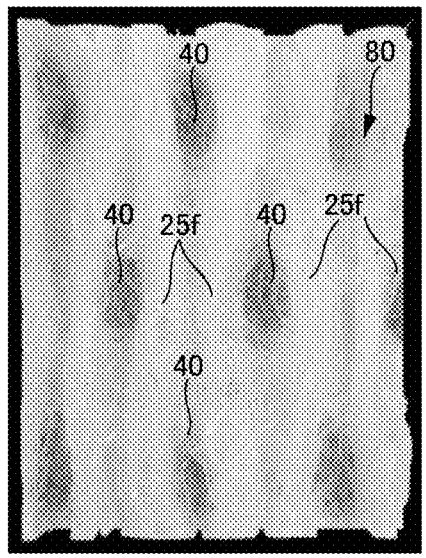
FIG. 8B is a high-magnification microscope photograph from the plane direction.
Figure 8C:
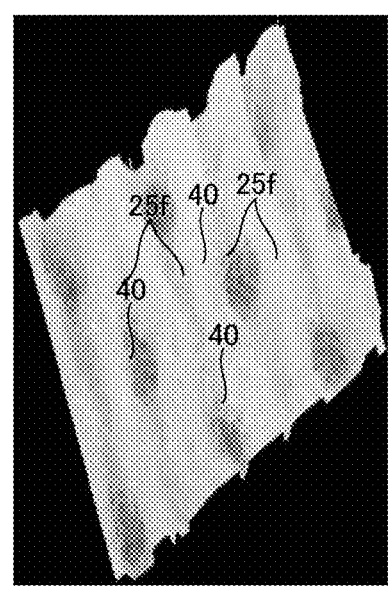
FIG. 8C is a high-magnification microscope photograph from an oblique direction in a stretchable region of a sample.
Figure 9C:
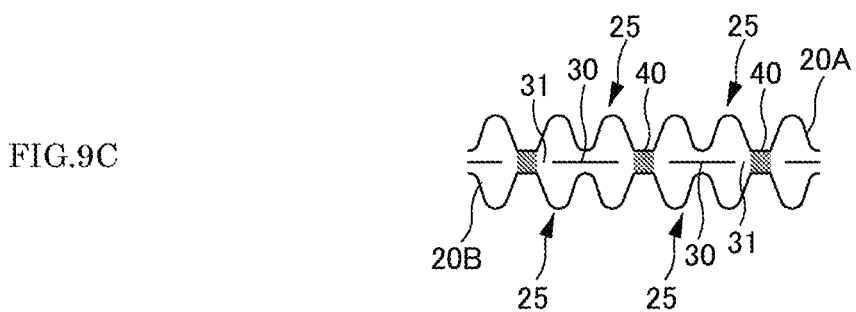
FIG. 9C is a cross-sectional view in the worn state.
Figure 9D:
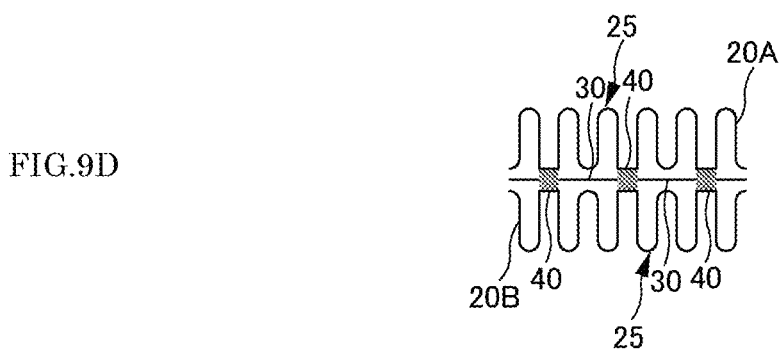
FIG. 9D is a cross-sectional view in the natural length state.
Figure 10A:
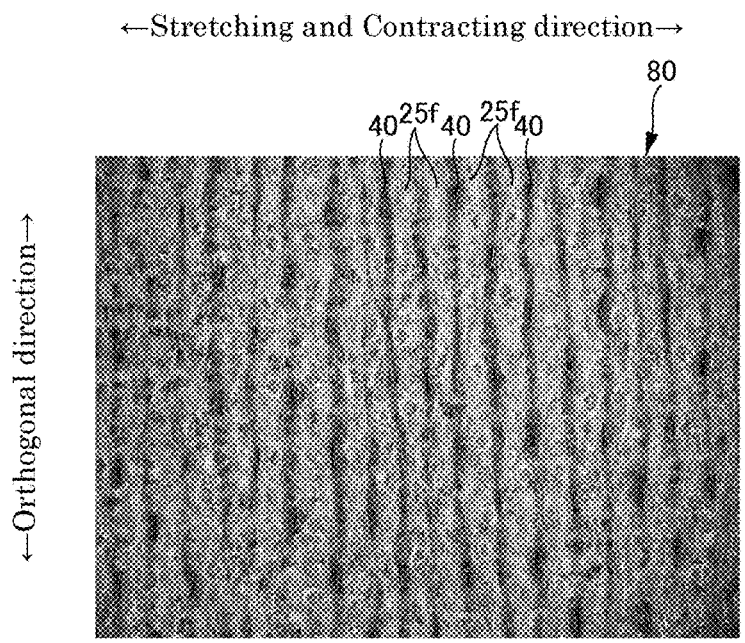
FIG. 10A is a microscope photograph from the plane direction.
Figure 10B:
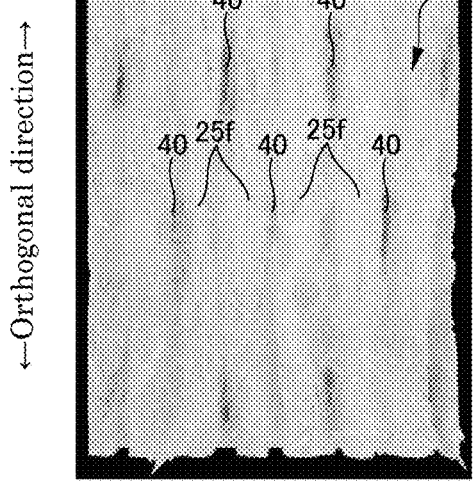
FIG. 10B is a high-magnification microscope photograph from the plane direction.
Figure 10C:
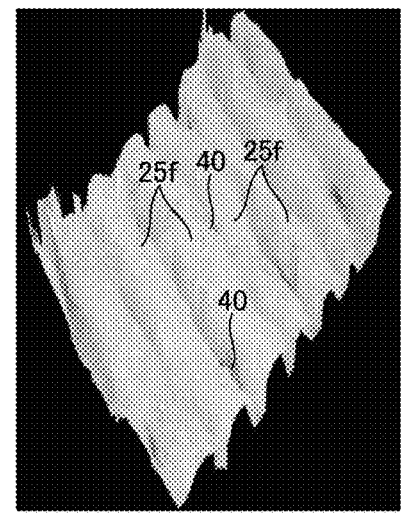
FIG. 10C is a high-magnification microscope photograph from the oblique direction in the stretchable region of the sample.

In the stretchable region 80, as illustrated in FIG. 7D and FIG. 9D, when the elastic film 30 is in the natural length state, the first sheet layer 20A and the second sheet layer 20B between each pair of adjacent sheet bond portions 40 rise in a direction away from each other, and thus a contraction wrinkle 25 extending in the front-back direction is formed. In a worn state in which the elastic film 30 is stretched to an extent in the width direction, as illustrated in FIG. 7C and FIG. 9C, the contraction wrinkles 25 are still remain although the contraction wrinkles 25 are stretched. In addition, as in the illustrated mode, when the first sheet layer 20A is not and the second sheet layer 20B is not joined to the elastic film 30 in a portion other than at least between the first sheet layer 20A and the second sheet layer 20B in the sheet bond portions 40, as understood from FIG. 7C and FIG. 9D assuming the worn state and FIGS. 7A and 7B and FIGS. 9A and 9B assuming a spread state of the first sheet layer 20A and the second sheet layer 20B, a gap is formed between each through hole 31 of the elastic film 30 and each sheet bond portion 40 and in these states, air permeability is imparted due to the gap even when a material of the elastic film 30 corresponds to a non-porous film or a sheet. In addition, when the elastic film 30 is in the natural length state illustrated in FIG. 7D and FIG. 9D, the through holes

31 are narrowed by contraction of the elastic film 30, and a gap is hardly formed between the through hole 31 and the sheet bond portion 40. States of the contraction wrinkle 25 in the worn state and the natural length state are shown in reference sample photographs of FIG. 8 and FIG. 10.

An elongation at an elastic limit of the stretchable region 80 in the width direction is desirably set to 200% or more (preferably 265% to 295%). The elongation at the elastic limit of the stretchable region 80 is substantially determined by the stretch rate of the elastic film 30 in the manufacturing. However, the elongation at the elastic limit decreases due to a factor that inhibits contraction in the width direction based thereon. A main inhibition factor corresponds to a ratio of the length 40$x$ of the sheet bond portions 40 to a unit length in the width direction. As this ratio increases, the elongation at the elastic limit decreases. In general, since the length 40$x$ of the sheet bond portions 40 correlates with the area rate of the sheet bond portions 40, the elongation at the elastic limit of the stretchable region 80 may be adjusted by the area rate of the sheet bond portions 40.

A stretching stress of the stretchable region 80 may be adjusted mainly by a sum of widths 32$w$ of the sections 32 in each of which the elastic film 30 linearly continues along the width direction. The width 32$w$ of the section 32 in which the elastic film 30 linearly continues along the width direction is equal to an interval 31$d$ of the through holes 31 coming into contact with both side edges of the section 32 in the front-back direction. The interval 31$d$ of the adjacent two through holes 31 is equal to an interval 40$d$ of the adjacent two sheet bond portions 40 coming into contact with the both side edges of the section in which the elastic film 30 linearly continues in the front-back direction when a length 31$y$ of each through hole 31 in the front-back direction is equal to a length 40$y$ of each sheet bond portion 40 in the front-back direction (when a scheme of simultaneously forming the through holes 31 and the sheet bond portions 40 described above is adopted). Therefore, in this case, the stretching stress of the stretchable region 80 may be adjusted by a ratio of the length 40$y$ of the sheet bond portions 40 to a unit length in the front-back direction. In general, since the length 40$y$ of the sheet bond portions 40 correlates with the area rate of the sheet bond portions 40, the stretching stress of the stretchable region 80 may be adjusted by the area rate of the sheet bond portions 40. The stretching stress at the time of stretching to an elastic limit of 50% may be estimated as the stretching stress of the stretchable region 80.

The area rate of the sheet bond portions 40 and the area of each of the sheet bond portions 40 in the stretchable region 80 may be appropriately determined. However, in general, the area rate and the areas are preferably set within the following ranges.

Area of each of sheet bond portions 40: 0.14 to 3.5 mm$^2$ (particularly 0.14 to 1.0 mm$^2$)

Area rate of sheet bond portions 40: 1.8 to 19.1% (particularly 1.8 to 10.6%)

As described above, the elongation at the elastic limit and the stretching stress of the stretchable region 80 may be adjusted by the area of each of the sheet bond portions 40. Thus, as illustrated in FIG. 15, it is possible to provide a plurality of regions having different area rates of the sheet bond portions 40 in the stretchable region 80, and to change fitness according to sites. In a mode illustrated in FIG. 15, a region 81 extending in an oblique direction along a groin and an edge portion region 82 of the leg opening in the front body F have a high area rate of the sheet bond portions 40, and thus have a small stretching stress when compared to the other regions. Therefore, the regions correspond to a region that flexibility stretches and contracts. In addition, an ilium facing region 83 and the edge portion region 82 of the leg opening in the back body B have a high area rate of the sheet bond portions 40, and thus have a small stretching stress when compared to the other regions. Therefore, the regions correspond to a region that flexibility stretches and contracts.

(Non-Stretchable Region)

Meanwhile, the non-stretchable region 70 is set to a region not having the section in which the elastic film 30 linearly continues along the width direction due to the presence of the through holes 31 even through the elastic film 30 continues in the width direction. Therefore, even though the whole elastic film stretchable structure 20X including both the stretchable region 80 and the non-stretchable region 70 is formed by joining the first sheet layer 20A and the second sheet layer 20B via the through holes 31 of the elastic film 30 to form the large number of sheet bond portions 40 at intervals in the width direction and the front-back direction orthogonal thereto while the elastic film 30 is stretched in the width direction, the elastic film 30 does not linearly continue along the width direction in the non-stretchable region 70 as illustrated in FIG. 11. Thus, the contraction force of the elastic film 30 hardly acts on the first sheet layer 20A and the second sheet layer 20B, elasticity is almost lost, and an elongation at an elastic limit approaches 100%. Further, in the non-stretchable region 70, the first sheet layer 20A and the second sheet layer 20B are joined by the large number of sheet bond portions 40 arranged at intervals, and the sheet bond portions 40 are discontinuous. Thus, a decrease in flexibility is prevented. In other words, it is possible to form the stretchable region 80 and the non-stretchable region 70 depending on the presence or absence of a portion in which the elastic film 30 does not linearly continue along the width direction. In addition, continuity of the elastic film 30 remains in the non-stretchable region 70. As understood from a sample photograph illustrated in FIG. 12, since an independent cut piece of the elastic film 30 is not left, and no wrinkle is formed, appearance is extremely excellent, and air permeability in the thickness direction by the through holes 31 is ensured. In the non-stretchable region 70, an elongation at elastic limit in the width direction is preferably 120% or less (preferably 110% or less, more preferably 100%).

An arrangement pattern of the through holes 31 in the elastic film 30 in the non-stretchable region 70 may be appropriately determined. However, when staggered arrangement is adopted as illustrated in FIG. 11 to FIG. 14, and a pattern in which a center-to-center interval 31$e$ of the adjacent two through holes 31 in the front-back direction is shorter than the length 31$y$ of each of the through holes 31 in the front-back direction is adopted, linear continuity in the width direction may be almost completely eliminated while maintaining continuity of the elastic film 30, and appearance is preferable as illustrated in FIG. 15. In this case, it is more preferable that a center-to-center interval 31$f$ of the adjacent two through holes 31 in the width direction is shorter than a length 31$x$ of each of the through holes 31 in the width direction.

In general, especially when a stretching stress is in a range of 4 to 12 N/35 mm at the time of stretching the elastic film 30 four times in the width direction, in a state in which the non-stretchable region 70 is stretched to an elongation at an elastic limit in the width direction, the center-to-center interval 31$e$ of the adjacent two through holes 31 in the front-back direction is preferably in a range of 0.4 to 2.7 mm, and the length 31y of the through holes 31 in the front-back direction is preferably in a range of 0.5 to 3.0 mm, particularly in a range of 0.7 to 1.1 mm. In addition, the center-to-center interval 31f of the adjacent two through holes 31 in the width direction is preferably 0.5 to 2 times, particularly 1 to 1.2 times the length 31y of the through holes 31 in the front-back direction, and the length 31x of the through holes 31 in the width direction is preferably 1.1 to 1.8 times, particularly 1.1 to 1.4 times the center-to-center interval 31f of the adjacent two through holes 31 in the width direction. In a state in which the non-stretchable region 70 is stretched to an elastic limit in the width direction (in other words, in a state in which the first sheet layer 20A and the second sheet layer 20B are completely spread), the center-to-center interval 31f of the adjacent two through holes 31 in the width direction is equal to a center-to-center interval 40f of the adjacent two sheet bond portions 40 in the width direction, the center-to-center interval 31e of the adjacent two through holes 31 in the front-back direction is equal to a center-to-center interval 40e of the adjacent two sheet bond portions 40 in the front-back direction, and the length 31y of the through holes 31 in the front-back direction is equal to the length 40y of the sheet bond portions 40 in the front-back direction.

In the non-stretchable region 70, in a case in which the first sheet layer 20A is not and the second sheet layer 20B is not joined to the elastic film 30 in a portion other than between the first sheet layer 20A and the second sheet layer 20B in the sheet bond portions 40, and in the natural length state, a gap is provided so as to contain both side portions of each of the sheet bond portions 40 in the width direction, which is generated by peripheral edge of the through hole 31 of the elastic film 30 and the sheet bond portion 40 separated from each other, air permeability is imparted at all times due to the gap even when the material of the elastic film 30 corresponds to a non-porous film or a sheet, and thus the case is preferable. In the case of adopting a scheme of simultaneously forming the through holes 31 and the sheet bond portions 40 described above, this state is naturally obtained irrespective of a shape of the sheet bond portions 40.

The shape of each of the sheet bond portions 40 and each of the through holes 31 in the natural length state is not particularly restricted. However, it is desirable to have a small area from a viewpoint of flexibility, and it is desirable to have a shape which is long in the front-back direction to eliminate linear continuity in the width direction of the elastic film 30. Thus, it is preferable to adopt an ellipse which is long in the front-back direction, a rectangle (see FIG. 11), the rhombus (see FIG. 13B, the convex lens shape (see FIG. 13A), and the concave lens shape (see FIG. 14A). However, when corners are acute as in the rhombus, the elastic film 30 is easily fractured. In contrast, the convex lens shape is preferable since welding of the sheet bond portions 40 is stabilized, and the concave lens shape is preferable in that an area may be further reduced.

It is possible to appropriately determine the area rate of the sheet bond portions 40 and the area of each of the sheet bond portions 40 in the non-stretchable region. However, in general, ranges below are preferable since the area of each of the sheet bond portions 40 is small, the area rate of the sheet bond portions 40 is low, and thus the non-stretchable region 70 is not hardened.

Area of each of sheet bond portions 40: 0.10 to 0.75 mm$^2$ (particularly 0.10 to 0.35 mm$^2$)

Area rate of sheet bond portions 40: 4 to 13% (particularly 5 to 10%)

As described above, the elongation at the elastic limit of the non-stretchable region 70 may be changed by the arrangement pattern of the through holes 31, the dimension of each of the through holes 31, and the center-to-center interval of the adjacent two through holes 31. Therefore, although not illustrated, it is possible to make the elongation at the elastic limit different among a plurality of positions in the stretchable region 80 or a plurality of non-stretchable regions 70. For example, in a preferable mode, an elongation at an elastic limit in the non-stretchable region 70 of the front body F is set to be larger than an elongation at elastic limit in the non-stretchable region 70 of the back body B.

<Second Mode>

Next, a second mode will be described with reference to FIG. 3, FIG. 5 to FIG. 7, FIG. 16, FIG. 21, and FIG. 22 to FIG. 34. In the outer body 20, as illustrated in FIG. 16, FIG. 5, and FIG. 6, the elastic film 30 and the elongated elastic member 24 along the width direction are arranged between the first sheet layer 20A and the second sheet layer 20B, and elasticity in the width direction is imparted. The planar shape of the outer body 20 corresponds to a pseudo-hourglass shape as a whole due to the concave leg lines 29 formed to form leg openings at intermediate both side portions, respectively. The outer body 20 may be divided into two front and back parts, and the both parts may be separated from each other in the front-back direction in the crotch portion.

More specifically, in the outer body 20 of the illustrated mode, the waist end portion elastic member 24 is provided in the waist end portion region 23 in the torso region T determined as a vertical direction range of each side seal portion 21 in which the front body F and the back body B are joined. The waist end portion elastic members 24 of the illustrated mode correspond to elongated elastic members such as a plurality of rubber threads disposed at intervals in the vertical direction, and apply a stretching force to tighten around the waist of the body. The waist end portion elastic members 24 are not disposed substantially in a bundle with a close spacing, and three or more, preferably five or more members are disposed at intervals of about 3 to 8 mm to form a predetermined stretchable zone. A stretch rate of the waist end portion elastic member 24 in fixing may be appropriately determined. However, the stretch rate may be set to about 230 to 320% in the case of normal adult use. One or a plurality of belt shaped elastic members may be used as the waist end portion elastic member 24.

The rubber threads are used as the waist end portion elastic member 24 in an illustrated example. However, for example, a tape shaped elastic member may be used, and an elastic film described below may be extended to the waist end portion region 23 instead of using the tape shaped elastic member. The waist end portion elastic member 24 in the illustrated mode is interposed in the folded part 20C formed by folding back a component of the second sheet layer 20B to the internal surface side at a waist opening edge. However, the waist end portion elastic member 24 may be interposed between a component of the first sheet layer 20A and the component of the second sheet layer 20B.

Figure 23:
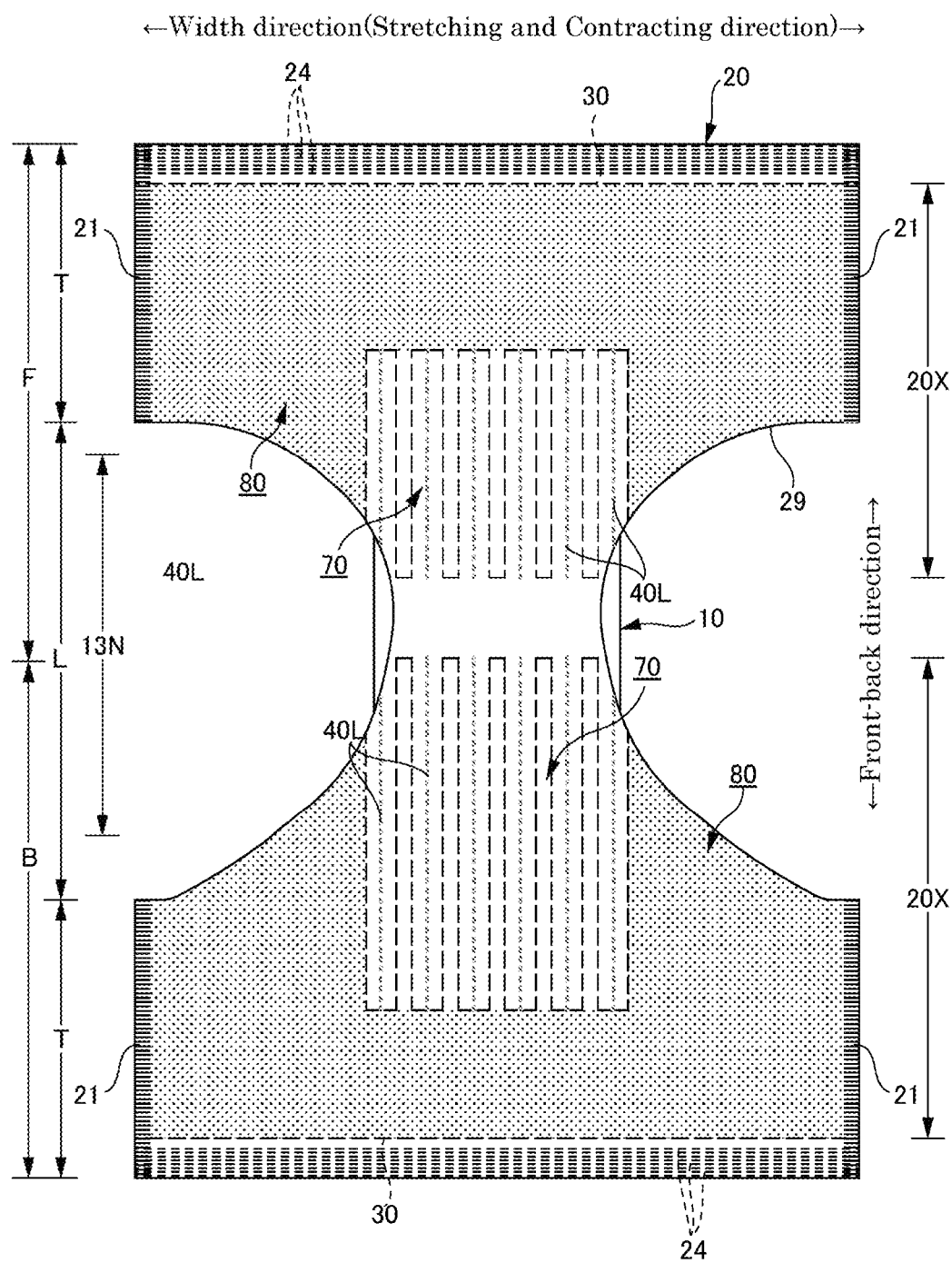
FIG. 23 is a plan view (external surface side) of the underpants-type disposable diaper in the completely spread state.

In this embodiment, as illustrated in FIG. 23, the elastic film stretchable structures 20X are formed in the torso region T of the front body F, the torso region T of the back body B and the intermediate region L therebetween in the outer body 20. That is, in the stretchable structure 20X of the outer body 20, the non-stretchable region 70 is formed in the intermediate portion in the width direction, which includes parts of the outer body 20 overlapping with the absorber 13 (the non-stretchable region 70 may entirely or partly overlap with the absorber 13 and preferably should contain the substantially entire fixed portion 10B of the inner member) as well as the stretchable regions 80 extend to both the side seal portions 21 in the width direction. The elastic film 30 is, as shown in FIG. 16 and FIGS. 5 to 7, stacked between the first sheet layer 20A and the second sheet layer 20B over the entire stretchable regions 80 and the non-stretchable region 70.

In the stretchable region 80, while the elastic film 30 is being stretched in the width direction, the first sheet layer 20A and the second sheet layer 20B are joined at a large number of sheet bond portions 40 arranged at intervals in the stretching and contracting direction and the direction orthogonal thereto (the width direction and the front-back direction in the underpants-type disposable diaper as in the illustrated mode) via the through holes 31 formed in the elastic sheet layer 30. In this case, it is desirable that the first sheet layer 20A is not and the second sheet layer 20B is not joined to the elastic film 30 (except for a melted and solidified material described below). However, joining is allowed. In the stretchable region 80, as illustrated in FIG. 7D, in the natural length state of the elastic film 30, the first sheet layer 20A and the second sheet layer 20B between each pair of adjacent sheet bond portions rise in a direction away from each other, and thus a contraction wrinkle 25 extending in a direction intersecting the stretching and contracting direction is formed. As illustrated in FIG. 7C, in a worn state of being stretching to some extent in the width direction, the contraction wrinkle 25 is left even though the contraction wrinkle 25 is stretched. In addition, as in the illustrated modes, when the first sheet layer 20A is not and the second sheet layer 20B is not joined to the elastic film 30 in a portion other than at least between the first sheet layer 20A and the second sheet layer 20B, as understood from FIG. 7C assuming the worn state and FIGS. 7A and 7B assuming a completely spread state of the first sheet layer 20A and the second sheet layer 20B, in these states, a gap is formed between each sheet bond portion 40 and each through hole 31 for the sheet bond portion in the elastic film 30, thus, air permeability is imparted due to the gap even when a material of the elastic film 30 corresponds to a non-porous film or a sheet. States of the contraction wrinkle 25 in the worn state and the natural length state are shown in sample photographs of FIG. 29 and FIG. 30. The elongation at the elastic limit of the stretchable region 80 may be adjusted by the area rate of the sheet bond portions 40. In general, the elongation at the elastic limit of the stretchable region 80 in the stretching and contracting direction is desirably set to 200% or more (preferably 265 to 295%).

Figure 25A:
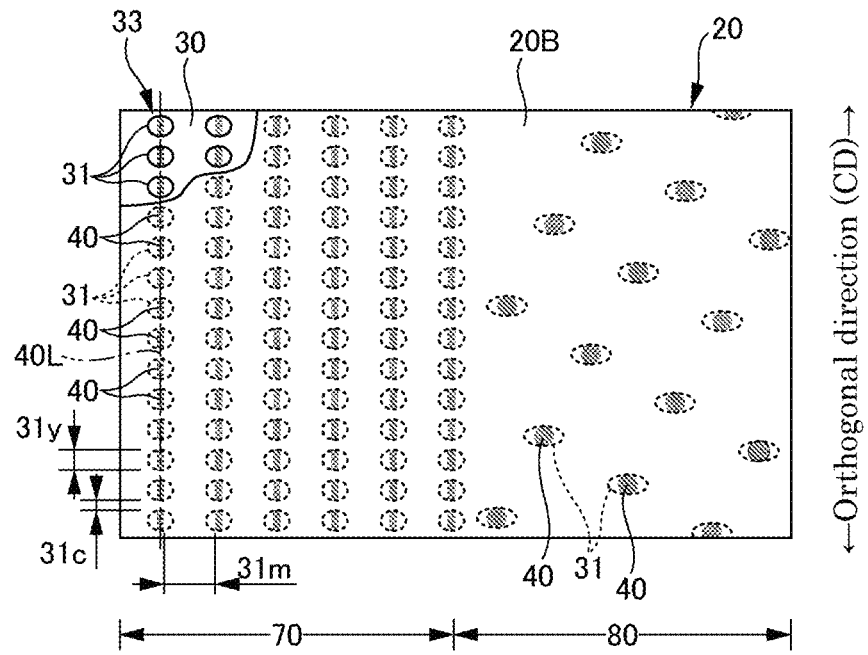
FIG. 25A is a partially fractured plan view illustrating a main part of the outer body in the completely spread state before cutting an elastic film.
Figure 25B:
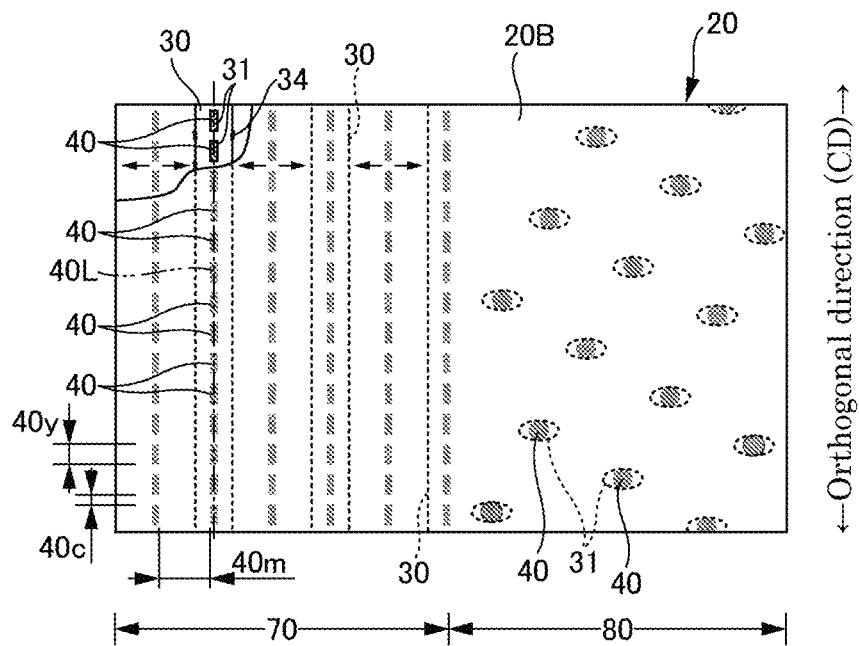
FIG. 25B is a partially fractured plan view illustrating the main part of the outer body in the completely spread state after cutting the elastic film.
Figure 27A:
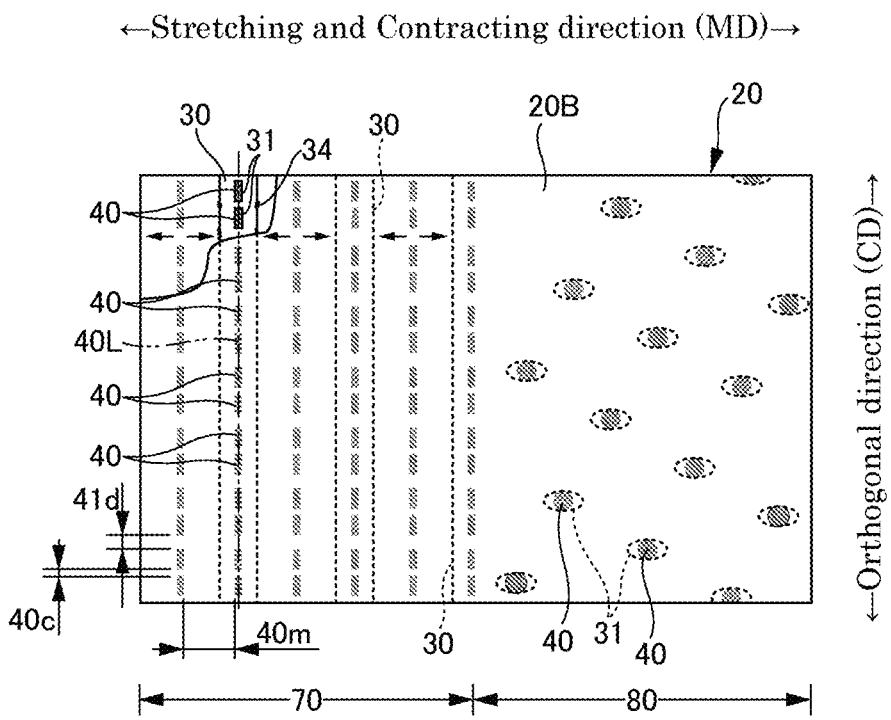
FIG. 27A is a partially fractured plan view illustrating a main part of the outer body in the completely spread state.
Figure 27B:
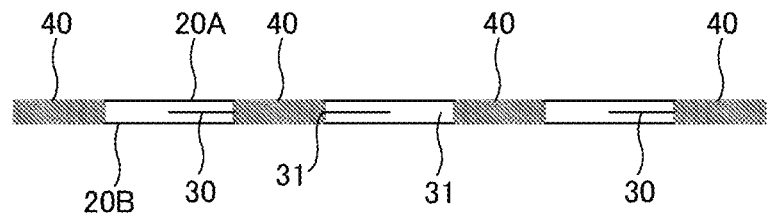
FIG. 27B is a cross-sectional view of a main part after cutting the elastic film.

In the non-stretchable region 70, as illustrated in FIG. 23, FIG. 25B, and FIG. 27B, the first sheet layer 20A and the second sheet layer 20B are joined by welding at rows 40L of a plurality of rows of sheet bond portions 40 which extends in a dotted line in the direction intersecting the stretching and contracting direction and is disposed at intervals in the stretching and contracting direction. Therefore, even though the first sheet layer 20A and the second sheet layer 20B are integrated by welding in the sheet bond portions 40, the sheet bond portions 40 are discontinuous, and thus a decrease in flexibility is prevented. Meanwhile, the elastic film 30 is cut along the rows 40L of the sheet bond portions 40, and portions at both sides of cut positions contract as indicated by arrows in the figure and are left at both sides of the rows 40L of the sheet bond portions 40 in the stretching and contracting direction in the natural length state. As a result, the non-stretchable region 70 corresponds to a region in which elasticity of the elastic film 30 is reliably eliminated and the elastic film 30 is discontinuous. Thus, air permeability is excellent. The elongation at the elastic limit in the stretching and contracting direction in the non-stretchable region 70 may be 130% or less, preferably 120% or less. In particular, according to the invention, the elongation at the elastic limit may be set to 100%. Characteristically, as understood from a comparison of FIG. 25A illustrating a state before fracture of perforation 33 and FIG. 25B and FIG. 27B illustrating a state after fracture of the perforation 33, a cut portion of the elastic film 30 is formed by fracture of the perforation 33 formed by melting in the elastic film 30. In other words, since the cut portion resulting from melting is discontinuous, a trace of cutting resulting from melting is discontinuous. Further, appearance is excellent, and a decrease in flexibility may be prevented. Reference symbol 34 in FIG. 25B indicates a portion in which the perforation 33 of the elastic film 30 is fractured.

The illustrated mode is formed by a manufacturing method described below, and the perforation 33 is formed by the through holes 31 formed by melting the elastic film 30 in a corresponding part using welding of the sheet bond portions 40. Thus, positions of the sheet bond portions 40 correspond to positions of the through holes 31 of the perforation 33, and only the sheet bond portions 40 correspond to the trace of cutting of the elastic film 30. Without forming the perforation 33 in the elastic film 30 by welding of the sheet bond portions 40, the perforation 33 may be formed in a separate elastic film 30, and the perforation 33 may be fractured.

In particular, in the non-stretchable region 70 of the illustrated mode, a plurality of rows of the sheet bond portions 40 is provided at intervals in the stretching and contracting direction, cut pieces of the elastic film 30 are left in a natural length state by straddling every other row of the respective rows of the sheet bond portions 40 in the stretching and contracting direction, and the first sheet layer 20A and the second sheet layer 20B are joined via the through holes 31 provided in a part of the rows of the sheet bond portions 40 in the cut pieces of the elastic film 30 (the through holes 31 of the perforation 33 which is left without being fractured). Therefore, as illustrated in FIG. 25B and FIG. 27, a cut piece which is free due to cutting in the elastic film 30 and in a natural length state is fixed by joining of the first sheet layer 20A and the second sheet layer 20B, and thus it is possible to prevent appearance or wearing feeling from being degraded due to movement of the cut piece. Unlike the illustrated mode, only one row of the sheet bond portions 40 may be formed in the middle in the width direction, and the elastic film 30 may be cut along the row of the sheet bond portions 40. However, in this case, the elastic film 30 is not fixed in the non-stretchable region 70, and movement is restricted by the sheet bond portions 40 in the stretchable region 80.

A shape of each of the sheet bond portions 40 and the through holes 31 in the natural length state may be set to an arbitrary shape such as a perfect circle, an ellipse, a polygon such as a rectangle (including a linear shape or a rounded corner), a star shape, a cloud shape, etc. In particular, when the perforation 33 is formed by melting the elastic film 30 in the corresponding site through welding of the sheet bond portions 40 as in the non-stretchable region 70 of the illustrated mode, the shape of the sheet bond portions 40 preferable corresponds to a rectangle having a long side along the direction intersecting the stretching and contracting direction such that the perforation 33 is easily fractured.

A size of each of the sheet bond portions 40 in the stretchable region 80 and the non-stretchable region 70 may be appropriately determined. However, when the size is excessively large, an influence of hardness of the sheet bond portions 40 on a sense of touch increases. When the size is excessively small, a joining area is small, and materials may not be sufficiently attached to each other. Thus, in general, an area of each of the sheet bond portions 40 is preferably set to about 0.14 to 3.5 mm². An area of an opening of each of the through holes 31 in the stretchable region 80 may be greater than or equal to that of each of the sheet bond portions 40 since the sheet bond portions 40 are formed via the through holes 31. However, the area is preferably set to about 1 to 1.5 times the area of each of the sheet bond portions 40. When the perforation 33 is included in the elastic film in the non-stretchable region 70 as in the illustrated mode, the area of the opening of each of the through holes 31 of the perforation 33 may be set to a similar size. The area of the opening of each of the through holes 31 refers to a value obtained when the stretchable structure 20X is in a natural length state, and refers to a minimum value in a case in which the area of the opening of each of the through holes 31 is not uniform in a thickness direction such as a case in which the area is different between a front side and a back side of the elastic film 30.

The area of each of the sheet bond portions and the area rate of the sheet bond portions 40 in each region may be appropriately determined. However, an elongation at an elastic limit is affected in the stretchable region 80. Thus, in general, the area and the area rate are preferably set to within the following ranges.

(Non-Stretchable Region 70)
Area of each of sheet bond portions 40: 0.14 to 3.5 mm² (particularly 0.4 to 3.0 mm²)
Area rate of sheet bond portions 40: 0.8 to 18.0% (particularly 1.0 to 10.6%)
(Stretchable Region 80)
Area of each of sheet bond portions 40: 0.14 to 3.5 mm² (particularly 0.14 to 1.0 mm²)
Area rate of sheet bond portions 40: 1.8 to 22.5% (particularly 1.8 to 10.6%)

The area rate of the sheet bond portions 40 may be changed by changing the number of sheet bond portions 40 per unit area or the area of each of the sheet bond portions 40. In a former case, the area of each of the sheet bond portions 40 may be the same or different between the non-stretchable region 70 and the stretchable region 80. In a latter case, the number of sheet bond portions 40 per unit area may be the same or different between the non-stretchable region 70 and the stretchable region 80.

A planar array of the sheet bond portions 40 and the through holes 31 in the stretchable region 80 may be appropriately determined. However, it is preferable to adopt a planar array in which the sheet bond portions 40 and the through holes 31 are regularly repeated. In addition to the planar array in which the sheet bond portions 40 and the through holes 31 are regularly repeated such as an oblique lattice shape illustrated in FIG. 21A, a hexagonal lattice shape illustrated in FIG. 21B (these shapes are also referred to as a staggered shape), a square lattice shape illustrated in FIG. 21C, a rectangular lattice shape illustrated in FIG. 21D, a parallel body lattice shape illustrated in FIG. 21E (a mode in which two groups are provided such that a large number of parallel oblique row groups intersect each other as illustrated in the figure), etc. (including a mode in which these shapes are inclined at an angle less than 90 degrees with respect to the stretching and contracting direction), it is possible to adopt a planar array in which a group of the sheet bond portions 40 (arrangement of a group unit may be regular or irregular, and a pattern, a letter shape, etc. may be used) is regularly repeated. An arrangement mode of the sheet bond portions 40 and the through holes 31 may be the same or different between the stretchable region 80 and the non-stretchable region 70.

A planar array of the sheet bond portions 40 in the non-stretchable region 70 is not restricted as long as the planar array corresponds to a pattern of one row extending in a dotted line in the direction intersecting the stretching and contracting direction or a plurality of rows, each of which is extending in a dotted line in the direction intersecting the stretching and contracting direction, and which are disposed at intervals in the stretching and contracting direction, that is, as long as gaps in each of which the first sheet layer 20A and the second sheet layer 20B are not joined, are formed between each pair of adjacent rows of the sheet bond portions 40 each having a dotted line shape, and the gaps continue in the direction intersecting the stretching and contracting direction.

In addition, dimensions of the perforation 33 for cutting the elastic film 30 in the non-stretchable region 70 may be appropriately determined. However, when the elastic film 30 having tensile strength and tensile elongation described below is used, a length $31y$ of the through holes 31 in a direction along the perforation 33 (a length of a so-called cut portion) is preferably set to 0.5 to 10 mm, particularly about 0.7 to 5 mm, an interval $31c$ of the adjacent two through holes 31 in the direction along the perforation 33 (a length of a so-called tie portion) is preferably set to 0.3 to 1 mm, particularly about 0.75 to 1 mm, a ratio thereof (a so-called cut/tie ratio) is preferably set to 1:2 to 10:1, and an interval $31m$ of the adjacent two through holes 31 in the stretching and contracting direction is preferably set to 1 to 20 mm, particularly about 3 to 10 mm. When the perforation 33 is formed by the through holes 31 formed by melting the elastic film 30 in the corresponding site by welding of the sheet bond portions 40 as in the illustrated mode, the length $31y$ of the through holes 31 in the direction along the perforation 33 is equal to the length $40y$ of the sheet bond portions 40 in the same direction, the interval $31c$ of the adjacent two through holes 31 in the direction along the perforation 33 is equal to the interval $40c$ of the adjacent two sheet bond portions 40 in the same direction, the interval $31m$ of the adjacent two through holes 31 in the stretching and contracting direction is equal to the interval $40c$ of the adjacent two sheet bond portions 40 in the same direction, and the sheet bond portions 40 may be formed to satisfy this condition of the through holes 31.

Figure 28:
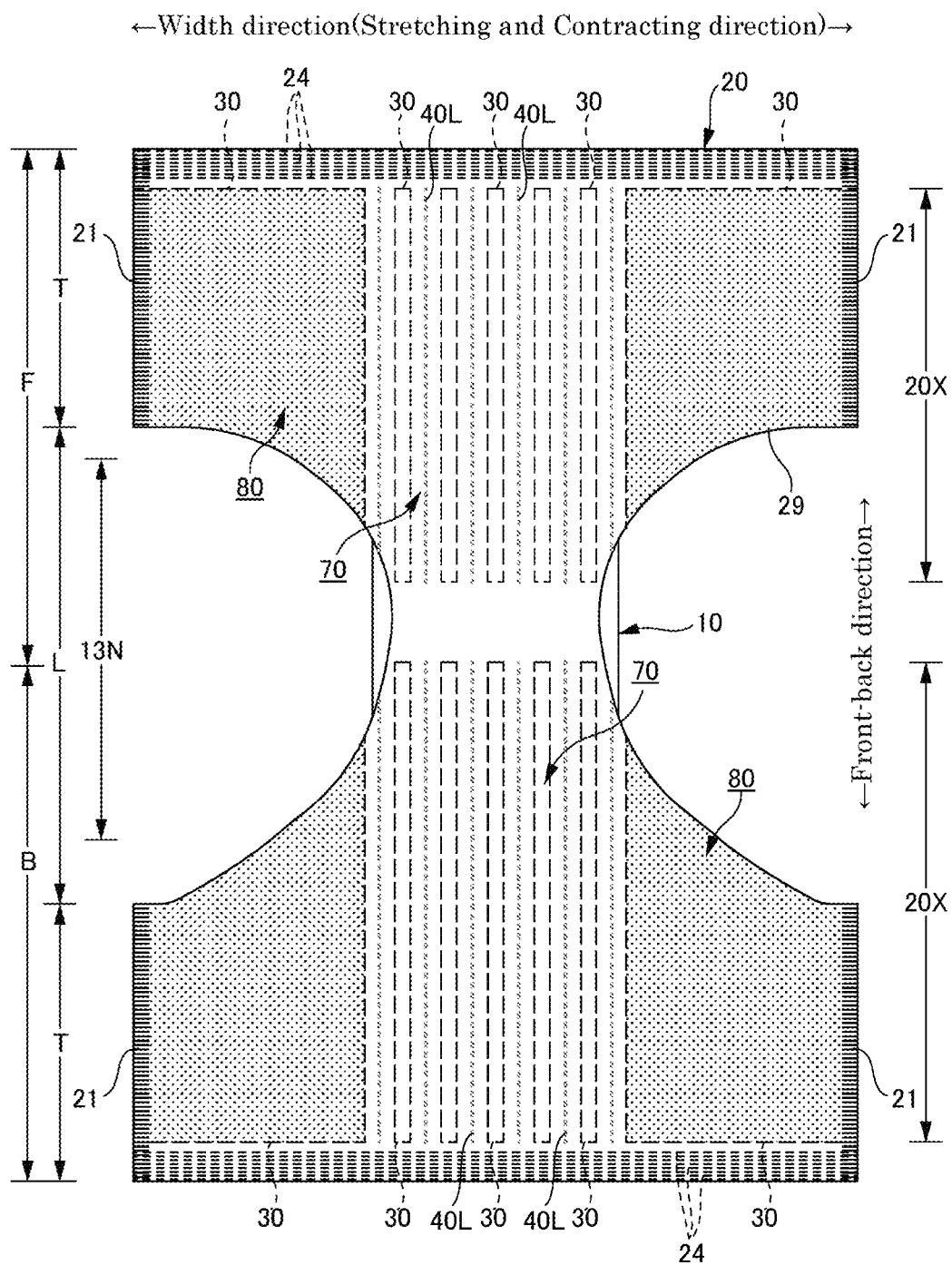
FIG. 28 is a plan view (external surface side) of the underpants-type disposable diaper in the fully stretched state.
Figure 29:
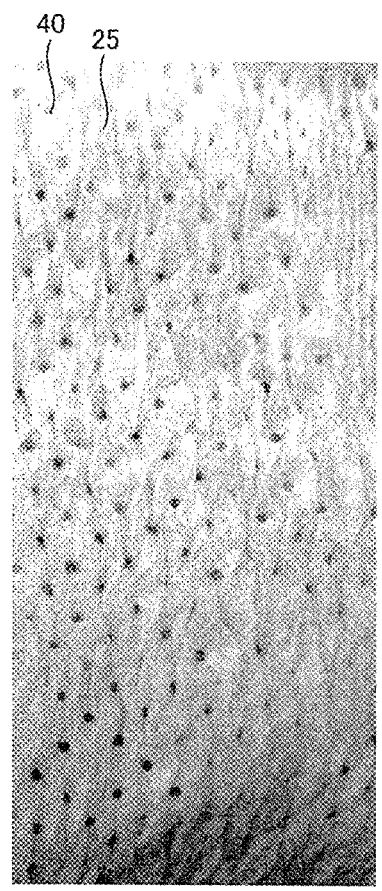
FIG. 29 is a photograph in a natural length state of a sample of an embodiment.
Figure 30:
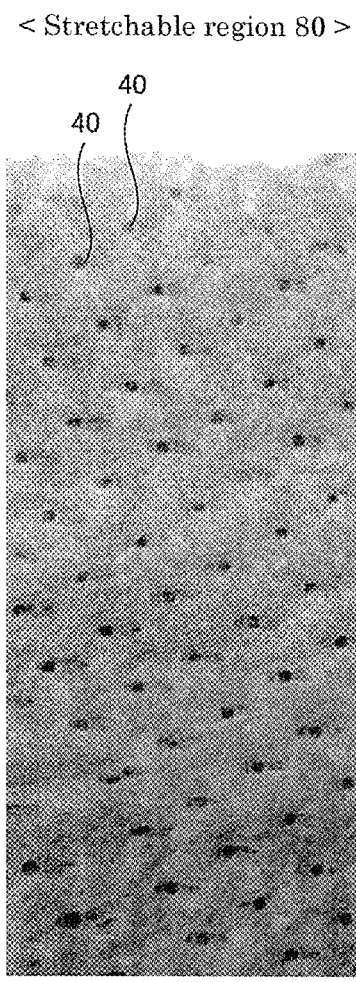
FIG. 30 is a photograph in a stretched state of the sample of the embodiment.
Figure 31:
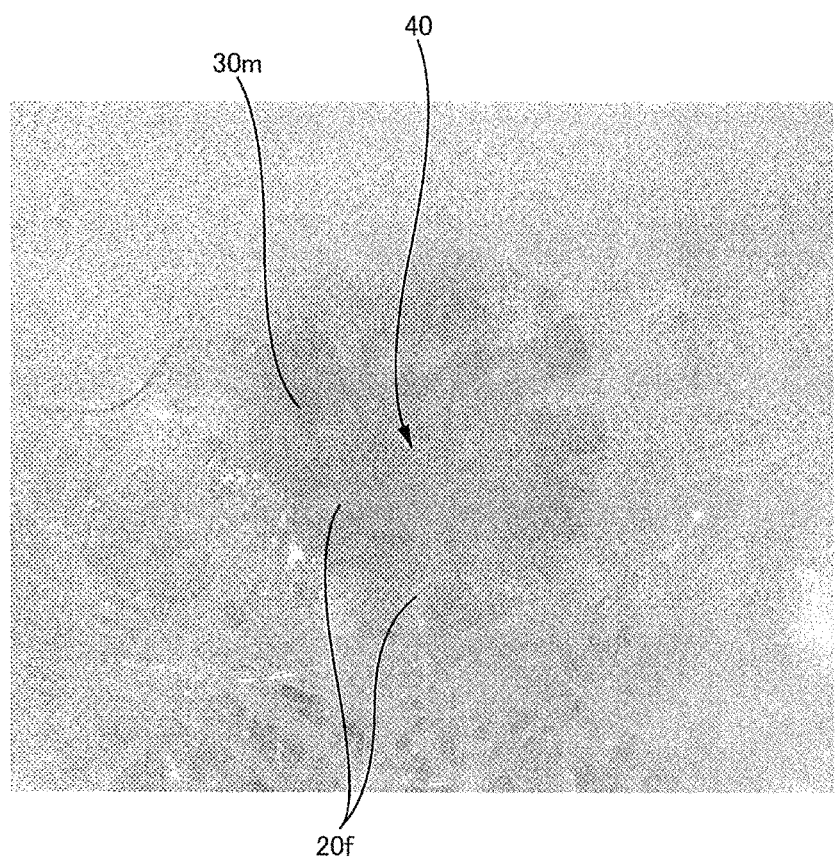
FIG. 31 is an enlarged photograph of a joint portion.
Figure 32:
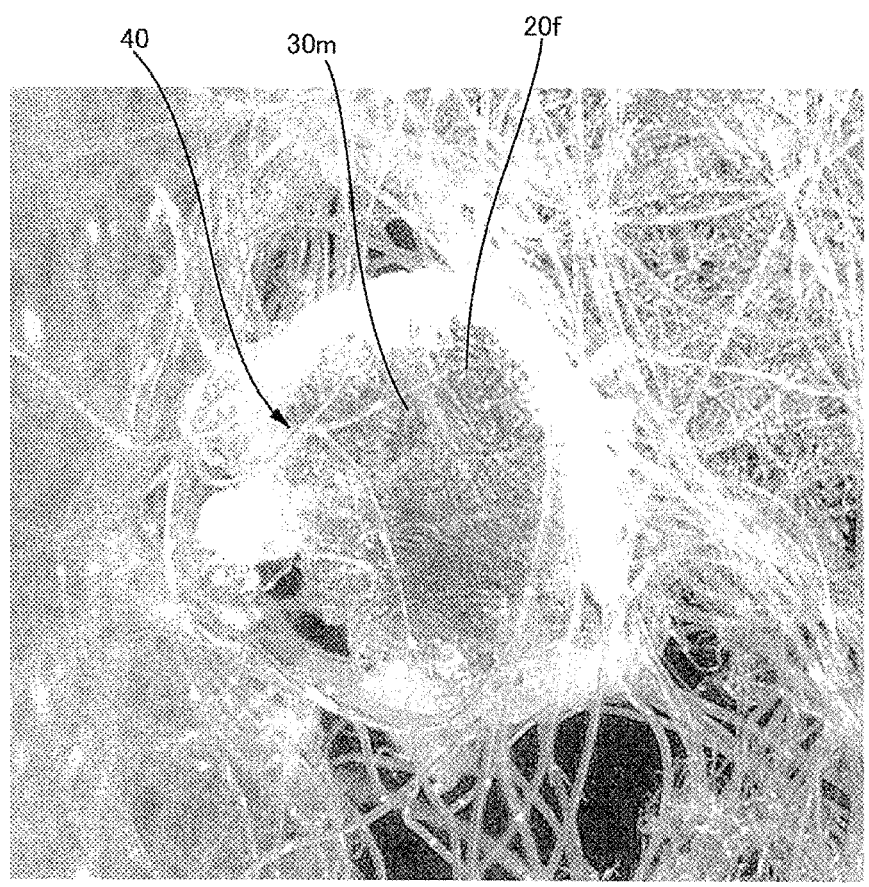
FIG. 32 is an enlarged photograph of the joint portion in a state in which a first sheet layer and a second sheet layer are peeled off

When the stretchable structure 20X of the elastic film 30 is formed to be wider than the non-stretchable region 70 in the direction intersecting the stretching and contracting direction, the elastic film 30 may be cut over the whole non-stretchable region 70 in the direction intersecting the stretching and contracting direction, and may not be completely cut from an end to another end in the direction intersecting the stretching and contracting direction in the elastic film 30. For example, as illustrated in FIG. 23, in the underpants-type disposable diaper, the non-stretchable region 70 is restricted to a portion overlapping the absorber 13, and a portion at a waist side thereof is set to the stretchable region 80 over the whole width direction in many cases. However, in such a case, as in the illustrated mode, the elastic film 30 may be provided in an integrated manner up to the waist side of the portion overlapping the absorber 13, and the elastic film 30 may be cut only in the portion overlapping the absorber 13. As illustrated in FIG. 28, the elastic film 30 may be completely cut from a front end to a back end such that the non-stretchable region 70 continues from an end of the elastic film 30 on the crotch side to an end thereof on the waist side.

Joining means for the first sheet layer 20A and the second sheet layer 20B in the sheet bond portions 40 is not particularly restricted. For example, the first sheet layer 20A and the second sheet layer 20B in the sheet bond portions 40 may be joined by a hot-melt adhesive, or by joining means based on material welding such as heat sealing, ultrasonic sealing, etc. When the joining means based on material welding is used, the through holes of the elastic film may be formed by protrusions, and the first sheet layer 20A and the second sheet layer 20B may be directly joined by welding at positions of the through holes as in Patent Literature 1. However, there is a concern that since the peeling strength is low, peeling may occur when a strong force is applied. In addition, in Patent Literature 1, since the through holes of the elastic film are formed by protrusions, the elastic film 30 is not left between the first sheet layer 20A and the second sheet layer 20B as illustrated in FIG. 24B, and there is a concern that protrusion debris (not illustrated) may be movably left around the through holes 31. In addition, unlike Patent Literature 1, as illustrated in FIG. 24C, joining the first sheet layer 20A and the second sheet layer 20B through the elastic film 30 without forming the through holes in the elastic film 30 may be taken into consideration. However, in this case, there is a problem that not only separation strength is low, and but also air permeability is extremely low since the through holes 31 are not included.

Figure 24A:
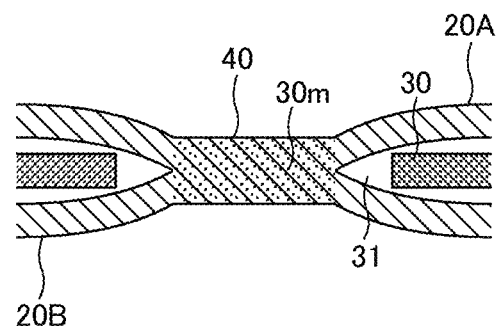
FIG. 24A, FIG. 24B and FIG. 24C are cross-sectional views, each schematically illustrating a cross section of a main part of the outer body stretched to some extent in a width direction.
Figure 24B:
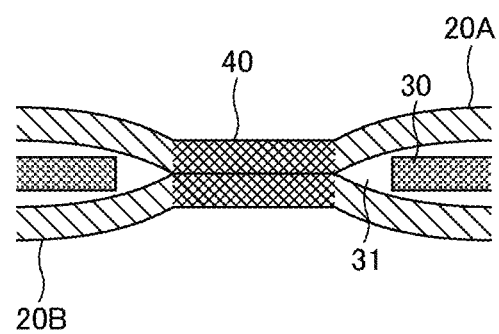
Figure 24C:
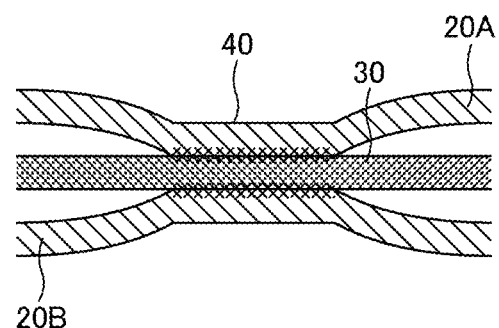

Therefore, when the joining means based on material welding is used, it is preferable to adopt a mode in which the first sheet layer 20A and the second sheet layer 20B in the sheet bond portions 40 are joined by at least the melted and solidified material 30m of the elastic film 30 among the first sheet layer 20A and the second sheet layer 20B as illustrated in FIG. 24A. When the first sheet layer 20A and the second sheet layer 20B are joined using the melted and solidified material 30m of the elastic film 30 as an adhesive as described above, separation strength is high, and it is possible to achieve both high air permeability and high separation strength.

Figure 33:
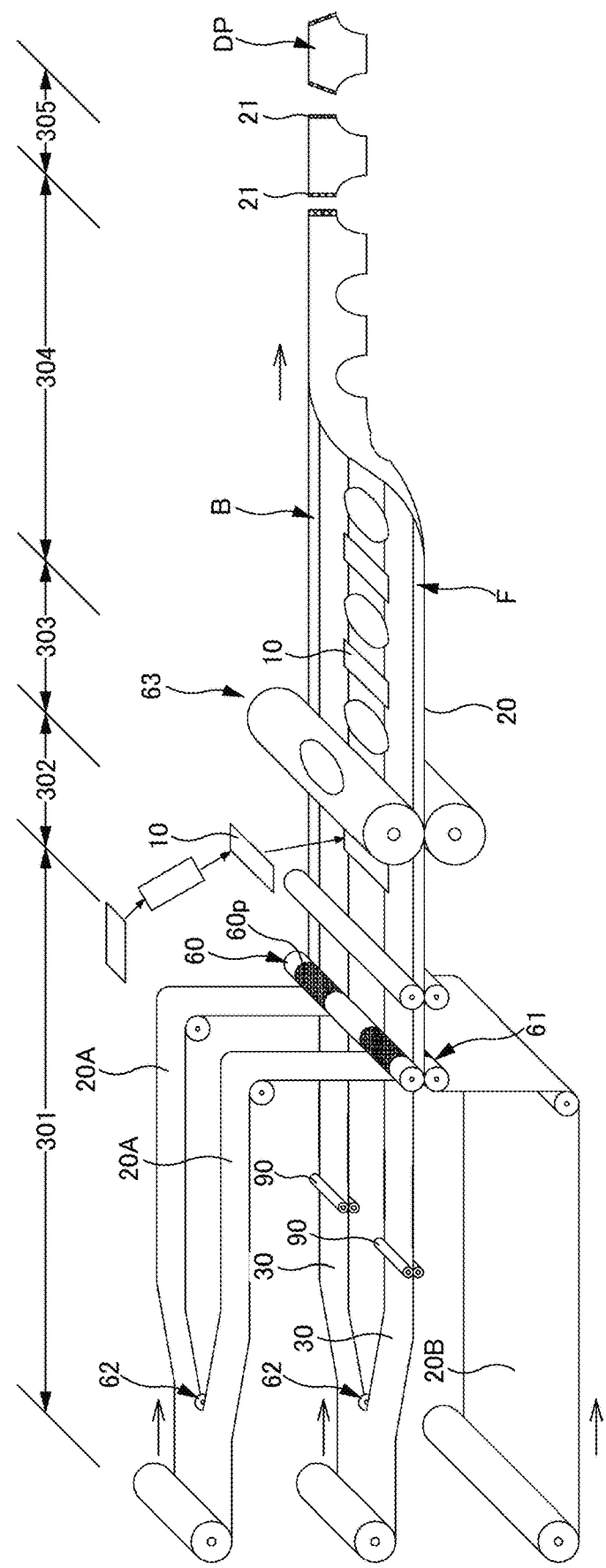
FIG. 33 is a schematic view illustrating a manufacturing flow of the underpants-type disposable diaper.
Figure 34:
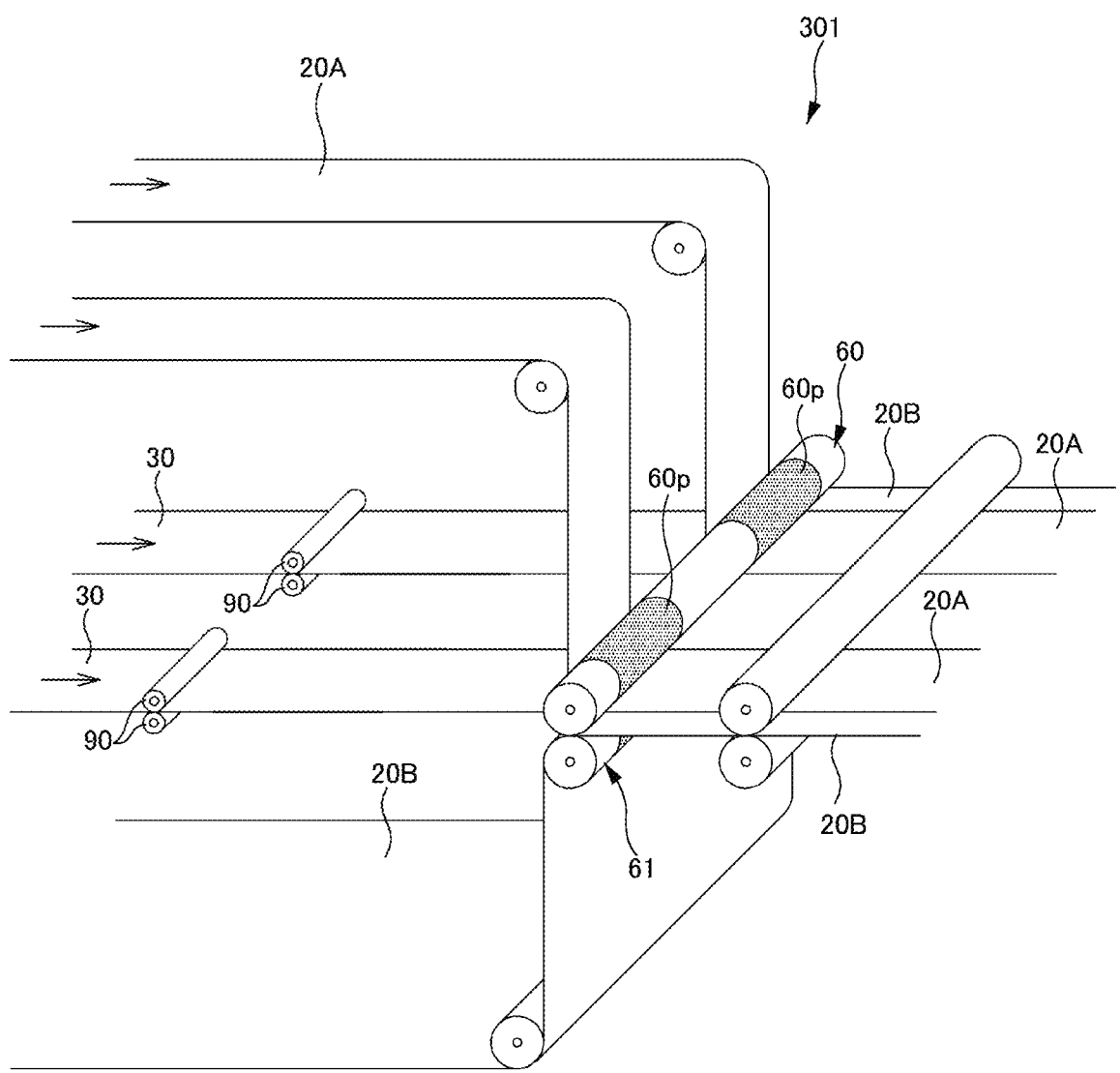
FIG. 34 is a schematic view of an outer body assembly process.

In such a joining structure, for example, when welding is performed in a predetermined pattern of the sheet bond portions 40 in the stretchable region 80 and the non-stretchable region 70 in a state in which the elastic film 30 is interposed between the first sheet layer 20A and the second sheet layer 20B while being stretched in the stretching and contracting direction at a substantially uniform stretch rate in the direction orthogonal to the stretching and contracting direction as illustrated in FIG. 33 and FIG. 34, the elastic film 30 is melted at a large number of positions to form the through holes 31. At the same time, manufacture may be simply and efficiently performed using a scheme of joining the first sheet layer 20A and the second sheet layer 20B by solidification of at least a melted material of the elastic film 30 at positions of the through holes 31. In the stretchable region 80 and the non-stretchable region 70 manufactured by this scheme, the shape/area of each of the sheet bond portions 40 is substantially equal to the shape/area of each of the through holes 31 in the natural length state.

Figure 26A:
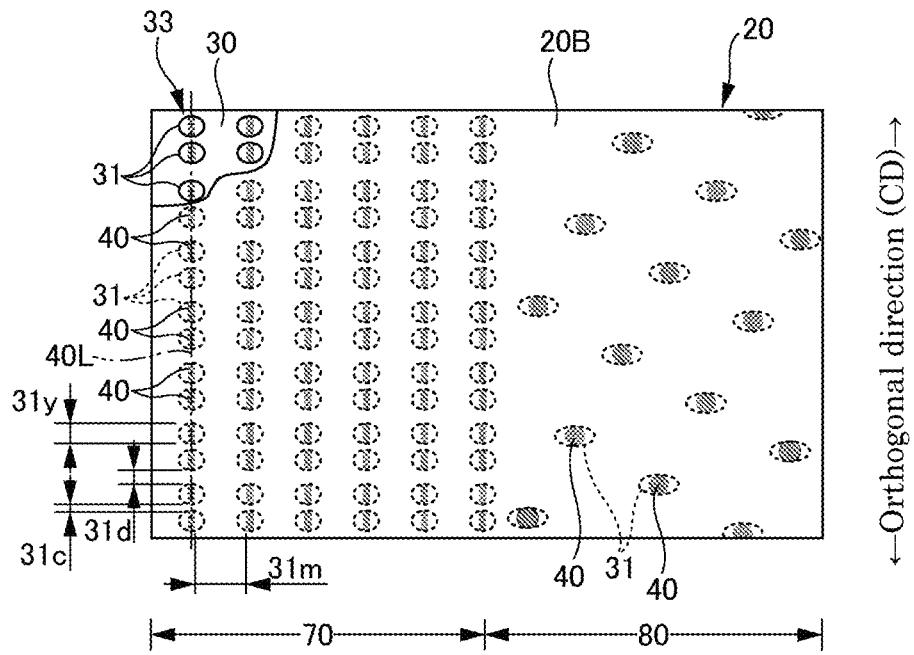
FIG. 26A is a partially fractured plan view illustrating a main part of the outer body in the completely spread state before cutting the elastic film.

When this scheme is adopted, a welding process is performed in a welding pattern corresponding to the row of the sheet bond portions 40 described above, that is, a welding pattern of a plurality of rows, each of which is extended in a dotted line shape in a CD, and which are disposed at intervals in an MD in the non-stretchable region 70. In this case, the elastic film 30 is melted in a welding pattern of extending in a dotted line shape, the through holes 31 are formed in a shape of the perforation 33 as illustrated in FIG. 25A and FIG. 26A, the first sheet layer 20A and the second sheet layer 20B are joined via the through holes 31 of the perforation 33 to form the sheet bond portions 40, and then the perforation 33 is fractured by a tensile force (line tension of a production line) applied by stretching the elastic film 30. In this way, as illustrated in FIG. 25B and FIG. 27, it is possible to form the above-described non-stretchable region 70 in which the elastic film 30 is cut.

Figure 26B:
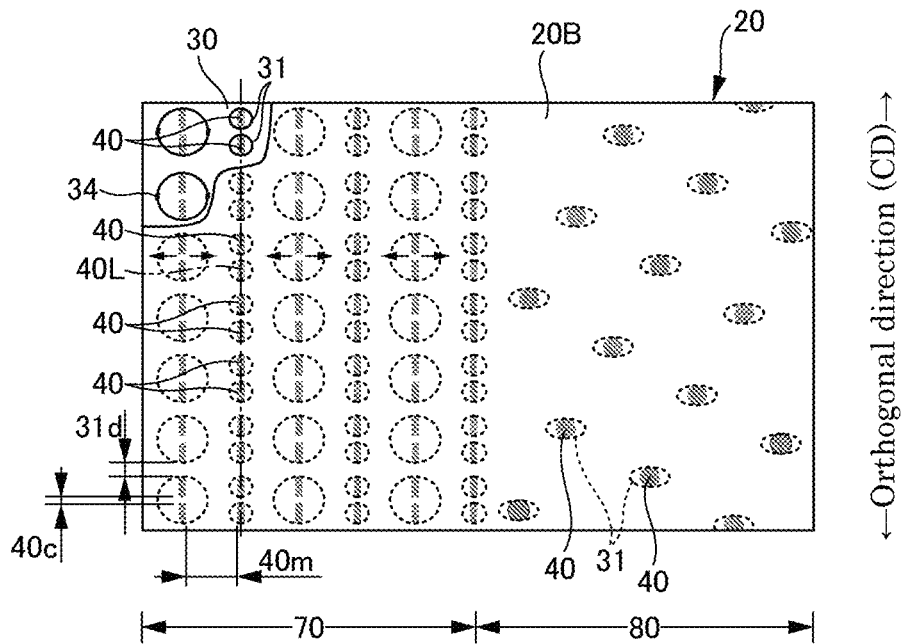
FIG. 26B is a partially fractured plan view illustrating the main part of the outer body in the completely spread state after partially cutting the elastic film.

In addition, when the perforation 33 is fractured by a tensile force applied by stretching the elastic film 30, there is a concern that the perforation 33 of the elastic film 30 may be fractured substantially at the same time with the welding process, and thus the elastic film 30 may not be continuously conveyed. Therefore, in a proposed scheme, to form the sheet bond portions 40 and the through holes 31 illustrated in FIG. 26A, a welding process is performed using a pattern having a portion in which an interval between the two adjacent welding points in the CD corresponds to a first interval (equal to an interval 40c of the adjacent two sheet bond portions 40 in each through hole and an interval 31c of the two adjacent through holes 31), and a portion corresponding to a second interval (equal to an interval 40d of the adjacent two sheet bond portions 40 and an interval 31d of the adjacent two through holes 31) wider than the first interval as a welding pattern of the dotted line. When the welding pattern of the dotted line described above is adopted, ties of perforation (tying portions each of which is provided between the two adjacent through holes 31) formed in the elastic film 30 become ties each having the same length as that of the first interval and ties each having the same length as that of the second interval. When the perforation 33 is fractured by the tensile force applied by stretching the elastic film 30, the ties each having the same length as that of the first interval are first fractured as illustrated in FIG. 26B, and then the ties each having the same length as that of the second interval are fractured as illustrated in FIG. 27A. Accordingly, it is possible to increase time taken from the welding process to fracturing the whole of the perforation 33 of the elastic film 30. Therefore, a situation can be prevented in which the perforation 33 of the elastic film 30 is fractured almost at the same time that the welding process is performed and thus the elastic film 30 cannot be continuously conveyed.

FIG. 33 illustrates an example of a method of manufacturing the underpants-type disposable diaper. This production line corresponds to a horizontal flow mode in which the width direction of the diaper is the MD (machine direction, line flow direction), and the outer body 20 is formed thereon. After the inner body 10 manufactured on another line is attached to the outer body 20, both side portions of front and back outer bodies 20 are joined by folding at a center in the front-back direction, and division into individual diapers DP is performed. For the sake of easy understanding, the same name and reference symbol as those of a member after manufacture are used for members that are continuous in a manufacturing process.

More specifically, this production line includes an outer body assembly process 301, an inner body attachment process 302, a leg opening punching process 303, a folding process 304, and a side portion joining/separation process 305. Among these processes, the outer body assembly process 301 is a characteristic process. In more detail, in the outer body assembly process 301, as enlarged and illustrated in FIG. 34, the first sheet layer 20A and the second sheet layer 20B continuing in a belt shape at a predetermined width are fed to sealing devices 60 and 61 and such that the first sheet layer 20A and the second sheet layer 20B are bonded along a continuing direction thereof, and the elastic film 30 continuing in a belt shape at a predetermined width passes through a nip roll 90 corresponding to a slower feed speed than speeds of the sealing devices 60 and 61 and are fed to the sealing devices 60 and 61 by being interposed between the first sheet layer 20A and the second sheet layer 20B in a state of being stretched in the MD due to a speed difference. In an illustrated mode, one sheet material is segmented into two parts by a slitter 62 to feed the first sheet layer 20A as separate front and back parts. However, the sheet material may be fed as separate front and back parts, and an integrated front and back sheet material may be fed similarly to the second sheet layer 20B without separating the first sheet layer 20A into front and back parts. Similarly, in the illustrated mode, one elastic film 30 is segmented into two parts by the slitter 62 to feed the elastic film 30 as separate front and back parts. However, the elastic film 30 may be fed as separate front and back parts, and an integrated front and back elastic film 30 may be fed without separating the elastic film 30 into front and back parts.

In the sealing devices 60 and 61, the first sheet layer 20A, the elastic film 30 stretched in the MD, and the second sheet layer 20B are interposed by a seal roll 60 having a large number of pressing protrusions 60p arranged in a pattern of the sheet bond portions 40 in the stretchable region 80 and the non-stretchable region 70 described above on an outer circumference surface, and an anvil roll 61 which is disposed to face the seal roll 60 and has a smooth surface. Further, the elastic film 30 is melted only sites where it is pressed in the thickness direction between the pressing protrusions 60p and an outer circumference surface of the anvil roll 61 by heating the pressing protrusions 60p, thereby forming the through holes 31, and the first sheet layer 20A and the second sheet layer 20B are bonded by welding at positions of the through holes 31. A heat sealing device is assumed to be used as the sealing devices 60 and 61 of the illustrated mode. However, it is possible to use another device such as an ultrasonic sealing device.

In the sealing devices 60 and 61, the outer body 20 in which the sheet bond portions 40 are formed is fractured by a tensile force (line tension of the production line) applied to the perforation 33 of the elastic film 30 by stretching the elastic film 30 at a downstream side of the sealing devices 60 and 61, and the outer body 20 having the stretchable region 80 and the non-stretchable region 70 in which the elastic film 30 is cut described above is formed. Thereafter, the underpants-type disposable diaper may be formed by adopting a known manufacturing process. In the illustrated mode, the inner body 10 manufactured on another line is fed at a predetermined interval in the MD to the outer body 20 formed through the sealing devices 60 and 61 in the inner body attachment process 302, and is joined to the outer body 20 using appropriate means such as a hot-melt adhesive, heat sealing, etc. In this way, inner assembly bodies 10 and 20 are formed. Subsequently, in the leg opening punching process 303, leg openings are formed in order by a cutter device 63. Then, in the folding process 304, the inner assembly bodies 10 and 20 are folded at a center in the CD (horizontal direction orthogonal to the MD). Then, in the side portion joining/separation process 305, the outer body 20 of the front body F and the outer body 20 of the back body B are joined at portions corresponding to both side portions of the individual diapers DP to form the side seal portions 21, and the outer body 20 is cut at a boundary of the individual diapers to obtain the individual diapers DP.

When the sheet bond portions 40 and the through holes 31 are simultaneously formed by welding as described above, it is possible to appropriately determine a relation of a melting point of the elastic film 30, melting points of the first sheet layer 20A and the second sheet layer 20B, and a processing temperature at a welding position. However, rather than to set the melting points of the first sheet layer 20A and the second sheet layer 20B to be lower than or equal to the melting point of the elastic film 30, melt and combine the whole of the first sheet layer 20A and the second sheet layer 20B and the whole elastic film 30 at the welding positions, and form the sheet bond portions 40, it is preferable to set the melting points of the first sheet layer 20A and the second sheet layer 20B to be higher than the melting point of the elastic film 30, melt the elastic film 30 at the welding position, and not to melt a part of the first sheet layer 20A and the second sheet layer 20B or not to melt a whole of the first sheet layer 20A and the second sheet layer 20B. In other words, as understood from FIG. 31 and FIG. 32, a latter case corresponds to a structure in which fibers 20f of the first sheet layer 20A and the second sheet layer 20B continuing from around the sheet bond portions 40 are left, and the first sheet layer 20A and the second sheet layer 20B are joined by the melted and solidified material 30m of the elastic film 30, which has infiltrated and solidified among the first sheet layer 20A and the second sheet layer 20B. Further, improved adhering of the melted and solidified material of the elastic film to the first sheet layer and the second sheet layer is obtained, and strength of the first sheet layer 20A and the second sheet layer 20B rarely decreases. Thus, peeling strength is further enhanced. This situation in which "a part of the first sheet layer 20A and the second sheet layer 20B is not melted" includes a mode in which for all fibers of the sheet bond portions 40, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

From this point of view, the melting point of the elastic film 30 is preferably about 80 to 145° C., melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 80° C.

Figure 22:
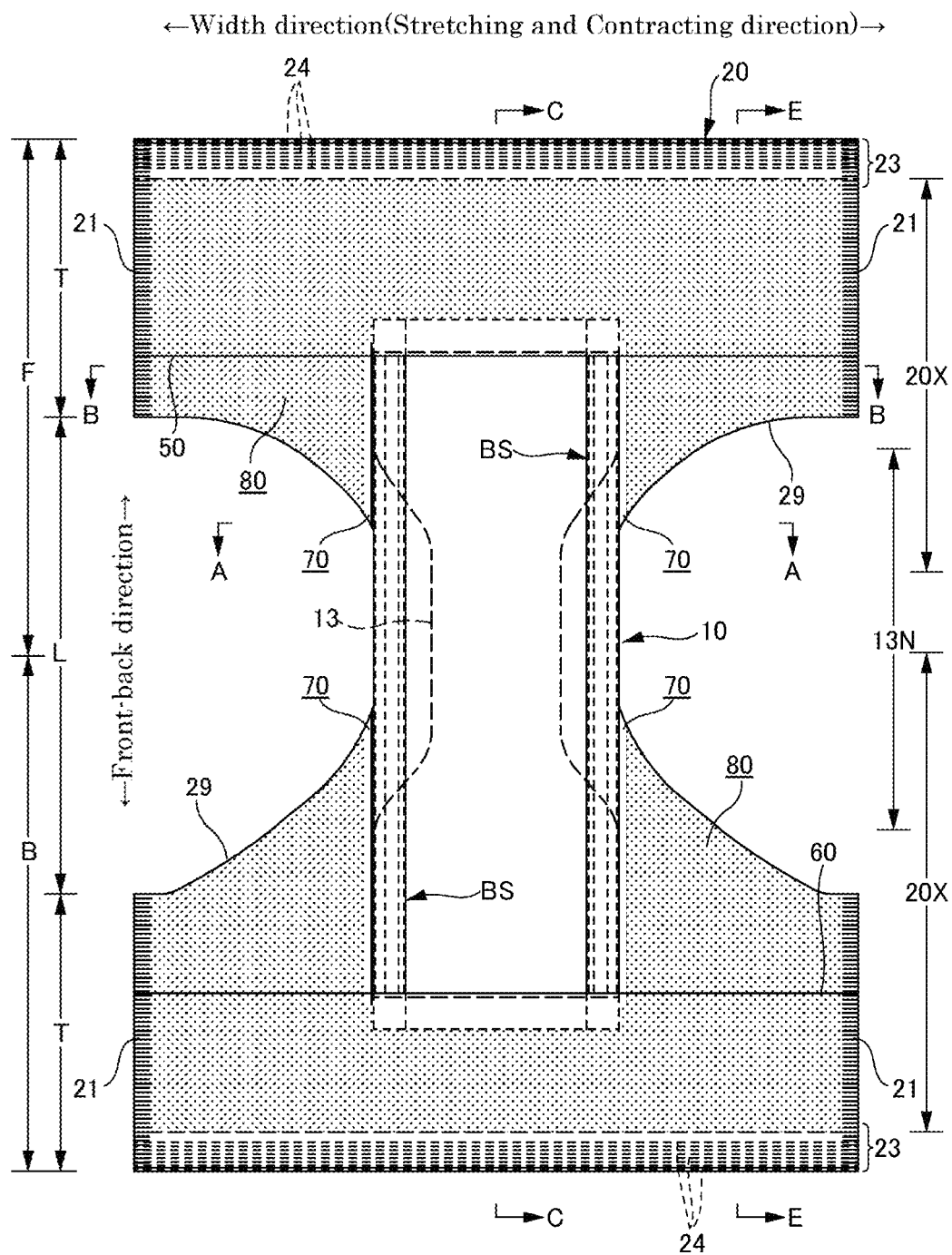
FIG. 22 is a plan view (internal surface side) of the underpants-type disposable diaper in a completely spread state.

Meanwhile, an example illustrated in FIG. 22 and FIG. 23 is an example in which the elastic film stretchable structure 20X is applied to a stretchable structure other than the waist end portion region 23 of the outer body 20. However, appropriate changes are allowed. For example, the waist end portion region 23 may be included at the time of application as in the example illustrated in FIG. 1 and FIG. 2 and the example illustrated in FIG. 33, or it is possible to adopt a mode in which the elastic film stretchable structure 20X is not provided in the intermediate region L between the torso region T of the front body F and the torso region T of the back body B. In addition, the above-described stretchable structure 20X may be applied to another elastic portion such as a three-dimensional gather, a plane gather, etc. generally used for a waist portion, a fastening tape, and an absorbent article of a tape-type disposable diaper in addition to the underpants-type disposable diaper. In addition, even though the non-stretchable region 70 is included in the present embodiment, it is possible to adopt a mode in which the whole stretchable structure 20X of the elastic film 30 is used as the stretchable region 80 and the non-stretchable region 70 is not included. Furthermore, even though the stretching and contracting direction is regarded as the width direction in the illustrated example, the stretching and contracting direction may be set to front-back direction or set to both the width direction and the front-back direction.

<Third Mode>

Next, a third mode will be described with reference to FIG. 3, FIG. 5 to FIG. 7, FIG. 16, FIG. 21, FIG. 22, FIG. 24, FIG. 31 to FIG. 34, and FIG. 35 to FIG. 41. In the outer body 20, as illustrated in FIG. 16, FIG. 5, and FIG. 6, the elastic film 30 and the elongated elastic member 24 along the width direction are arranged between the first sheet layer 20A and the second sheet layer 20B, and elasticity in the width direction is imparted. The planar shape of the outer body 20 corresponds to a pseudo-hourglass shape as a whole due to the concave leg lines 29 formed to form leg openings at intermediate both side portions, respectively. The outer body 20 may be divided into two front and back parts, and the both parts may be separated from each other in the front-back direction in the crotch portion.

More specifically, in the outer body 20 of the illustrated mode, the waist end portion elastic member 24 is provided in the waist end portion region 23 in the torso region T determined as a vertical direction range of each side seal portion 21 in which the front body F and the back body B are joined. The waist end portion elastic members 24 of the illustrated mode correspond to elongated elastic members such as a plurality of rubber threads disposed at intervals in the vertical direction, and apply a stretching force to tighten around the waist of the body. The waist end portion elastic members 24 are not disposed substantially in a bundle with a close spacing, and three or more, preferably five or more members are disposed at intervals of about 3 to 8 mm to form a predetermined stretchable zone. A stretch rate of the waist end portion elastic member 24 in fixing may be appropriately determined. However, the stretch rate may be set to about 230 to 320% in the case of normal adult use. One or a plurality of belt shaped elastic members may be used as the waist end portion elastic member 24.

The rubber threads are used as the waist end portion elastic member 24 in an illustrated example. However, for example, a tape shaped elastic member may be used, and an elastic film described below may be extended to the waist end portion region 23 instead of using the tape shaped elastic member. The waist end portion elastic member 24 in the illustrated mode is interposed in the folded part 20C formed by folding back a component of the second sheet layer 20B to the internal surface side at the waist opening edge. However, the waist end portion elastic member 24 may be interposed between a component of the first sheet layer 20A and the component of the second sheet layer 20B.

Figure 35:
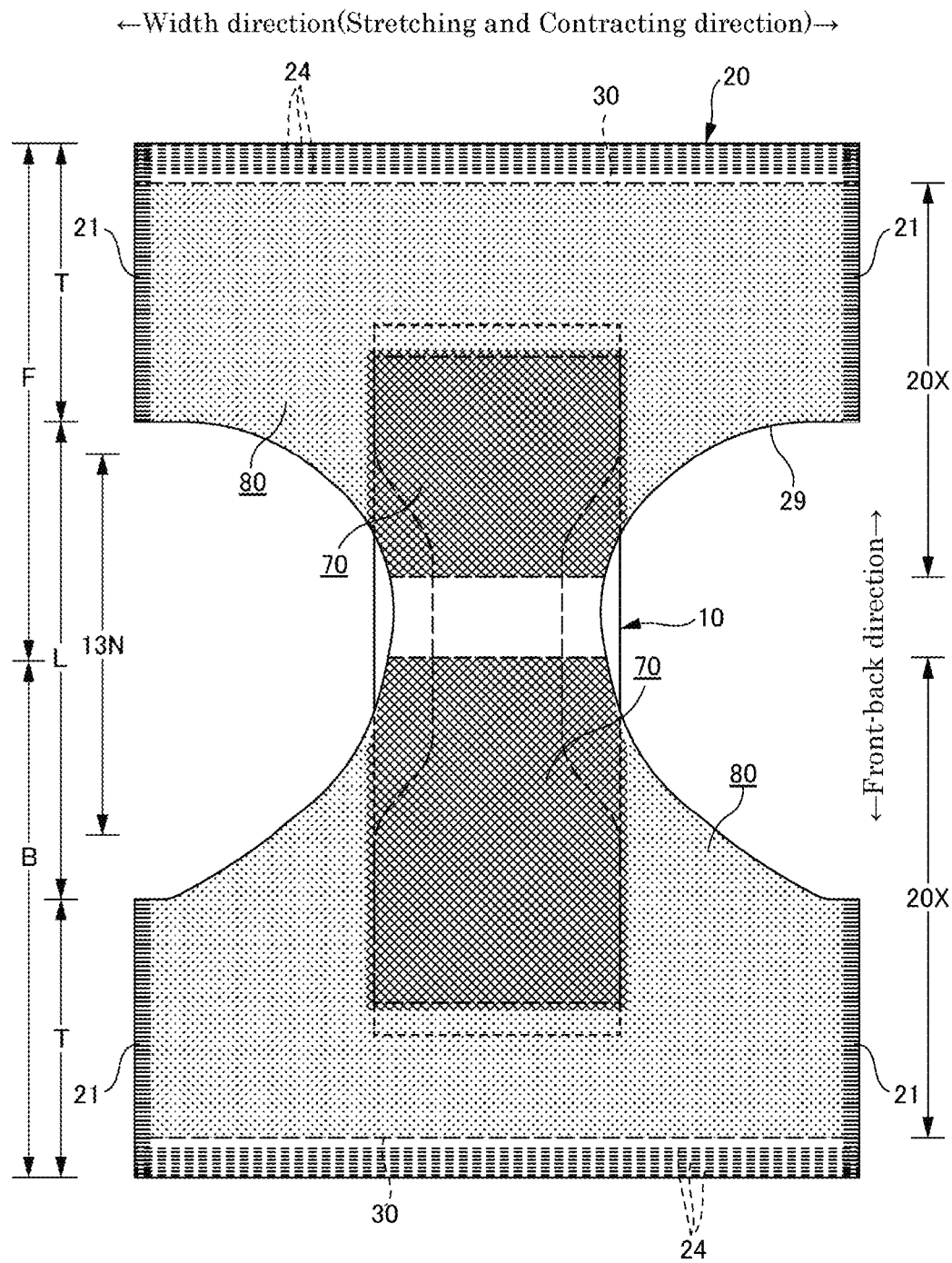
FIG. 35 is a schematic plan view of a main part of the outer body in the completely spread state.

In the present mode, as illustrated in FIG. 35 (a plan view on the internal surface side corresponding thereto is FIG. 22), the elastic film stretchable structure 20X is formed in the torso region T of the front body F and the torso region T of the back body B in the outer body 20, and the intermediate region L therebetween. That is, in the stretchable structure 20X of the outer body 20, the non-stretchable region 70 is provided in an intermediate portion in the width direction including a portion overlapping the absorber 13 (which may be a part or a whole of the overlapping portion, and desirably includes substantially the whole inner body fixed part 10B), and a portion extended to both the side seal portions 21 at both sides thereof in the width direction corresponds to the stretchable region 80. Further, over the whole of the stretchable region 80 and the non-stretchable region 70, as illustrated in FIG. 16 and FIG. 5 to FIG. 7, the elastic film 30 is stacked between the first sheet layer 20A and the second sheet layer 20B, and the first sheet layer 20A and the second sheet layer 20B are joined via the through holes 31 formed in the elastic film 30 by the large number of sheet bond portions 40 arranged at intervals in the stretching and contracting direction and the direction orthogonal thereto (the width direction and the front-back direction in the underpants-type disposable diaper as in the illustrated mode) in a state in which the elastic film 30 is stretched in the width direction. In this case, it is desirable that the first sheet layer 20A is not and the second sheet layer 20B is not joined to the elastic film 30 (except for a melted and solidified material described below). However, joining is allowed.

In the stretchable region 80, as illustrated in FIG. 7D, in the natural length state of the elastic film 30, the first sheet layer 20A and the second sheet layer 20B between each pair of adjacent sheet bond portions rise in a direction away from each other, and thus a contraction wrinkle 25 extending in a direction intersecting the stretching and contracting direction is formed. As illustrated in FIG. 7C, in a worn state of being stretching to some extent in the width direction, the contraction wrinkle 25 is left even though the contraction wrinkle 25 is stretched. In addition, as in the illustrated modes, when the first sheet layer 20A is not and the second sheet layer 20B is not joined to the elastic film 30 in a portion other than at least between the first sheet layer 20A and the second sheet layer 20B, as understood from FIG. 7C assuming the worn state and FIGS. 7A and 7B assuming a completely spread state of the first sheet layer 20A and the second sheet layer 20B, in these states, a gap is formed between each sheet bond portion 40 and each through hole 31 for the sheet bond portion in the elastic film 30, thus, air permeability is imparted due to the gap even when a material of the elastic film 30 corresponds to a non-porous film or a sheet. States of the contraction wrinkle 25 in the worn state and the natural length state are shown in sample photographs of FIG. 40 and FIG. 41. The elongation at the elastic limit of the stretchable region 80 may be adjusted by the area rate of the sheet bond portions 40. In general, the elongation at the elastic limit of the stretchable region 80 in the stretching and contracting direction is desirably set to 200% or more (preferably 265 to 295%).

Figure 36A:
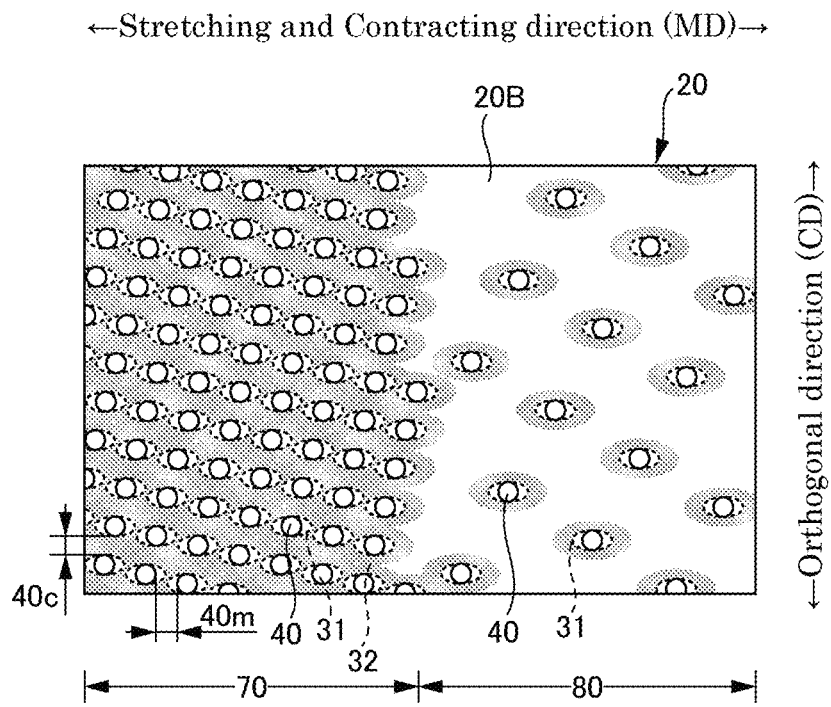
FIG. 36A and FIG. 36B are enlarged plan views of a main part illustrating a pattern of joint portions.
Figure 36B:
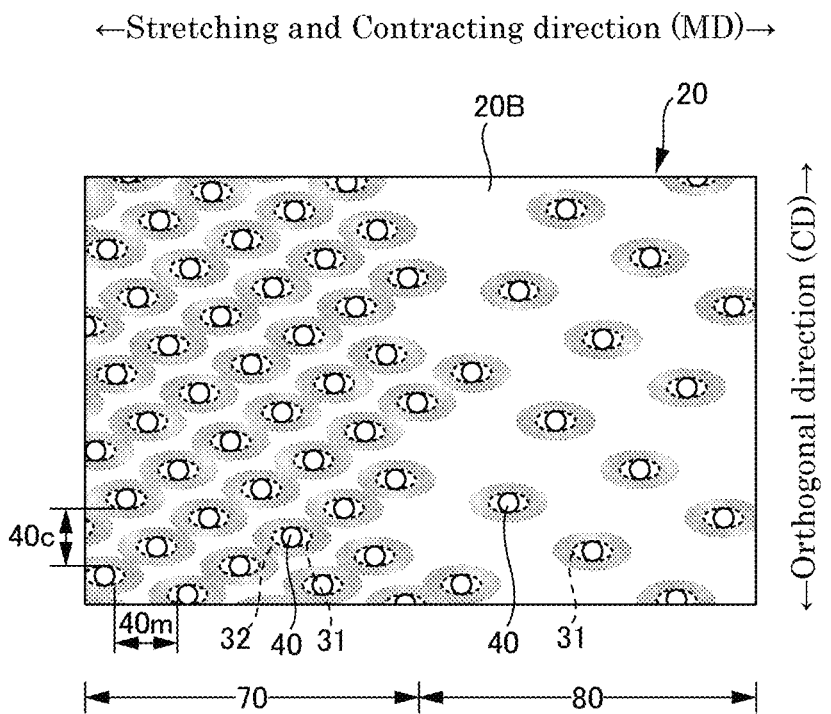

Characteristically, as illustrated in FIG. 36, since the area rate of the sheet bond portions 40 in the non-stretchable region 70 is higher than that in the stretchable region 80, and a part or total of a portion formed among the through holes 31 in the elastic film 30 is set to a thermal deterioration portion 32 in which elasticity is decreased due to thermal deterioration, an elongation at an elastic limit in the stretching and contracting direction is set to 130% or less (preferably 120% or less, more preferably 100%). In the non-stretchable region 70, as understood from the sample photographs of FIG. 40 and FIG. 41, a portion raised in a stripe shape or an extremely fine wrinkle is formed between the two adjacent sheet bond portions 40. However, since the area rate of the sheet bond portions 40 is significantly high, and the portion formed among the sheet bond portions 40 corresponds to the thermal deterioration portion 32 due to thermal deterioration of the elastic film 30, elasticity is substantially eliminated. Furthermore, continuity of the elastic film 30 in the stretchable region 80 and the non-stretchable region 70 may be maintained, and the appearance becomes excellent.

A shape of each of the sheet bond portions 40 and the through holes 31 in the natural length state may be set to an arbitrary shape such as a perfect circle, an ellipse, a polygon such as a rectangle (including a linear shape or a rounded corner), a star shape, a cloud shape, etc.

A size of each of the sheet bond portions 40 may be appropriately determined. However, when the size is excessively large, an influence of hardness of the sheet bond portions 40 on a sense of touch increases. When the size is excessively small, a joining area is small, and materials may not be sufficiently attached to each other. Thus, in general, an area of each of the sheet bond portions 40 is preferably set to about 0.14 to 0.75 mm$^2$. An area of an opening of each of the through holes 31 may be greater than or equal to that of the sheet bond portions since the sheet bond portions are formed via the through holes 31. However, the area is preferably set to about 1 to 1.5 times the area of each of the sheet bond portions 40. The area of the opening of each of the through holes 31 refers to a value obtained when the stretchable structure 20X is in the natural length state, and refers to a minimum value in a case in which the area of opening of each of the through holes 31 is not uniform in a thickness direction such as a case in which the area is different between a front side and a back side of the elastic film 30.

In general, the area of each of the sheet bond portions and the area rate of the sheet bond portions 40 in each region are preferably set to as below.

(Non-Stretchable Region 70)

Area of each of sheet bond portions 40: 0.14 to 0.75 mm$^2$ (particularly 0.14 to 0.35 mm$^2$)

Area rate of sheet bond portions 40: 8 to 17% (particularly 9 to 14%)

(Stretchable Region 80)

Area of each of sheet bond portions 40: 0.14 to 3.5 mm$^2$ (particularly 0.14 to 1.0 mm$^2$)

Area rate of sheet bond portions 40: 1.8 to 19.1% (particularly 1.8 to 10.6%)

Figure 37A:
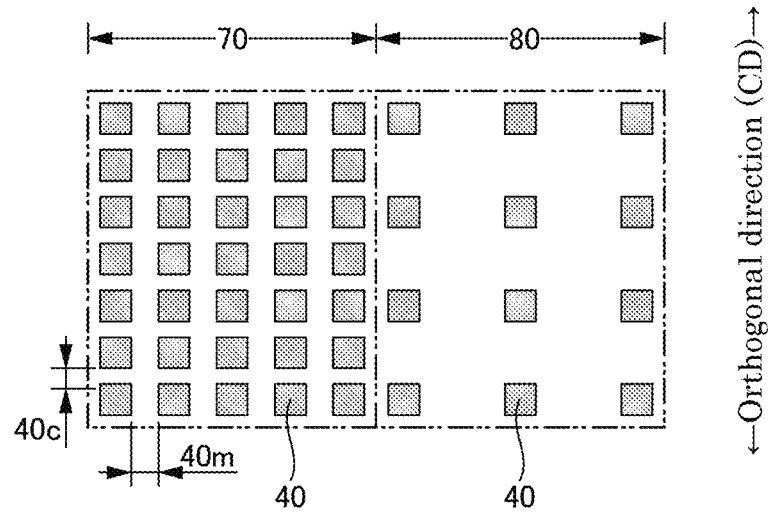
FIG. 37A and FIG. 37B are enlarged plan views of a main part illustrating a pattern of joint portions.
Figure 37B:
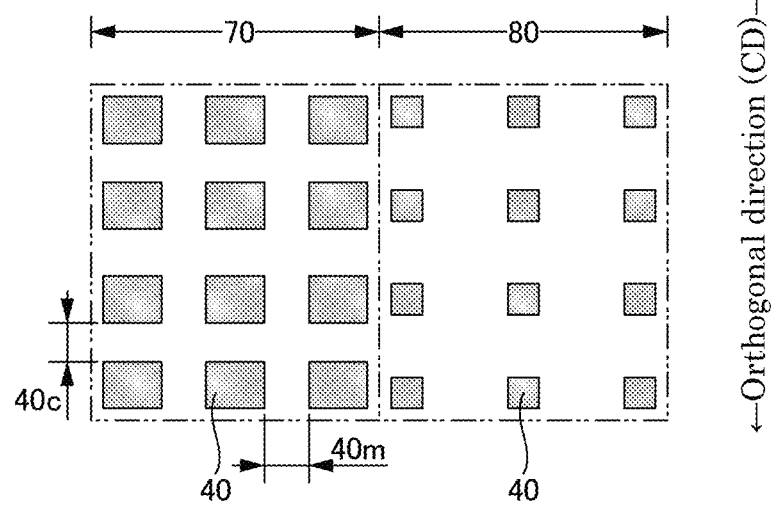

When the area rate of the sheet bond portions 40 is made different between the non-stretchable region 70 and the stretchable region 80 as described above, the number of sheet bond portions 40 per unit area may be changed as illustrated in FIG. 37A, or the area of each of the sheet bond portions 40 may be changed as illustrated in FIG. 37B. In a former case, the area of each of the sheet bond portions 40 may be the same or different between the non-stretchable region 70 and the stretchable region 80. In a latter case, the number of sheet bond portions 40 per unit area may be the same or different between the non-stretchable region 70 and the stretchable region 80.

A planar array of the sheet bond portions 40 and the through holes 31 may be appropriately determined. However, it is preferable to adopt a planar array in which the sheet bond portions 40 and the through holes 31 are regularly repeated. In addition to the planar array in which the sheet bond portions 40 and the through holes 31 are regularly repeated such as an oblique lattice shape illustrated in FIG. 21A, a hexagonal lattice shape illustrated in FIG. 21B (these shapes are also referred to as a staggered shape), a square lattice shape illustrated in FIG. 21C, a rectangular lattice shape illustrated in FIG. 21D, a parallel body lattice shape illustrated in FIG. 21E (a mode in which two groups are provided such that a large number of parallel oblique row groups intersect each other as illustrated in the figure), etc. (including a mode in which these shapes are inclined at an angle less than 90 degrees with respect to the stretching and contracting direction), it is possible to adopt a planar array in which a group of the sheet bond portions 40 (arrangement of a group unit may be regular or irregular, and a pattern, a letter shape, etc. may be used) is regularly repeated. An arrangement mode of the sheet bond portions 40 and the through holes 31 may be the same or different between the stretchable region 80 and the non-stretchable region 70.

Figure 38:
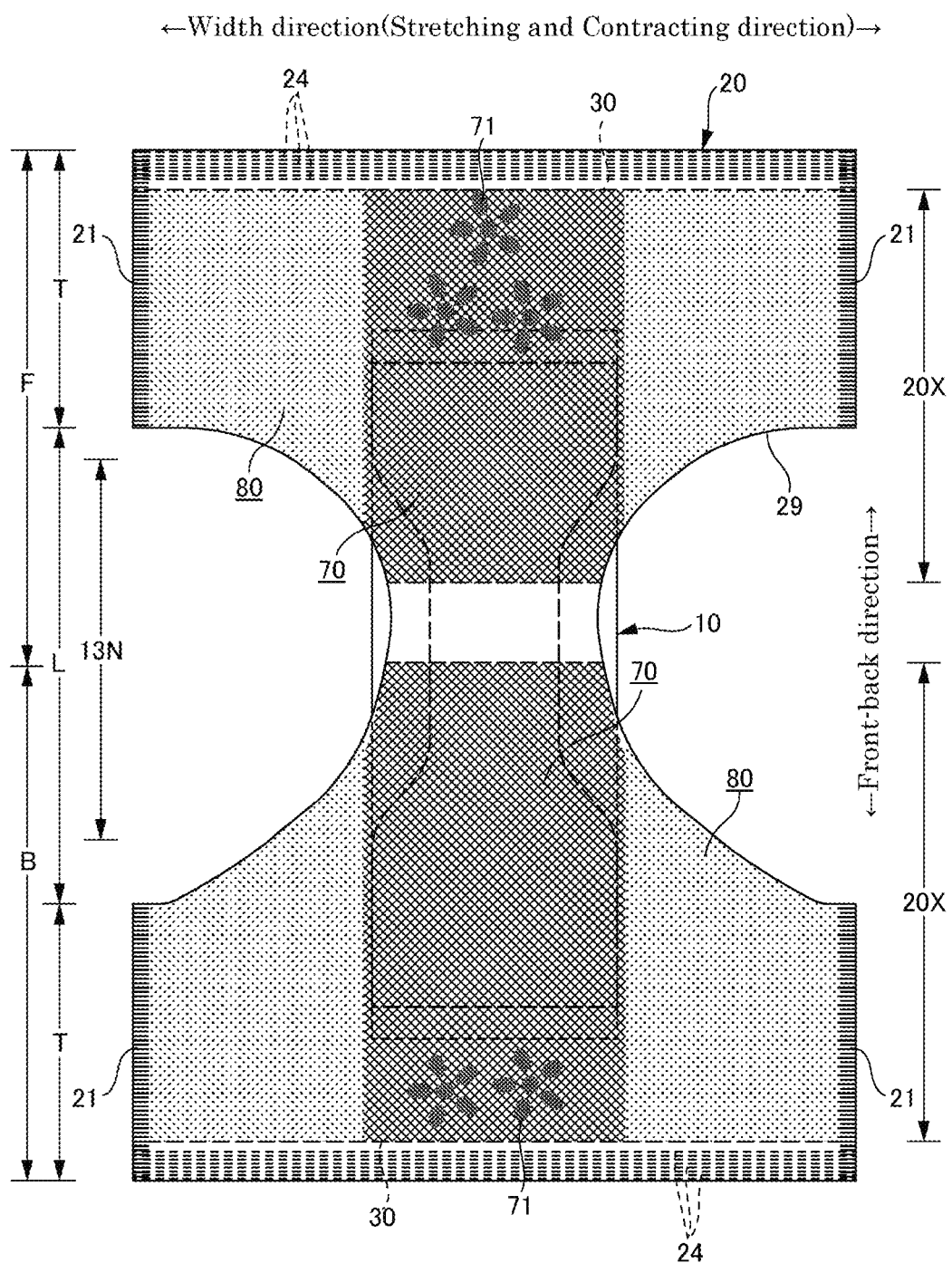
FIG. 38 is a plan view (external surface side) of the underpants-type disposable diaper in the completely spread state.

As illustrated in FIG. 38, in addition to the portion overlapping the absorber 13, for example, it is possible to provide the non-stretchable region 70 in which the sheet bond portions 40 are disposed in a shape of an indication 71. The indication 71 may correspond to an indication known in a field of the absorbent article, for example, a pattern for decoration (including a tiny picture or a character), a function indicator such as a usage method, usage assistance, a size, etc., or a mark indication such as a manufacturer, a product name, a characteristic function, etc. In an illustrated mode, the applied indication 71 is a flower pattern corresponding to a plant pattern. However, it is possible to use various types of patterns such as an abstract pattern, an animal pattern, and a natural phenomenon pattern.

As long as elasticity of a part or total of a portion formed among the through holes 31 in the elastic film 30 is decreased due to the thermal deterioration in the non-stretchable region 70, joining of the first sheet layer 20A and the second sheet layer 20B in the sheet bond portion 40 is not particularly restricted. For example, joining of the first sheet layer 20A and the second sheet layer 20B in the sheet bond portion 40 may be performed using a hot-melt adhesive or using joining means based on material welding such as heat sealing, ultrasonic sealing, etc. When the joining means based on material welding is used, the through holes of the elastic film may be formed by protrusions, and the first sheet layer 20A and the second sheet layer 20B may be directly joined by welding at positions of the through holes as in Patent Literature 1. However, there is a concern that since the peeling strength is low, peeling may occur when a strong force is applied. In addition, in Patent Literature 1, since the through holes of the elastic film are formed by protrusions, the elastic film 30 is not left between the first sheet layer 20A and the second sheet layer 20B as illustrated in FIG. 24B, and there is a concern that protrusion debris (not illustrated) may be movably left around the through holes 31.

Therefore, when the joining means based on material welding is used, it is preferable to adopt a mode in which the first sheet layer 20A and the second sheet layer 20B in the sheet bond portions 40 are joined by at least the melted and solidified material 30$m$ of the elastic film 30 among the first sheet layer 20A and the second sheet layer 20B as illustrated in FIG. 24A. When the first sheet layer 20A and the second sheet layer 20B are joined using the melted and solidified material 30$m$ of the elastic film 30 as an adhesive as described above, separation strength is high, and it is possible to achieve both high air permeability and high separation strength.

In such a joining structure, for example, when welding is performed in a predetermined pattern of the sheet bond portions 40 in the stretchable region 80 and the non-stretchable region 70 in a state in which the elastic film 30 is interposed between the first sheet layer 20A and the second sheet layer 20B while being stretched in the stretching and contracting direction at a substantially uniform stretch rate in the direction orthogonal to the stretching and contracting direction as illustrated in FIG. 33 and FIG. 34, the elastic film 30 is melted at a large number of positions to form the through holes 31. At the same time, manufacture may be simply and efficiently performed using a scheme of joining the first sheet layer 20A and the second sheet layer 20B by solidification of at least a melted material of the elastic film 30 at positions of the through holes 31. In the stretchable region 80 and the non-stretchable region 70 manufactured by this scheme, the shape/area of each of the sheet bond portions 40 is substantially equal to the shape/area of each of the through holes 31 in the natural length state. Further, at the time of performing welding of the stretchable region 80 and the non-stretchable region 70 using this scheme, when the area rate of the sheet bond portions 40 in the non-stretchable region 70 is higher than that in the stretchable region 80, and heat of welding is transferred to a part or total of a portion formed among the through holes 31 in the elastic film 30, the part or total of the portion formed among the through holes 31 deteriorates due to the heat of welding to decrease elasticity. In this way, it is possible to form the non-stretchable region 70 having the above-described thermal deterioration portion 32. Therefore, it is possible to significantly simply and efficiently manufacture the stretchable structure 20X of the elastic film 30 having the stretchable region 80 and the non-stretchable region 70. In addition, the manufactured stretchable region 80 achieves both high air permeability and high separation strength.

FIG. 33 illustrates an example of a method of manufacturing the underpants-type disposable diaper. This production line corresponds to a horizontal flow mode in which the width direction of the diaper is the MD (machine direction, line flow direction), and the outer body 20 is formed thereon. After the inner body 10 manufactured on another line is attached to the outer body 20, both side portions of front and back outer bodies 20 are joined by folding at a center in the front-back direction, and division into individual diapers DP is performed. For the sake of easy understanding, the same name and reference symbol as those of a member after manufacture are used for members that are continuous in a manufacturing process.

More specifically, this production line includes an outer body assembly process 301, an inner body attachment process 302, a leg opening punching process 303, a folding process 304, and a side portion joining/separation process 305. Among these processes, the outer body assembly process 301 is a characteristic process. In more detail, in the outer body assembly process 301, as enlarged and illustrated in FIG. 34, the first sheet layer 20A and the second sheet layer 20B continuing in a belt shape at a predetermined width are fed to sealing devices 60 and 61 and such that the first sheet layer 20A and the second sheet layer 20B are bonded along a continuing direction thereof, and the elastic film 30 continuing in a belt shape at a predetermined width passes through a nip roll 90 corresponding to a slower feed speed than speeds of the sealing devices 60 and 61 and are fed to the sealing devices 60 and 61 by being interposed between the first sheet layer 20A and the second sheet layer 20B in a state of being stretched in the MD due to a speed difference. In an illustrated mode, one sheet material is segmented into two parts by a slitter 62 to feed the first sheet layer 20A as separate front and back parts. However, the sheet material may be fed as separate front and back parts, and an integrated front and back sheet material may be fed similarly to the second sheet layer 20B without separating the first sheet layer 20A into front and back parts. Similarly, in the illustrated mode, one elastic film 30 is segmented into two parts by the slitter 62 to feed the elastic film 30 as separate front and back parts. However, the elastic film 30 may be fed as separate front and back parts, and an integrated front and back elastic film 30 may be fed without separating the elastic film 30 into front and back parts.

In the sealing devices 60 and 61, the first sheet layer 20A, the elastic film 30 stretched in the MD, and the second sheet layer 20B are interposed by a seal roll 60 having a large number of pressing protrusions 60p arranged in a pattern of the sheet bond portions 40 in the stretchable region 80 and the non-stretchable region 70 described above on an outer circumference surface, and an anvil roll 61 which is disposed to face the seal roll 60 and has a smooth surface. Further, the elastic film 30 is melted only sites where it is pressed in the thickness direction between the pressing protrusions 60p and an outer circumference surface of the anvil roll 61 by heating the pressing protrusions 60p, thereby forming the through holes 31, and the first sheet layer 20A and the second sheet layer 20B are bonded by welding at positions of the through holes 31. A heat sealing device is assumed to be used as the sealing devices 60 and 61 of the illustrated mode. However, it is possible to use another device such as an ultrasonic sealing device.

Thereafter, the underpants-type disposable diaper may be formed by adopting a known manufacturing process. In the illustrated mode, the inner body 10 manufactured on another line is fed at a predetermined interval in the MD to the outer body 20 formed by the sealing devices 60 and 61 in the inner body attachment process 302, and is joined to the outer body 20 using appropriate means such as a hot-melt adhesive, heat sealing, etc. In this way, inner assembly bodies 10 and 20 are formed. Subsequently, in the leg opening punching process 303, leg openings are formed in order by the cutter device 63. Then, in the folding process 304, the inner assembly bodies 10 and 20 are folded at a center in the CD (horizontal direction orthogonal to the MD). Then, in the side portion joining/separation process 305, the outer body 20 of the front body F and the outer body 20 of the back body B are joined at portions corresponding to both side portions of each diaper DP to form the side seal portions 21, and the outer body 20 is cut at a boundary of the individual diapers to obtain the individual diapers DP.

In a case in which welding for forming the through holes 31 and the sheet bond portions 40 is performed using ultrasonic sealing (ultrasonic welding), and elasticity of the non-stretchable region 70 is decreased using heat thereof, ultrasonic vibration is easily transferred, and a sufficient thermal deterioration area of the elastic film 30 may be ensured by increasing the area of each of the sheet bond portions 40 in the non-stretchable region 70 to some extent under a condition that a speed of the production line is low (about 30 m/min). However, under a condition that the speed of the production line is high (about 120 m/min), there is a concern that welding of the sheet bond portions 40 may be insufficient when the area of each of the sheet bond portions 40 is not decreased to some extent. However, when the area of each of the sheet bond portions 40 is decreased to merely sufficiently weld the sheet bond portions 40, there is a concern that the thermal deterioration area of the elastic film 30 may be insufficient for non-stretching. On the other hand, when the area of each of the sheet bond portions 40 in the non-stretchable region 70 is set to 0.14 to 0.75 $mm^2$, and the area rate of the sheet bond portions 40 in the non-stretchable region 70 is set 8 to 17% as described above, ultrasonic welding is performed by densely disposing small sheet bond portions 40 at a narrow interval, and there is little concern about insufficient welding. Further, even though the thermal deterioration area of the elastic film 30 is small, an interval of the adjacent two through holes 31 narrows, and thus non-stretching is sufficiently obtained. The above description is similarly applied when the area of each of the sheet bond portions 40 in the non-stretchable region 70 is set 0.14 to 0.75 mm², and each of an interval 40*m* of the adjacent two sheet bond portions 40 in the non-stretchable region 70 in the stretching and contracting direction (MD) and an interval 40*c* thereof in the direction orthogonal to the stretching and contracting direction (CD) is set to 1 mm or less.

Figure 39A:
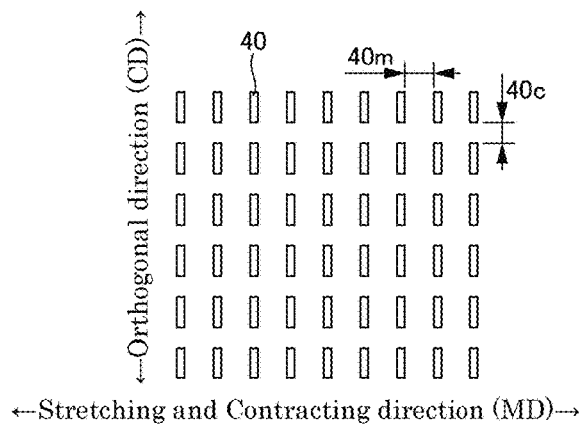
FIG. 39A, FIG. 39B, FIG. 39C are enlarged plan views of a main part illustrating a pattern of joint portions.
Figure 39B:
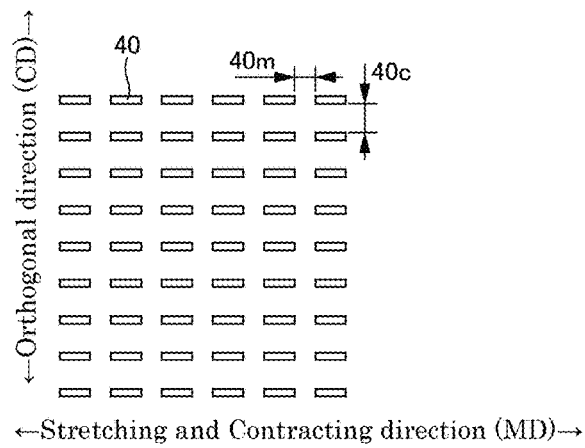
Figure 39C:
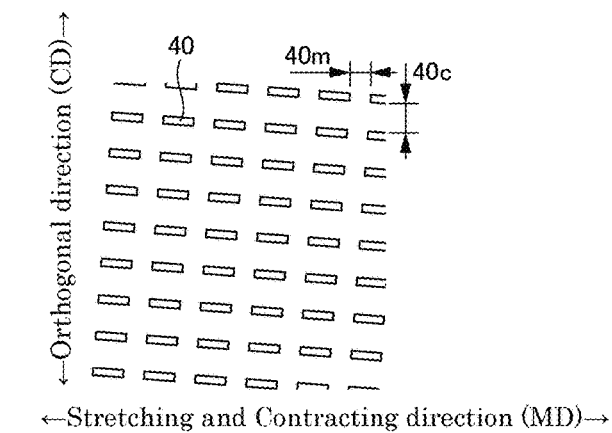
Figure 40:
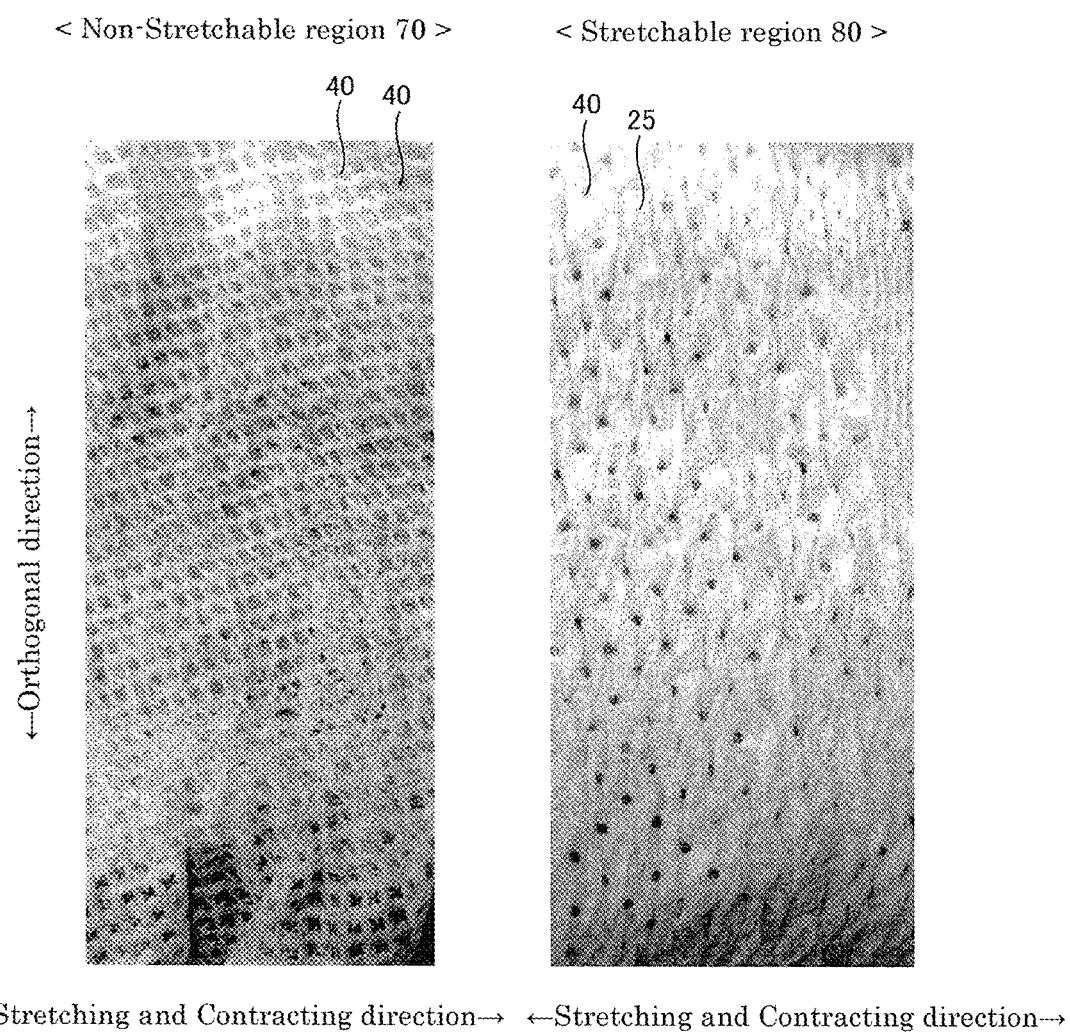
FIG. 40 is a photograph in a natural length state of a sample of an embodiment.
Figure 41:
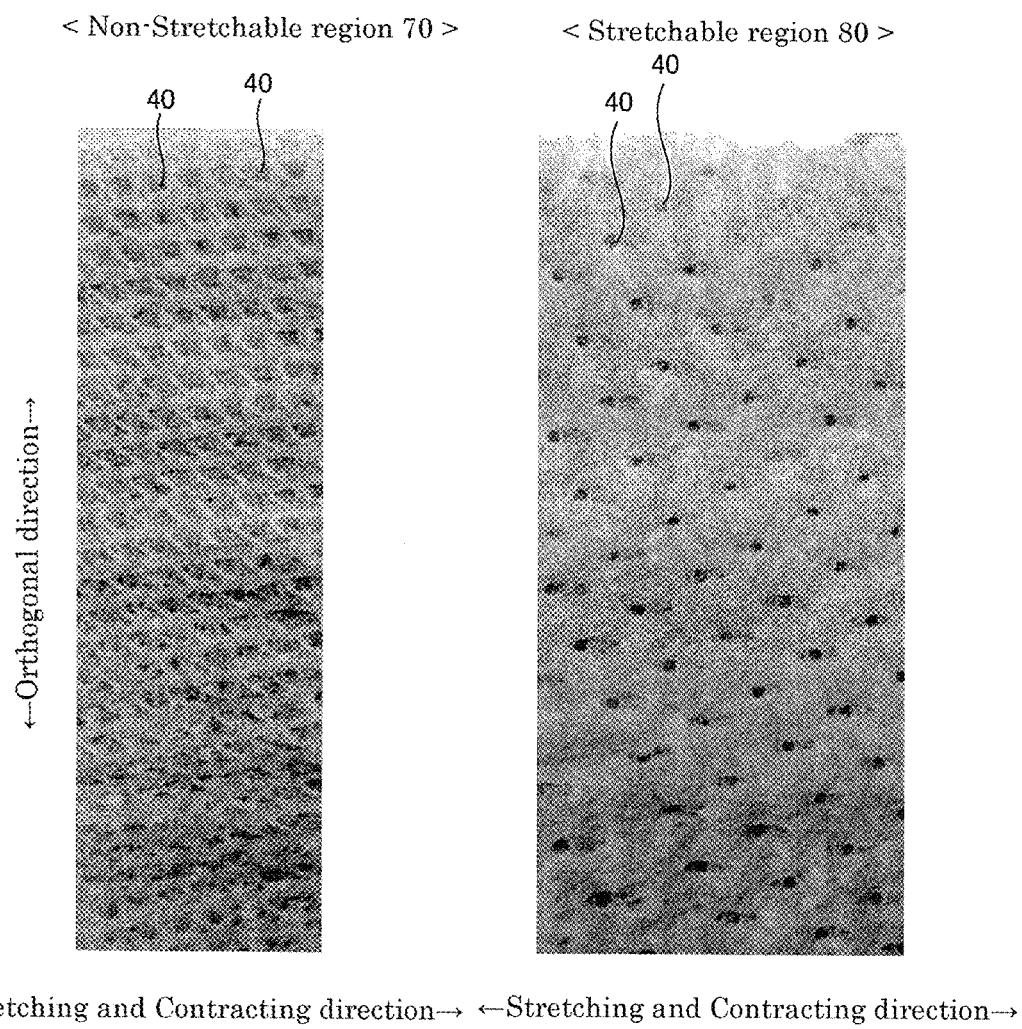
FIG. 41 is a photograph in a stretched state of the sample of the embodiment.

In addition, in a case in which welding for forming the through holes 31 and the sheet bond portions 40 is performed using ultrasonic sealing (ultrasonic welding), and elasticity of the non-stretchable region 70 is decreased using heat thereof, when the shape of the sheet bond portions 40, that is, a shape of each of the welding portions having a welding pattern in ultrasonic welding is set to a shape that is long in the MD as illustrated in FIGS. 39B and 39C, it is possible to widen the thermal deterioration area of the elastic film 30 when compared to an isotropic shape having the same area, and an area in which ultrasonic vibration is simultaneously applied does not increase when compared to a shape that is long in the CD as illustrated in FIG. 39A. Thus, there is an advantage that welding of the sheet bond portions 40 is less likely to be insufficient. For example, the shape that is long in the MD refers to an ellipse whose long axis is less than 45 degrees with respect to the MD, a polygon (including a linear shape or a rounded corner) such as a rectangle whose long side is less than 45 degrees with respect to the MD, a cloud shape whose longitudinal direction is less than 45 degrees with respect to the MD, etc.

When the sheet bond portions 40 and the through holes 31 are simultaneously formed by welding as described above, it is possible to appropriately determine a relation of a melting point of the elastic film 30, melting points of the first sheet layer 20A and the second sheet layer 20B, and a processing temperature at a welding position. However, rather than to set the melting points of the first sheet layer 20A and the second sheet layer 20B to be lower than or equal to the melting point of the elastic film 30, melt and combine the whole of the first sheet layer 20A and the second sheet layer 20B and the whole elastic film 30 at the welding positions, and form the sheet bond portions 40, it is preferable to set the melting points of the first sheet layer 20A and the second sheet layer 20B to be higher than the melting point of the elastic film 30, melt the elastic film 30 at the welding position, and not to melt a part of the first sheet layer 20A and the second sheet layer 20B or not to melt a whole of the first sheet layer 20A and the second sheet layer 20B. In other words, as understood from FIG. 31 and FIG. 32, a latter case corresponds to a structure in which fibers 20*f* of the first sheet layer 20A and the second sheet layer 20B continuing from around the sheet bond portions 40 are left, and the first sheet layer 20A and the second sheet layer 20B are joined by the melted and solidified material 30*m* of the elastic film 30, which has infiltrated and solidified among the first sheet layer 20A and the second sheet layer 20B. Further, improved adhering of the melted and solidified material of the elastic film to the first sheet layer and the second sheet layer is obtained, and strength of the first sheet layer 20A and the second sheet layer 20B rarely decreases. Thus, peeling strength is further enhanced. This situation in which "a part of the first sheet layer 20A and the second sheet layer 20B is not melted" includes a mode in which for all fibers of the sheet bond portions 40, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

From this point of view, the melting point of the elastic film 30 is preferably about 80 to 145° C., melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 80° C.

An example illustrated in FIG. 2, FIG. 35, etc. is an example in which the elastic film stretchable structure 20X is applied to a stretchable structure other than the waist end portion region 23 of the outer body 20. However, appropriate changes are allowed. For example, the waist end portion region 23 may be included at the time of application as in the example illustrated in FIG. 1 and FIG. 2 and the example illustrated in FIG. 33, or it is possible to adopt a mode in which the elastic film stretchable structure 20X is not provided in the intermediate region L between the torso region T of the front body F and the torso region T of the back body B. In addition, the above-described stretchable structure 20X may be applied to another elastic portion such as a three-dimensional gather, a plane gather, etc. generally used for a waist portion, a fastening tape, and an absorbent article of a tape-type disposable diaper in addition to the underpants-type disposable diaper. In addition, even though the non-stretchable region 70 is included in the present embodiment, it is possible to adopt a mode in which the whole stretchable structure 20X of the elastic film 30 is used as the stretchable region 80 and the non-stretchable region 70 is not included. Furthermore, even though the stretching and contracting direction is regarded as the width direction in the illustrated example, the stretching and contracting direction may be set to front-back direction or set to both the width direction and the front-back direction.

<Formation Test of Non-Stretchable Region>

A spunbond nonwoven fabric having a basis weight of 17 g/m², which uses a PE/PP conjugate fiber having a fineness of 1.7 to 1.9 dtex (core: polypropylene (melting point 165° C.), sheath: polyethylene (melting point 130° C.)) as a raw material, was used as the first sheet layer 20A and the second sheet layer 20B, and a product name MD3 (basis weight 35 g/m², thickness: 0.04 mm, melting point: 90 to 100° C.) manufactured by Exten Corporation was used as the elastic film 30. In a state in which the MD of the nonwoven fabric is set to the stretching and contracting direction, and the elastic film is stretched 3.5 times in the MD, the through holes 31 and the rectangular sheet bond portions 40 having a length 40*m* in the MD of 1 mm, a length 40*c* in the CD of 0.5 mm, and an area of 0.5 mm² were formed in the pattern illustrated in FIG. 39B and at various intervals shown in Table 1 using ultrasonic sealing. Then, an elongation at an elastic limit was measured. Ultrasonic sealing was set based on a condition that a PE layer of fibers of the elastic film, the first sheet layer, and the second sheet layer melts. As a result, as shown in Table 1, it was found that when an interval of the adjacent two sheet bond portions in the MD is 1 mm or less, and an interval thereof in the CD is 1 mm or less, elasticity is eliminated due to thermal deterioration of a most part between the through holes, and non-stretching is obtained.

TABLE 1

| | | \multicolumn{7}{c}{Interval in MD} | | | | | | |
|---|---|---|---|---|---|---|---|---|
| | | 0.25 | 0.5 | 0.75 | 1 | 1.25 | 1.5 | 2 |
| Interval in CD | 0.25 | 100% (59%) | 100% (44%) | 100% (38%) | — | — | — | — |
| | 0.5 | 100% (40%) | 100% (33%) | 100% (29%) | 123% (28%) | — | — | — |
| | 0.75 | 100% (32%) | 100% (27%) | 112% (23%) | 141% (20%) | 158% (18%) | — | — |
| | 1 | — | 115% (22%) | 128% (19%) | 150% (17%) | 160% (15%) | 184% (13%) | — |
| | 1.25 | — | — | 144% (16%) | 157% (14%) | 174% (13%) | 213% (11%) | 246% (9.5%) |
| | 1.5 | — | — | — | 170% (13%) | 207% (11%) | 244% (10%) | 251% (8.3%) |
| | 2 | — | — | — | — | 219% (8.9%) | 245% (8.0%) | 255% (6.7%) |

※In the table, a value in brackets corresponds to an area rate of each of the joint portions.

<Fourth Mode>

Next, a fourth mode will be described with reference to FIG. 3 to FIG. 7, FIG. 16, FIG. 37, FIG. 38, and FIG. 42 to FIG. 52. In the outer body 20, as illustrated in FIG. 4 to FIG. 6, the elastic film 30 is arranged between the first sheet layer 20A and the second sheet layer 20B, and elasticity in the width direction is imparted. The planar shape of the outer body 20 corresponds to a pseudo-hourglass shape as a whole due to the concave leg line 29 formed to form leg openings at intermediate both side portions, respectively. The outer body 20 may be divided into two front and back parts, and the both parts may be separated from each other in the front-back direction in the crotch portion.

Figure 43:
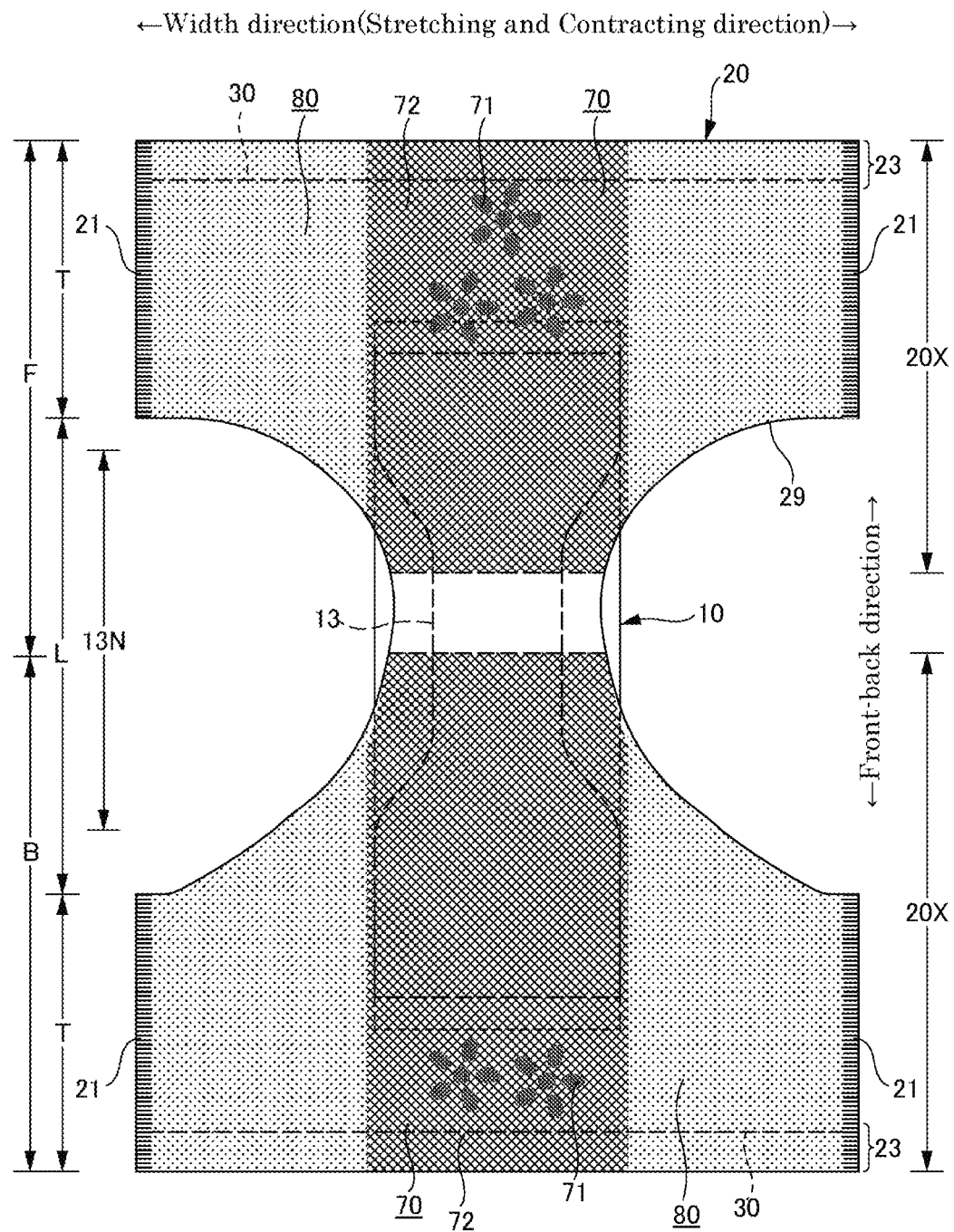
FIG. 43 is a plan view (external surface side) of the underpants-type disposable diaper in the completely spread state.

Characteristically, as illustrated in FIG. 43, the stretchable structure 20X of the invention is formed in the torso region T of the front body F, the torso region T of the back body B, and the intermediate region L therebetween in the outer body 20. In other words, the elastic film 30 is stacked between the first sheet layer 20A and the second sheet layer 20B in the stretchable structure 20X of the outer body 20, and a region having this elastic film stretchable structure 20X includes the non-stretchable region 70 and the stretchable region 80 stretchable in the width direction provided at least at one side of the non-stretchable region 70 in the stretching and contracting direction (width direction). The stretchable region 80 has an elongation at an elastic limit in the width direction of 200% or more (preferably 265 to 295%) when the first sheet layer 20A and the second sheet layer 20B are directly or indirectly joined at the large number of sheet bond portions 40 arranged at intervals in the width direction and the vertical direction orthogonal thereto (the stretching and contracting direction and the direction orthogonal thereto) in a state in which the elastic film 30 is stretched in the width direction along surfaces thereof. Meanwhile, the non-stretchable region 70 has an elongation at an elastic limit in the width direction of 130% or less (preferably 120% or less, more preferably 100%) when the first sheet layer 20A and the second sheet layer 20B are directly or indirectly joined at the large number of sheet bond portions 40 arranged at intervals in the width direction and the vertical direction orthogonal thereto, and the area rate of the sheet bond portions 40 is higher than that in the stretchable region 80 in a state in which the elastic film 30 is stretched in the width direction along surfaces thereof.

When the first sheet layer 20A and the second sheet layer 20B are directly or indirectly joined at the large number of sheet bond portions 40 arranged at intervals in the stretching and contracting direction and the direction orthogonal thereto in a state in which the elastic film 30 is stretched in the width direction in such an elastic film stretchable structure 20X, basically, as the area rate of the sheet bond portions 40 increases, a portion in which the first sheet layer 20A and the second sheet layer 20B contract by the elastic film 30 decreases. Thus, an elongation at an elastic limit tends to decrease. Therefore, the non-stretchable region 70 and the stretchable region 80 may be formed only by changing the area rate of the sheet bond portions 40 using such a characteristic.

In this case, in the stretchable region 80, as illustrated in FIG. 7D, in the natural length state of the elastic film 30, the first sheet layer 20A and the second sheet layer 20B between each pair of adjacent sheet bond portions rise in a direction away from each other, and thus a contraction wrinkle 25 extending in a direction intersecting the stretching and contracting direction is formed. As illustrated in FIG. 7C, in a worn state of being stretching to some extent in the width direction, the contraction wrinkle 25 is left even though the contraction wrinkle 25 is stretched. In addition, as in the illustrated modes, when the first sheet layer 20A is not and the second sheet layer 20B is not joined to the elastic film 30 in a portion other than at least between the first sheet layer 20A and the second sheet layer 20B, as understood from FIG. 7C assuming the worn state and FIGS. 7A and 7B assuming a completely spread state of the first sheet layer 20A and the second sheet layer 20B, in these states, a gap is formed between each sheet bond portion 40 and each through hole 31 for the sheet bond portion in the elastic film 30, thus, air permeability is imparted due to the gap even when a material of the elastic film 30 corresponds to a non-porous film or a sheet.

In a case in which the non-stretchable region 70 is formed when the area rate of the sheet bond portions 40 in the non-stretchable region 70 is higher than that in the stretchable region 80, a raised portion or an extremely fine wrinkle is formed between sheet bond portions 40 in the non-stretchable region 70. However, since the area rate of the sheet bond portions 40 is significantly high, elasticity is substantially eliminated. In addition, the non-stretchable region 70 may be formed by heating and melting the elastic film 30. In this case, when the sheet bond portions 40 are formed in the non-stretchable region 70, the area rate of the sheet bond portions 40 may be higher or lower than that in the non-stretchable region 70. For example, it is possible to provide only the sheet bond portions 40 arranged in a display shape to form a display portion 71 described below. Further, the non-stretchable region 70 may be formed by finely dividing the elastic film 30 at least in the stretching and contracting direction. Such division may be performed by forming the sheet bond portions 40 in a net shape or a stripe shape intersecting the stretching and contracting direction, or cutting the elastic film 30 in a net shape or a stripe shape intersecting the stretching and contracting direction using pressing, etc.

Figure 45A:
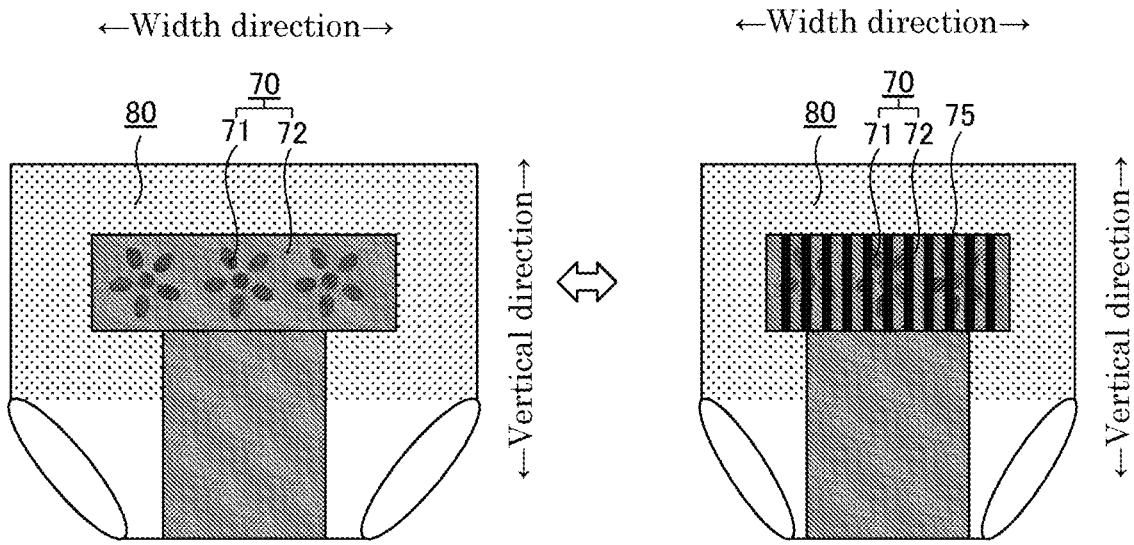
FIG. 45A and FIG. 45B are schematic front views for description of an operation.
Figure 45B:
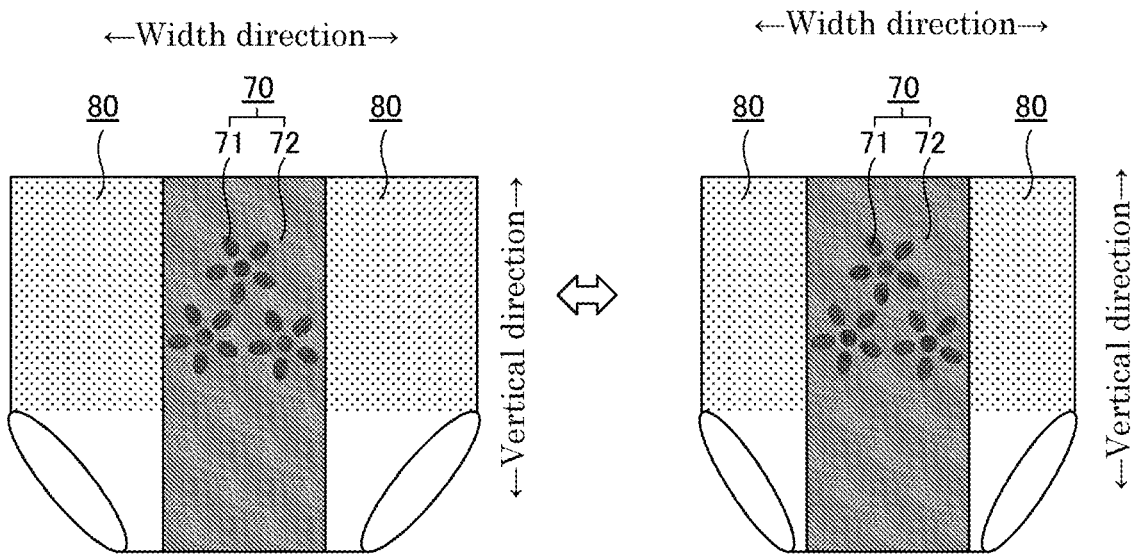

Further, in the region having the elastic film stretchable structure 20X, when a configuration in which the stretchable region 80 is not present at both sides of the non-stretchable region 70 in the vertical direction (the direction orthogonal to the stretching and contracting direction) is adopted, and the display portion 71 comprised of the sheet bond portions 40 is disposed in the middle in the vertical direction, as schematically illustrated in FIG. 45B, the display portion 71 is hardly affected by contraction of the stretchable region 80, and degradation of appearance of the display portion 71 is prevented. On the other hand, as schematically illustrated in FIG. 45A, when the stretchable region 80 is adjacent to the display portion 71 of the non-stretchable region 70 in the direction orthogonal to the stretching and contracting direction, a wrinkle or pleat 75 is formed in the non-stretchable region 70 due to an influence of contraction of the stretchable region 80, and appearance of display is degraded. In the non-stretchable region 70, the display portion 71 may be provided in a part thereof, and the other part may be set to a non-display portion 72 as in the illustrated mode. Alternatively, the display portion 71 may be provided across the whole non-stretchable region 70.

The shapes of each of the sheet bond portions 40 and each of the through portions 31 in the natural length state may be determined such as a perfect circle, an ellipse, a polygon such as a triangle, a rectangle, a rhombus, etc., a star shape, a cloud shape, etc. A size of each of the sheet bond portions 40 may be appropriately determined. However, when the size is excessively large, an influence of hardness of the sheet bond portions 40 on a sense of touch increases. When the size is excessively small, a joining area is small, and materials may not be sufficiently attached to each other. Thus, in general, an area of each of the sheet bond portions 40 is preferably set to about 0.14 to 3.5 mm$^2$. An area of an opening of each of the through portions 31 may be greater than or equal to that of each of the sheet bond portions since the sheet bond portions are formed via the through portions 31. However, the area is preferably set to about 1 to 1.5 times the area of each of the sheet bond portions. The area of the opening of each of the through portions 31 refers to a value in a state in which the stretchable structure corresponds to a natural length, and refers to a minimum value in a case in which the area of the opening of each of the through portions 31 is not uniform in the thickness direction such as a case in which the area is different between a front side and a back side of the elastic film.

In general, in the case in which the non-stretchable region 70 is formed when the area rate of the sheet bond portions 40 is higher than that in the stretchable region 80, the area of each of the sheet bond portions and the area rate of the sheet bond portions 40 in each region are preferably set to as below.

(Non-Stretchable Region 70)

Area of each of sheet bond portions 40: 0.14 to 3.5 mm$^2$ (particularly 0.25 to 1.0 mm$^2$)

Area rate of sheet bond portions 40: 16 to 45% (particularly 25 to 45%)

(Stretchable Region 80)

Area of each of sheet bond portions 40: 0.14 to 3.5 mm$^2$ (particularly 0.14 to 1.0 mm$^2$)

Area rate of sheet bond portions 40: 1.8 to 19.1% (particularly 1.8 to 10.6%)

When the area rate of the sheet bond portions 40 is made different between the non-stretchable region 70 and the stretchable region 80, the number of sheet bond portions 40 per unit area may be changed as illustrated in FIG. 37A, or the area of each of the sheet bond portions 40 may be changed as illustrated in FIG. 37B. In a former case, the area of each of the sheet bond portions 40 may be the same or different between the non-stretchable region 70 and the stretchable region 80. In a latter case, the number of sheet bond portions 40 per unit area may be the same or different between the non-stretchable region 70 and the stretchable region 80.

A planar array of the sheet bond portions 40 other than the display portion 71 may be appropriately determined. However, in order to highlight the display portion 71, it is preferable to adopt a planar array in which the sheet bond portions 40 are regularly repeated. In addition to the planar array in which the sheet bond portions 40 are regularly repeated such as an oblique lattice shape or a hexagonal lattice shape (these shapes are also referred to as a staggered shape), a square lattice shape, a rectangular lattice shape, a parallel body lattice shape (a mode in which two groups are provided such that a large number of parallel oblique row groups intersect each other as illustrated in the figure), etc., it is possible to adopt a planar array in which a group of the sheet bond portions 40 (arrangement of a group unit may be regular or irregular, and a pattern, a letter shape, etc. may be used) is regularly repeated. An arrangement mode of the sheet bond portions 40 other than the display portion 71 may be the same or different between the stretchable region 80 and the non-stretchable region 70.

The display portion 71 may be formed by arranging dot-shaped sheet bond portions 40 in a shape of the display portion 71 as illustrated in FIG. 43, FIG. 47, and FIG. 48, and may be formed by forming a single sheet bond portion 40 in the shape of the display portion 71. The shape of the display portion 71 may correspond to an indication known in a field of the absorbent article, for example, a pattern for decoration (including a tiny picture or a character), a function indicator such as a usage method, usage assistance, a size, etc., or a mark indication such as a manufacturer, a product name, a characteristic function, etc. In a mode illustrated in FIG. 43, a flower pattern corresponding to a type of plant pattern is applied. However, another plant pattern may be applied, and it is possible to use various types of patterns such as an abstract pattern, an animal pattern, and a natural phenomenon pattern.

A scheme of forming the sheet bond portions 40 is not particularly restricted. However, when the sheet bond portions 40 are formed by welding, appearance of the sheet bond portions 40 is different from surroundings. Thus, the display portion 71 is highlighted, which is preferable.

Figure 44A:
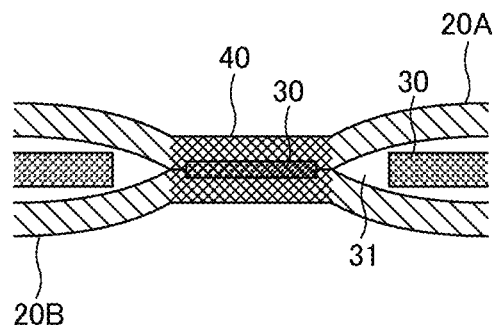
FIG. 44A, FIG. 44B and FIG. 44C are cross-sectional views, each schematically illustrating a cross section of a main part of an outer body stretched to some extent in the width direction.
Figure 44B:
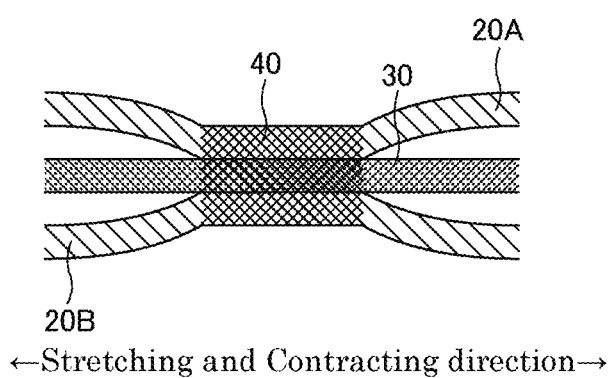
Figure 44C:
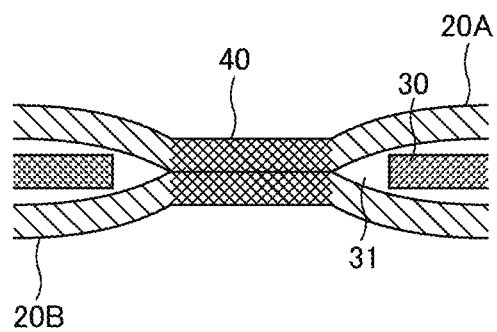

In the sheet bond portion 40, the first sheet layer 20A and the second sheet layer 20B may be joined directly or indirectly through another sheet such as the elastic film 30. FIG. 44 illustrates three types of representative joining structures. In the joining structures illustrated in FIGS. 44A and 44C, similarly to the mode illustrated in FIG. 3, the first sheet layer 20A and the second sheet layer 20B are joined via through portions 31 formed in the elastic film 30, and the first sheet layer 20A is not and the second sheet layer 20B is not joined to the elastic film 30 in a portion other than at least between the first sheet layer 20A and the second sheet layer 20B in the sheet bond portions 40 (area with diagonal lattice pattern in FIG. 44). This joining structure may be manufactured only by using an arrangement pattern of bumps of a patterned calendar roller in a method of JP 2004-532758 A as the pattern of the sheet bond portions 40. However, it is considered that the method described in JP 2004-532758 A pushes out the elastic film 30 without melting the elastic film 30. In this case, as illustrated in FIG. 44(c), the elastic film 30 is not left between the first sheet layer 20A and the second sheet layer 20B, and there is a concern that protrusion debris (not illustrated) may be movably left around the through portions 31.

On the other hand, when the sheet bond portions 40 are formed in the arrangement pattern of the sheet bond portions 40 using a sheet bond portion forming device 100 (an ultrasonic sealing device 101 illustrated in FIG. 46A or a heat sealing device 102 illustrated in FIG. 46B) in a state in which the elastic film 30 is interposed between the first sheet layer 20A and the second sheet layer 20B as illustrated in FIG. 46, it is possible to the first sheet layer 20A and the second sheet layer 20B may be joined via the through portions 31 simultaneously with forming the through portions 31 in the elastic film 30, and to efficiently perform manufacture. In this case, it is possible to obtain a joining structure in which a melting separation piece of the elastic film 30 is left in the sheet bond portions 40 as illustrated in FIG. 44A. As described above, in a mode in which the melting separation piece of the elastic film 30 is left between the first sheet layer 20A and the second sheet layer 20B of the sheet bond portions 40, the first sheet layer 20A and the second sheet layer 20B may be joined to the elastic film 30 in the sheet bond portions 40. However, the mode correspond to a mode in which the first sheet layer 20A is not and the second sheet layer 20B is not joined to the elastic film 30 in a portion other than at least between the first sheet layer 20A and the second sheet layer 20B in the sheet bond portions 40 (which means that a case in which the first sheet layer 20A is not and the second sheet layer 20B is not, in the sheet bond portion 40, joined to the surrounding elastic film 30 (that is, an edge portion of the through portions 31) is excluded). In this case, the area of each of the sheet bond portions is substantially equal to the area of each of the through portions. In addition, when a type of material of the elastic film 30 or a processing condition such as a processing temperature is appropriately selected such that the elastic film 30 is not melted and separated and the through portions 31 are not formed in the sheet bond portions 40 in a manufacturing method described in JP 2004-532758 A, it is possible to obtain a joining structure in which the through portions are not formed in the elastic film 30 and the first sheet layer 20A and the second sheet layer 20B are indirectly joined through the elastic film 30 in the sheet bond portions 40 as illustrated in FIG. 44B.

Figure 47A:
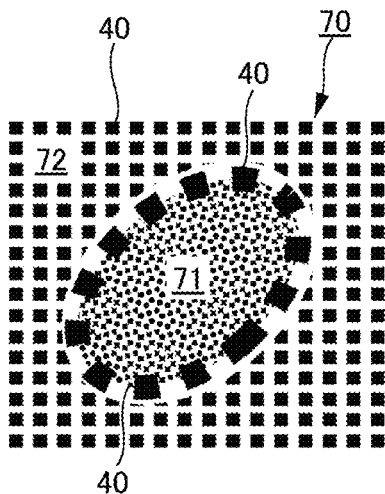
FIG. 47A, FIG. 47B, FIG. 47C and FIG. 47D are plan views, each illustrating a pattern example of sheet bond portions around a display portion.
Figure 47B:
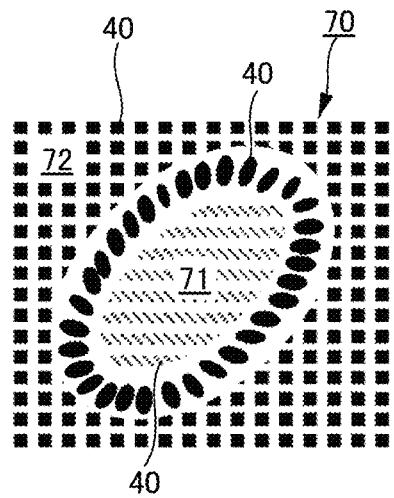
Figure 47C:
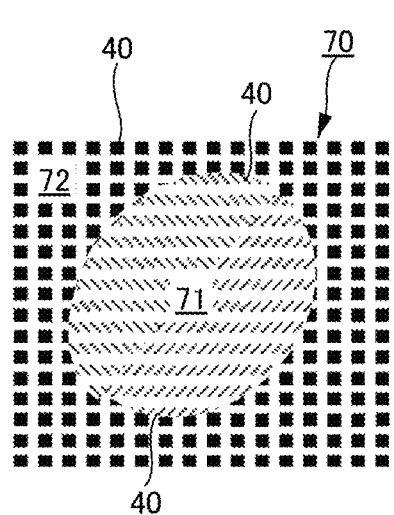
Figure 47D:
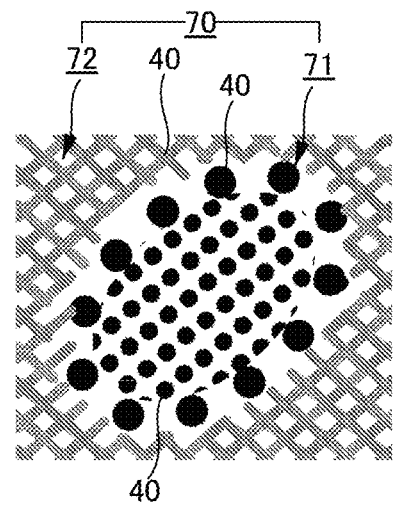
Figure 48A:
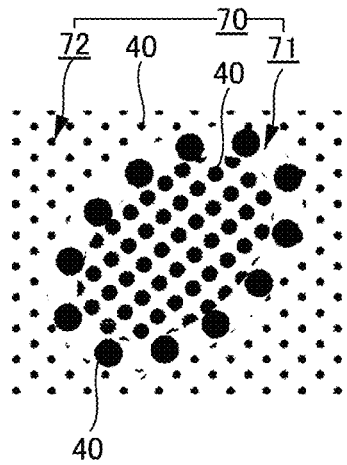
FIG. 48A, FIG. 48B, FIG. 48C, FIG. 48D, and FIG. 48E are plan views, each illustrating a pattern example of the sheet bond portions around the display portion.
Figure 48B:
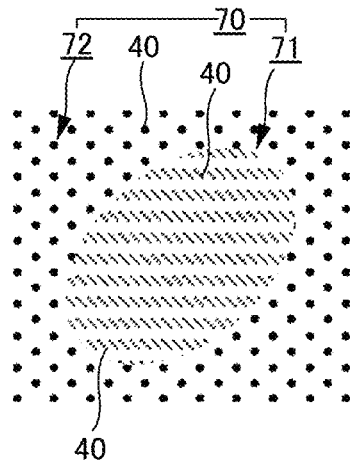
Figure 48C:
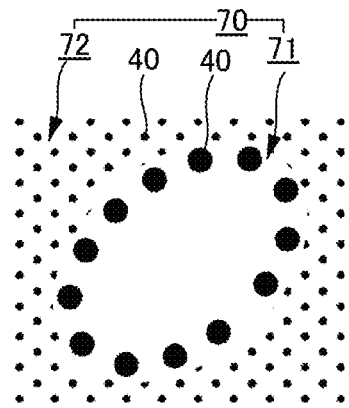
Figure 48D:
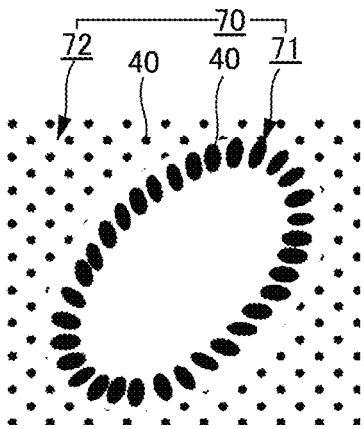
Figure 48E:
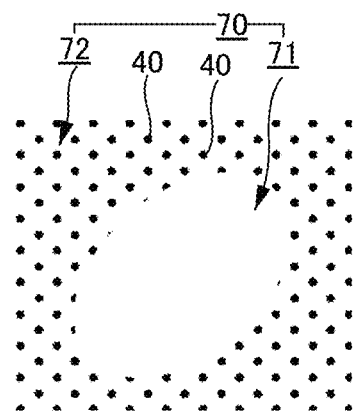

The display portion 71 in the non-stretchable region 70 is formed by the sheet bond portions 40. Thus, when the non-stretchable region 70 is formed by making the area rate of the sheet bond portions 40 to be higher than that in the stretchable region 80, and the non-display portion 72 is provided, a shape, a size, and an angle of each of the sheet bond portions, and an area rate of the sheet bond portions 40 need to be different between the non-display portion 72 and the display portion 71 as illustrated in FIGS. 47A to 47C. However, in this case, there is a merit that it is sufficient to perform only one process in a pattern of the sheet bond portions 40 in all the stretchable region 80, the display portion 71 of the non-stretchable region 70, and the non-display portion 72 of the non-stretchable region 70 using the sheet bond portion forming device 100 (an ultrasonic sealing device illustrated in FIG. 48A or a heat sealing device 102 illustrated in FIG. 48B) as illustrated in FIGS. 48A and 48B. In this mode, when the pattern of the sheet bond portions 40 in the non-display portion 72 is set to a net shape illustrated in FIG. 49A (or a stripe shape intersecting in the stretching and contracting direction), the elastic film 30 in the non-display portion 72 may be separated to obtain non-stretching as illustrated in FIG. 47D. However, the sheet bond portions 40 are formed in the same pattern.

Figure 46A:
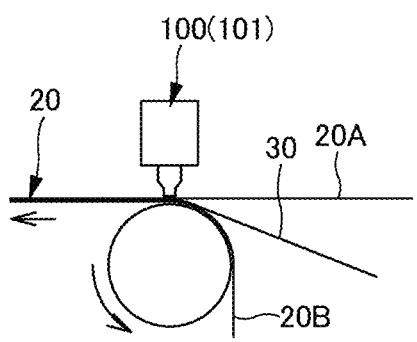
FIG. 46A, FIG. 46B, FIG. 46C and FIG. 46D are schematic views illustrating a method of forming sheet bond portions.
Figure 46B:
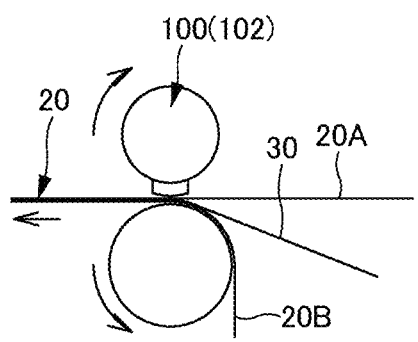
Figure 46C:
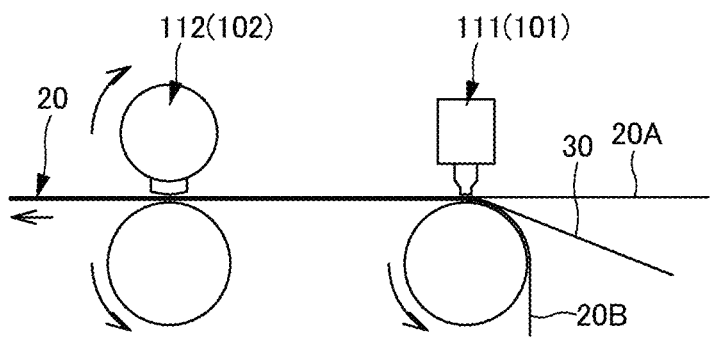
Figure 46D:
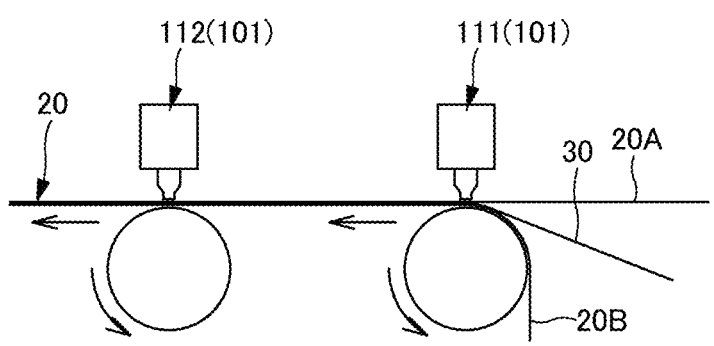

When the non-stretchable region 70 is formed by heating and melting the elastic film 30, after a melting temperature of the first sheet layer 20A and the second sheet layer 20B is set to be sufficiently higher than a melting temperature of the elastic film 30, at least the sheet bond portions 40 of the display portion 71 are formed by a sheet bond portion forming device 111 (the heat sealing device 102 illustrated in FIG. 46B may be used) as illustrated in FIGS. 46C and 46D. Thereafter, the whole non-stretchable region 70 or the non-display portion 72 is heated by an elastic film melting device 112 (the heat sealing device illustrated in FIG. 46A or the ultrasonic sealing device illustrated in FIG. 46B) to a temperature at which the first sheet layer 20A and the second sheet layer 20B are not melted and welded and the elastic film 30 is melted. In this way, it is possible to melt only the elastic film 30. When the elastic film 30 is melted across the whole non-stretchable region 70, the area rate of the sheet bond portions 40 in which the display portion 71 is formed may not be higher than that in the stretchable region 80. Therefore, the display portion 71 may be formed without restriction as illustrated in FIGS. 48A to 48E. More specifically, in examples illustrated in FIGS. 48A to 48E, the area rate of the sheet bond portions 40 in the non-display portion 72 is lowered. In the example illustrated in FIG. 48A, the area rate of the sheet bond portions 40 in the display portion 71 is high. In the example illustrated in FIG. 48B, the area rate of the sheet bond portions 40 in the display portion 71 is low. In addition, in the examples illustrated in FIGS. 48C and 48D, the sheet bond portions 40 in the display portion 71 are formed only in a site along an outer circumference of the display portion 71, and the sheet bond portions 40 are not formed on the inside. Further, in the example illustrated in FIG. 48E, the sheet bond portions 40 are regularly provided in the non-display portion 72, and the sheet bond portions 40 in the display portion 71 are excluded. In this way, the display portion 71 appears. Meanwhile, when the elastic film 30 is melted only in the non-display portion 72, non-stretching needs to be obtained by setting the area rate of the sheet bond portions 40 forming the display portion 71 to be higher than that in the stretchable region 80.

Figure 49A:
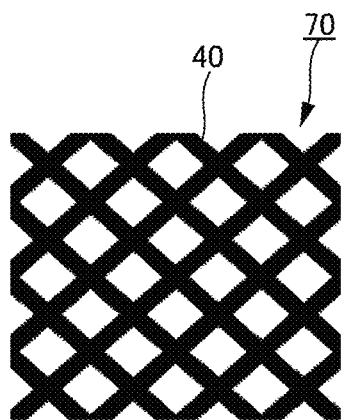
FIG. 49A and FIG. 49B are plan views, each illustrating a pattern example of the sheet bond portions.
Figure 49B:
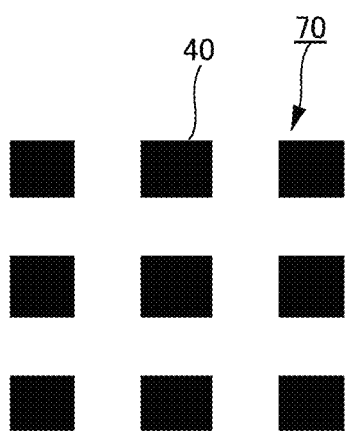

The elastic film 30 may be divided to obtain non-stretching by forming the sheet bond portions 40 in the whole non-stretchable region 70 or the non-display portion 72 in a pattern of the sheet bond portions 40 corresponding to the net shape illustrated in FIG. 49A (or a stripe shape intersecting in the stretching and contracting direction) using the sheet bond portion forming device 111 instead of the elastic film melting device 112. Alternatively, non-stretching may be obtained by forming the dot-shaped sheet bond portions 40 at a high area rate in the whole non-stretchable region 70 or the non-display portion 72 as illustrated in FIG. 49B. However, when this process is performed in the whole non-stretchable region 70, a pattern in which the display portion 71 is not crushed needs to be adopted.

Figure 42:
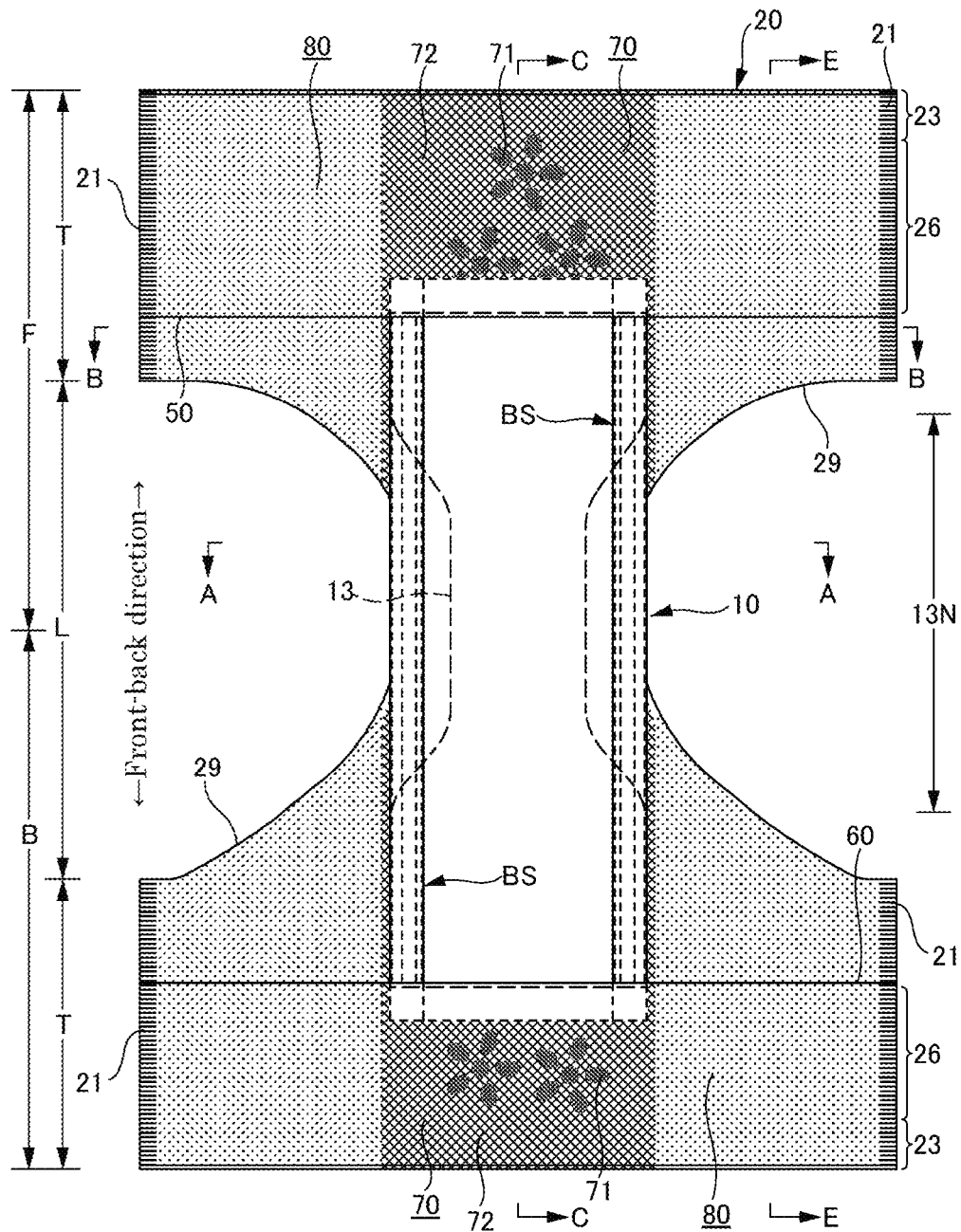
FIG. 42 is a plan view (internal surface side) of the underpants-type disposable diaper in the completely spread state.

The modes illustrated in FIG. 42 and FIG. 43 correspond to a mode in which the elastic film stretchable structure 20X extends to the waist end portion region 23, and a stretchable structure 20X in another width direction is not included in a front and a back of the non-stretchable region 70. However, when the elastic film stretchable structure 20X is used in the waist end portion region 23, tightening of the waist end portion region 23 is insufficient. It is possible to provide a stretchable structure 20X according to a conventional elongated waist end portion elastic member 24 as necessary without providing the elastic film stretchable structure 20X in the waist end portion region 23 as illustrated in FIG. 38 (a longitudinal section view corresponding thereto is FIG. 16). The waist end portion elastic members 24 correspond to elongated elastic members such as a plurality of rubber threads disposed at intervals in the vertical direction, and apply a stretching force to tighten around the waist of the body. The waist end portion elastic members 24 are not disposed substantially in a bundle with a close spacing, and three or more, preferably five or more members are disposed at intervals of about 3 to 8 mm to form a predetermined stretchable zone. A stretch rate of the waist end portion elastic member 24 in fixing may be appropriately determined. However, the stretch rate may be set to about 230 to 320% in the case of normal adult use. Rubber threads are used as the waist end portion elastic member 24 in an illustrated example. However, for example, another elongated elastic member such as flat rubber may be used.

Figure 50:
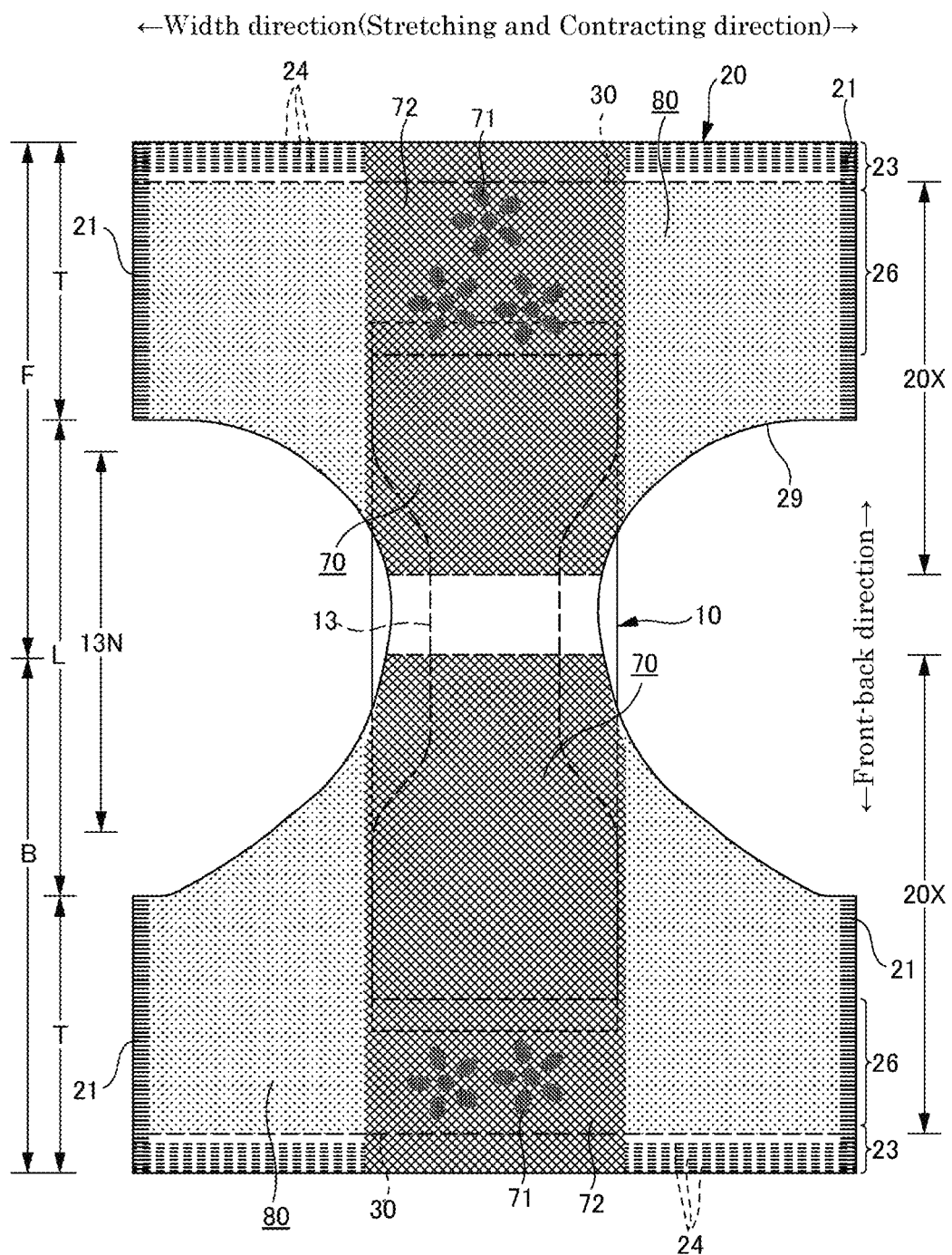
FIG. 50 is a plan view (external surface side) of the underpants-type disposable diaper in the completely spread state.

In this case, as illustrated in FIG. 38, it is possible to form the stretchable region 80 in which the elongated waist end portion elastic member 24 is fixed in a stretched state along the width direction across a whole range in the width direction corresponding to a range between both the side seal portions 21. However, when the display portion 71 is provided near the waist end portion region 23, even though the display portion 71 is located in the middle in the direction orthogonal to the stretching and contracting direction of the non-stretchable region 70, the display portion 71 is likely to be affected by stretching and contraction of the waist end portion region 23. Therefore, in a preferable mode, as illustrated in FIG. 50, in a case that the waist end portion elastic member 24 is provided, the non-stretchable region 70 or a weak stretchable region 80 is formed by not providing the waist end portion elastic member 24, cutting finely, cutting in the middle in the width direction, or reducing the number, in a region having the elastic film stretchable structure 20X of the waist end portion region 23 in a width direction range corresponding to a width direction range of the display portion 71, more preferably corresponding to a width direction range of the non-stretchable region 70.

As another mode, it is possible to adopt a mode in which the stretchable structure 20X is not provided in the intermediate region L between the torso region T of the front body F and the torso region T of the back body B.

Arrangement of the stretchable region 80 and the non-stretchable region 70 may be appropriately determined. In the case of the outer body 20 of the underpants-type disposable diaper as in the present embodiment, since a portion overlapping the absorber 13 is a region not requiring stretching/contracting, it is preferable to form the non-stretchable region 70 including the display portion 71 including a part or total of the portion overlapping the absorber 13 (desirably including substantially the whole inner body fixed part 10B) as in the illustrated mode. A region overlapping the absorber 13 in the outer body 20 is a region having elasticity and a portion fixed to the absorber 13, and thus is a region in which an influence of contraction of the stretchable region 80 is relatively small and is suitable for providing the display portion 71. On the other hand, a region not overlapping the absorber 13 does not require elasticity and flexibility, and thus is a region naturally not having a display such as a pattern. To this extent, the region is a region which is significant for providing a display that improves appearance. According to the invention, it is possible to provide the non-stretchable region 70 in such a region to provide the display portion 71 therein. The non-stretchable region 70 may be provided in both the region overlapping the absorber 13 and the region not overlapping the absorber 13, or the non-stretchable region 70 may be provided in any one of the regions.

Figure 51A:
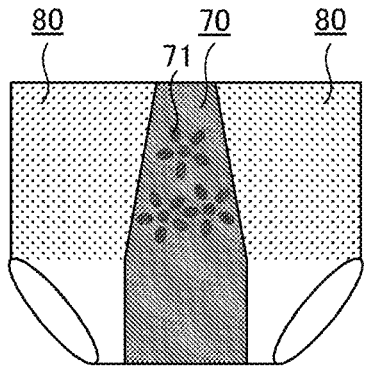
FIG. 51A, FIG. 51B, FIG. 51C, FIG. 51D and FIG. 51E are front views schematically illustrating various modes of the underpants-type disposable diaper.
Figure 51B:
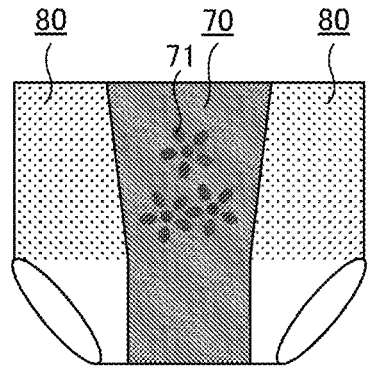
Figure 51C:
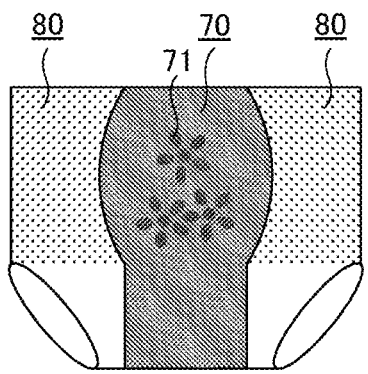

From the above viewpoint, a torso intermediate region 26 defined by a vertical direction range between the waist end portion region 23 and the absorber 13 as in the illustrated mode is a region suitable to provide the non-stretchable region 70. In this case, it is possible to form the non-stretchable region 70 having the display portion 71 in the middle of the torso intermediate region 26 in the width direction, and to set width direction ranges corresponding to ranges between the non-stretchable region 70 and both the side seal portions 21 to the stretchable regions 80. Since the middle of the torso intermediate region 26 in the width direction is a portion at which, when the non-stretchable region 70 is formed in this portion, and both sides thereof is used as the stretchable regions 80, a fitting property with respect to the abdominal bulge of the wearer is excellent. In addition, when the non-stretchable region 70 is continued to the waist end portion region 23, it is possible to compensate for the fitting property by the stretchable regions 80 on both sides thereof Further, it is possible to improve a fitting property with respect to a surface of the body using a shape of the non-stretchable region 70. For example, in a case in which the non-stretchable region 70 is provided at the central part in the width direction in the outer body 20 of the underpants-type disposable diaper, when the shape of the non-stretchable region 70 is set to a shape in which a width narrows continuously or stepwise from the crotch side toward the waist opening side as illustrated in FIG. 51A, a fitting property corresponding to a case in which the waist is thin is excellent. In addition, when the shape of the non-stretchable region 70 is set to a shape in which the width narrows continuously or stepwise from the crotch side toward the waist opening side as illustrated in FIG. 51B, a fitting property is excellent when the abdominal bulge of the wearer is particularly large in the case of the front body F and when a bulge of the gluteal region is particularly large in the case of the back body B. Further, when the shape of the non-stretchable region 70 is set to a shape in which the width widens and then narrows continuously or stepwise from the crotch side toward the waist opening side as illustrated in FIG. 51C, a fitting property is excellent in a case in which the wearer has a standard body type.

Figure 51D:
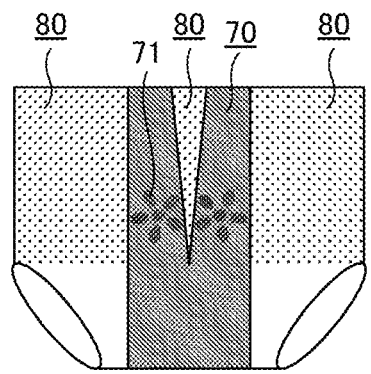

In addition, when a continuous width of the non-stretchable region 70 is widened, a fitting property and flexibility are degraded. Thus, when the shape of the non-stretchable region 70 is set to a shape branched into a plurality of parts from the crotch side toward the waist opening side, and the stretchable region 80 is provided between both parts of the branched non-stretchable region 70 as illustrated in FIG. 51D, it is possible to provide the display portion 71 based on the non-stretchable region 70 while preventing the outer body 20 from hardening, which is preferable.

Figure 51E:
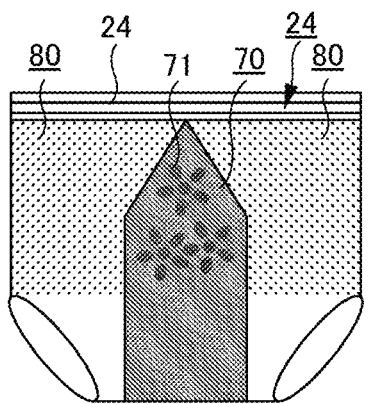

In addition, in a case in which the waist end portion elastic member 24 is provided in a width direction range corresponding to the display portion of the non-stretchable region 70 in the waist end portion region 23, when a shape in which the width narrows continuously or stepwise from the crotch side toward the waist opening side as illustrated in FIG. 51E is adopted, there is a merit that an influence of stretching and contraction of the waist end portion region 23 thereon is little.

Figure 52A:
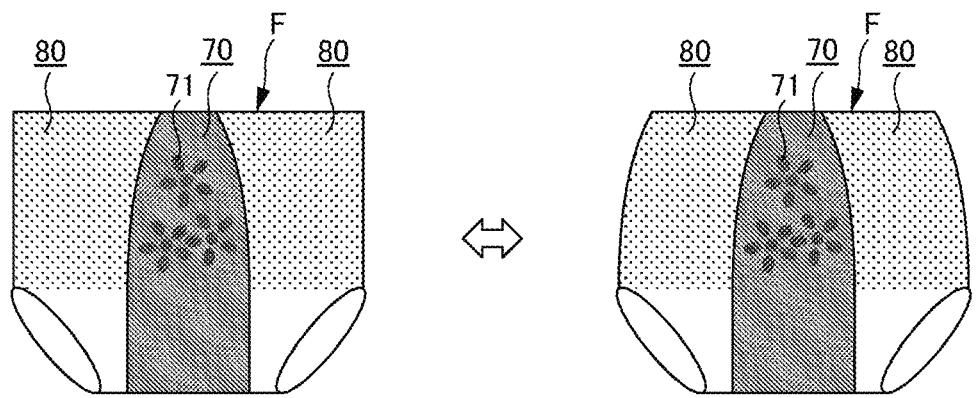
FIGS. 52A and 52B are front views and FIG. 52C is a back view schematically illustrating various modes of the underpants-type disposable diaper.
Figure 52B:
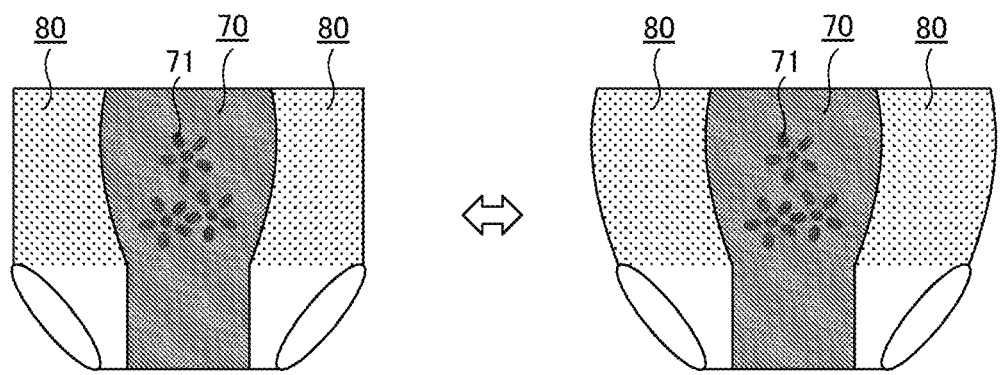
Figure 52C:
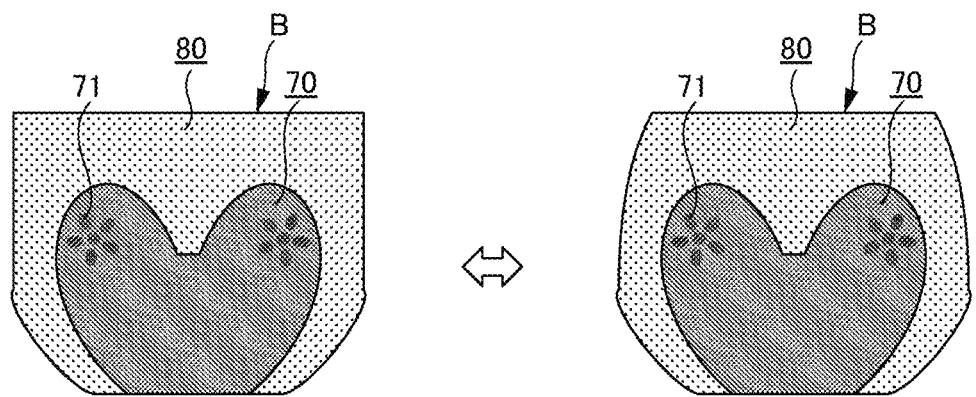

As explained in these modes, in a case in which the non-stretchable region 70 is provided in the central part in the width direction in the outer body 20 of the underpants-type disposable diaper and a fitting property is improved by this configuration, as illustrated in FIGS. 52A and 52B, when both side edges of the non-stretchable region 70 are curved, the fitting property with respect to the surface of the body is further improved. A left diagram of FIG. 52 schematically expresses a spread state, and a right diagram thereof schematically expresses a natural length state. In addition, when the non-stretchable region 70 is provided in both the front body F and the back body B, a shape may be made different between the front and the back using the mode illustrated in FIG. 52A for the front body F and the mode illustrated in FIG. 52C for the back body B, thereby further improving the fitting property with respect to the body surface.

<Others>

A part or a whole of any one of the above-described first to fourth modes may be applied to another mode.

In the above-described first to fourth modes, the first sheet layer 20A and the second sheet layer 20B may be composed of any sheet members, preferably nonwoven fabrics in view of air permeability and flexibility. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 12 to approximately 20 g/m². The first sheet layer 20A and the second sheet layer 20B may be composed of a pair of facing layers prepared by folding back a single sheet that is partially or entirely folded back. For example, as in the illustrated mode, in the waist end portion region 23, a component located on the outer side may be used as the second sheet layer 20B, the folded part 20C formed by folding back to the internal surface side at the waist opening edge thereof may be used as the first sheet layer 20A, and the elastic film 30 may be interposed therebetween. Further, in the other portion, a component located on the inner side may be used as the first sheet layer 20A, a component located on the outer side may be used as the second sheet layer 20B, and the elastic film 30 may be interposed therebetween. The components of the first sheet layer 20A and the second sheet layer 20B may be separately provided across the whole part in the front-back direction, and the elastic film 30 may be interposed between the component of the first sheet layer 20A and the component of the second sheet layer 20B without folding back the components.

The elastic film 30 in the above-described first to fourth modes may be composed of any thermoplastic resin film having elasticity. It is possible to use a film in which a large number of holes or slits are formed for ventilation in addition to a nonporous film. For example, it is possible to use a film obtained by processing a blend of one or two or more types of thermoplastic elastomers such as a styrene type elastomer, an olefin type elastomer, a polyester type elastomer, a polyamide type elastomer, a polyurethane type elastomer, etc. in a film shape using extrusion molding such as a T-die method, an inflation method, etc. In particular, it is preferable when the elastic film 30 has a tensile strength in the width direction (the stretching and contracting direction, the MD) of 8 to 25 N/35 mm, tensile strength in the front-back direction (the direction orthogonal to the stretching and contracting direction, the CD) of 5 to 20 N/35 mm, tensile elongation in the width direction of 450 to 1,050%, and tensile elongation in the front-back direction of 450 to 1,400%. The thickness of the elastic film 30 is not particularly restricted. However, the thickness is preferably in a range of about 20 to 40 μm. In addition, the basis weight of the elastic film 30 is not particularly restricted. However, the basis weight is preferably in a range of about 30 to 45 g/m², and particularly preferably in a range of about 30 to 35 g/m².

<Description of Terms in Specification>

The terms used in the specification have the following meanings unless otherwise stated.

The "front body" and the "back body" refer to front and back portions using the center of the underpants-type disposable diaper in the front-back direction as a boundary. In addition, the crotch portion refers to a front-back direction range including the center of the underpants-type disposable diaper in the front-back direction, and refers to a front-back direction range of a portion having a narrower part when the absorber has the narrower part.

The "elongation at the elastic limit" refers to an elongation at an elastic limit in the stretching and contracting direction (in other words, a state in which the first sheet layer and the second sheet layer are completely spread), and expresses a length at the time of the elastic limit as a percentage when the natural length is set to 100%.

The "area rate" refers to a rate of a target portion to the unit area, and expresses the rate as a percentage by dividing a total area of the target portion (for example, the sheet bond portions 40, the openings of the through holes 31, and the vent hole) in a target region (for example, the stretchable region 80 and the non-stretchable region 70) by an area of the target region. Particularly, an area rate in a region having a stretchable structure (for example, an area rate of sheet bond portions) refers to an area rate in a state of being stretched in the stretching and contracting direction to the elastic limit. In a mode in which a plurality of target portions is provided at intervals, it is desirable to obtain the area rate by setting the target region to a size at which ten or more target portions are included.

The area of the opening of each of the through holes refers to a value obtained when the elastic film stretchable structure is in a natural length state, and refers to a minimum value in a case in which the area of the opening of each of the through holes is not uniform in the thickness direction such as a case in which the area is different between the front and the back of the elastic film.

The MD refers to a machine direction, that is, a line flow direction, and the CD refers to a horizontal direction orthogonal to the MD.

The "stretch rate" represents a value relative to the natural-length (100%)

The "Basis weight" is determined as follows: After the sample or test piece is preliminarily dried, it is allowed to stand in a testing chamber or machine under the standard condition (temperature: 20±5° C., relative humidity: 65% or less) until the constant mass. The preliminary drying represents that the sample or test piece reaches constant mass in an environment within a relative humidity of 10 to 25% and at a temperature not exceeding 50° C. The fiber of an official regain of 0.0% does not need preliminary drying. A cut sample with a size of 200 mm by 250 mm (±2 mm) is prepared from the test piece after the constant mass with a cutting template (200 mm by 250 mm, ±2 mm). The sample is weighed and the weight is multiplied by 20 into the weight per square meter. The resulting value is defined as basis weight.

The "thickness" of the absorber is measured using a thickness measurement apparatus of OZAKI MGF Co., Ltd. (PEACOCK, Dial Thickness Gauge Large Type, Model J-B (Measurement Range 0 to 35 mm) or Model K-4 (Measurement Range 0 to 50 mm)) by horizontally disposing a sample and the thickness measurement apparatus.

A "thickness" other than the above-described thickness is automatically determined with an automatic thickness gauge (KES-G5 handy compression measurement program) under the conditions of a load of 10 gf/cm$^2$ and a pressurization area of 2 cm$^2$.

The "tensile strength" and the "tensile elongation at break" are measured at an initial chuck interval of 50 mm and a speed of testing of 300 mm/min with a tensile tester (for example, AUTOGRAPHAGS-G100N available from SHIMADZU) in accordance with JIS K7127: 1999 "Plastics—Determination of tensile properties", except that the test piece is a rectangle with a width of 35 mm and a length of 80 mm.

The "stretching stress" indicates the tensile stress (N/35 mm) when the sample is stretched in an elastic region that is measured by a tensile test at an initial chuck interval (distance between two adjacent marked lines) of 50 mm and a speed of testing of 300 mm/min in accordance with JIS K7127:1999 "Plastic—Determination of tensile properties", and an extent of stretching may be appropriately determined depending on the test object. A test piece is preferably formed in a rectangular shape having a width of 35 mm and a length of 80 mm or more. If a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress. For example, AUTOGRAPHAGS-G100N manufactured by SHIMADZU may be used as a tensile tester.

The "spread state" refers to a flatly spread state without contraction or slack.

Unless otherwise specified, dimensions of each portion refer to dimensions in the spread state, not the natural length state.

In the absence of description about an environmental condition in a test or measurement, the test or measurement is performed in a test room or a device in a standard state (temperature 20±5° C., relative humidity 65% or less in a test location).

INDUSTRIAL APPLICABILITY

An elastic film stretchable structure of the invention is applicable to a waist portion or a fastening tape of a tape-type disposable diaper in addition to an underpants-type disposable diaper, and to another elastic portion such as a three-dimensional gather, a plane gather, etc. generally used for all absorbent articles including another type of disposable diaper such as a pad-type disposable diaper, a sanitary napkin, etc.

REFERENCE SIGNS LIST

B . . . back body, F . . . front body, T . . . torso region, L . . . intermediate region, 10 . . . inner body, 11 . . . top sheet, 12 . . . liquid impervious sheet, 13 . . . absorber, 13N . . . narrower part, 14 . . . package sheet, 15 . . . gather nonwoven fabric, 16 . . . gather elastic member, 20 . . . outer body, 20A . . . first sheet layer, 20B . . . second sheet layer, 20C . . . folded part, 20X . . . elastic film stretchable structure, 21 . . . side seal portion, 23 . . . waist end portion region, 24 . . . waist end portion elastic member, 25 . . . contraction wrinkle, 29 . . . leg line, 30 . . . elastic film, 31 . . . through hole, 40 . . . sheet bond portion, 70 . . . non-stretchable region, 80 . . . stretchable region.

The invention claimed is:

1. A method of manufacturing an absorbent article, comprising:
    stacking an elastic film between a first sheet layer and a second sheet layer to form an elastic film stretchable structure, wherein a region including the elastic film stretchable structure has a stretchable region stretchable at least in one direction and a non-stretchable region being provided at least at one side of the stretchable region in a stretching and contracting direction and having an elongation at an elastic limit in the stretching and contracting direction of 130% or less;
    stretching the elastic film in a machine direction (MD) in a state the elastic film is stacked between the first sheet layer and the second sheet layer;
    forming sheet bond portions in the stretchable region by joining the first sheet layer and the second sheet layer at a large number of positions arranged at intervals in each of the MD and a cross direction (CD) (Cross Direction) orthogonal to the MD; and
    in the non stretchable region, performing a welding process in the non-stretchable region in a welding pattern of one row extending in a dotted line in the CD or a plurality of rows, each of which is extending in a dotted line in the CD, and which are disposed at intervals in the MD, to melt the elastic film in the welding pattern of the dotted line, thereby forming perforation, joining the first sheet layer and the second sheet layer by way of through holes of the perforation to form sheet bond portions, and then fracturing the perforation by a tensile force applied by stretching of the elastic film.

2. The method of manufacturing an absorbent article according to claim 1, wherein in the non-stretchable region, the welding process is set to perform in the welding pattern of the plurality of rows disposed at intervals in the MD, the perforation is formed in a welding pattern of the rows, each of which is extending in the dotted line, and which are located every other row in the MD, and is fractured by the tensile force applied by stretching of the elastic film, and pieces of the elastic film formed by applying the tensile force are left in a natural length state so as to cross remained rows in a welding pattern of the rows, each of which is extending in the dotted line, and the remained rows locating every other row of the sheet bond portions.

3. The method of manufacturing an absorbent article according to claim 1, wherein
    the elastic film is an elastic film having a tensile strength in the MD of 8 to 25 N/35 mm, a tensile strength in the CD of 5 to 20 N/35 mm, a tensile elongation in the MD of 450 to 1,050%, and a tensile elongation in the CD of 450 to 1,400%, and
    in performing the welding process, the welding pattern of the row extending in the dotted line is set to a pattern having an interval in the CD between two adjacent welding points of 1 mm or less, and the elastic film is put in a state in which the same is stretched 2 to 5 times in the MD.

4. The method of manufacturing an absorbent article according to claim 1, wherein
- the welding process is performed by a welding process device on a production line while the first sheet layer, the second sheet layer, and the elastic film are continuously conveyed on the production line, and
- the welding pattern of the dotted line is set to have a section in which the interval in the CD between two adjacent welding points is a first interval, and a section in which the interval in the CD between the two adjacent welding points is a second interval being larger than the first interval.

\* \* \* \* \*